United States Patent
Numata et al.

(10) Patent No.: US 11,697,645 B2
(45) Date of Patent: Jul. 11, 2023

(54) HETEROCYCLIC COMPOUND, COMPOSITION INCLUDING HETEROCYCLIC COMPOUND, AND ORGANIC LIGHT-EMITTING DEVICE INCLUDING HETEROCYCLIC COMPOUND

(71) Applicant: Samsung Electronics Co., Ltd., Suwon-si (KR)

(72) Inventors: Masaki Numata, Kanagawa (JP); Mitsunori Ito, Kanagawa (JP); Norihito Ishii, Kanagawa (JP); Rie Sakurai, Kanagawa (JP)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 746 days.

(21) Appl. No.: 16/722,261

(22) Filed: Dec. 20, 2019

(65) Prior Publication Data
US 2020/0207732 A1    Jul. 2, 2020

(30) Foreign Application Priority Data

Dec. 28, 2018 (JP) .................................. 2018-248443
Jul. 1, 2019 (KR) ........................ 10-2019-0079003

(51) Int. Cl.
*H01L 51/50* (2006.01)
*C07D 333/76* (2006.01)
(Continued)

(52) U.S. Cl.
CPC ......... *C07D 333/76* (2013.01); *C07D 307/91* (2013.01); *C07D 403/04* (2013.01);
(Continued)

(58) Field of Classification Search
None
See application file for complete search history.

(56) References Cited

U.S. PATENT DOCUMENTS 8,743,031 B2   6/2014   Hashimoto et al.
9,190,620 B2   11/2015   Zeng et al.
(Continued)

FOREIGN PATENT DOCUMENTS

CN   106318379 A   1/2017
EP   2966706 A2   1/2016
(Continued)

OTHER PUBLICATIONS

Extended European search report issued by the European Patent Office dated Mar. 16, 2020 in the examination of the European Patent Application No. 19218571.8, which corresponds to the U.S. Application above.

(Continued)

*Primary Examiner* — Gregory D Clark
(74) *Attorney, Agent, or Firm* — Cantor Colburn LLP

(57) ABSTRACT

A heterocyclic compound, a composition including the heterocyclic compound, and an organic light-emitting
(Continued)

device including the heterocyclic compound are disclosed. The heterocyclic compound is represented by Formula 1:

Formula 1

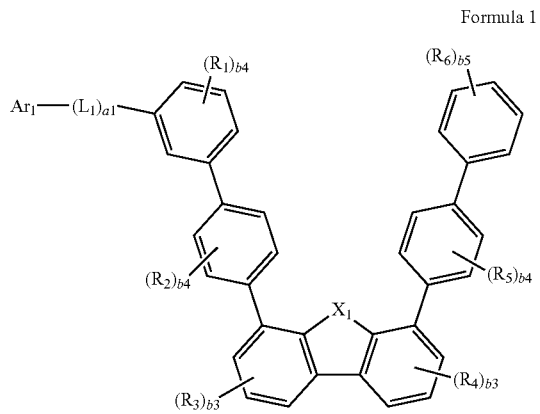

wherein, $X_1$, $L_1$, a1, $Ar_1$, $R_1$ to $R_6$, b3, b4, and b5 are described herein.

19 Claims, 5 Drawing Sheets

(51) Int. Cl.
| | |
|---|---|
| *C07D 307/91* | (2006.01) |
| *C07D 403/04* | (2006.01) |
| *C07D 403/14* | (2006.01) |
| *C07D 487/04* | (2006.01) |
| *H01L 51/00* | (2006.01) |

(52) U.S. Cl.
CPC ......... *C07D 403/14* (2013.01); *C07D 487/04* (2013.01); *H01L 51/0058* (2013.01); *H01L 51/0059* (2013.01); *H01L 51/0072* (2013.01); *H01L 51/0073* (2013.01); *H01L 51/0074* (2013.01); *H01L 51/5016* (2013.01)

(56) References Cited

U.S. PATENT DOCUMENTS

| | | | |
|---|---|---|---|
| 9,680,111 | B2 | 6/2017 | Feldman et al. |
| 2013/0009139 | A1 | 1/2013 | Ohsawa et al. |
| 2013/0341599 | A1 | 12/2013 | Xia et al. |
| 2015/0249221 | A1* | 9/2015 | Zeng .................. C07D 409/04 548/440 |
| 2015/0349268 | A1 | 12/2015 | Zeng et al. |
| 2016/0093808 | A1 | 3/2016 | Adamovich et al. |
| 2016/0233436 | A1 | 8/2016 | Zeng et al. |
| 2017/0117487 | A1 | 4/2017 | Kawakami et al. |

FOREIGN PATENT DOCUMENTS

| | | |
|---|---|---|
| JP | 2012033784 A | 2/2012 |
| JP | 2012508258 A | 4/2012 |
| JP | 2013033958 A | 2/2013 |
| JP | 2014509067 A | 4/2014 |
| JP | 5729957 B2 | 6/2015 |
| JP | 5763309 B2 | 6/2015 |
| JP | 2017081909 A | 5/2017 |
| KR | 1020170096860 A | 8/2017 |
| WO | 2012133644 A1 | 10/2012 |
| WO | 2017092495 A1 | 6/2017 |

OTHER PUBLICATIONS

English Translation of Office Action issued in corresponding JP Patent Application No. 2018-248443, dated Dec. 27, 2022, 7 pp.
Office Action issued in corresponding JP Patent Application No. 2018-248443, dated Dec. 27, 2022, 5 pp.

* cited by examiner

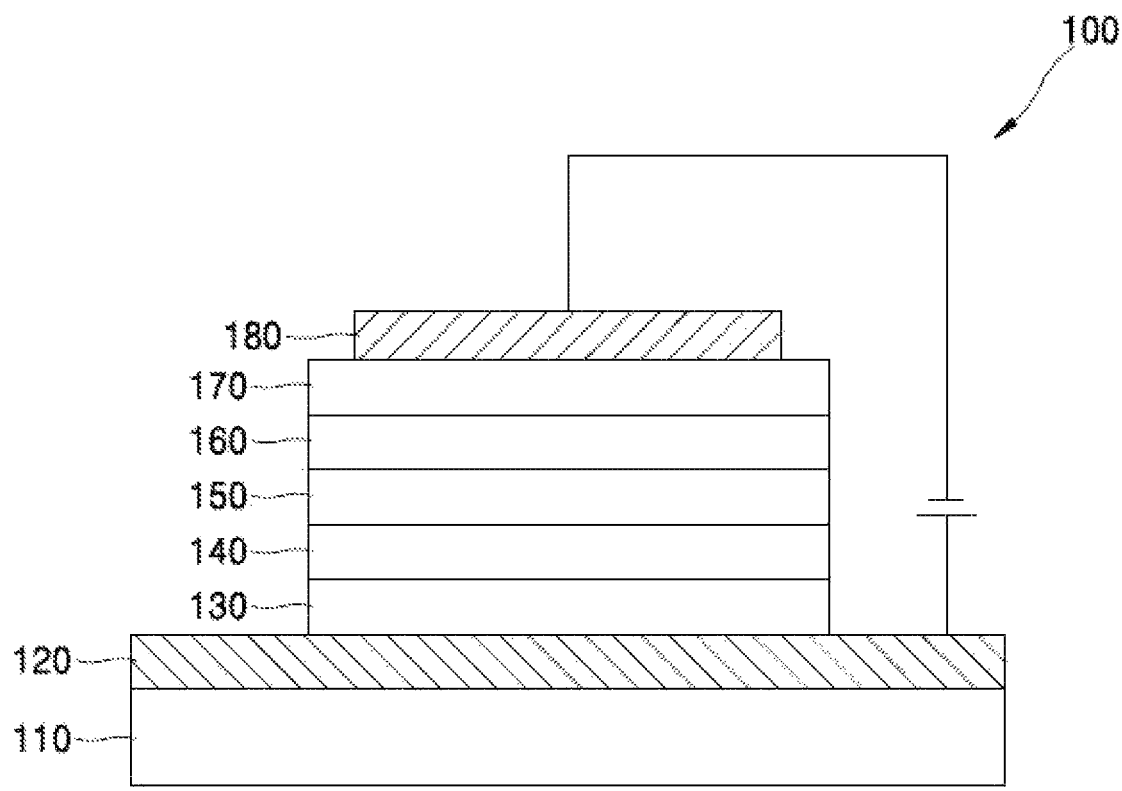

HETEROCYCLIC COMPOUND, COMPOSITION INCLUDING HETEROCYCLIC COMPOUND, AND ORGANIC LIGHT-EMITTING DEVICE INCLUDING HETEROCYCLIC COMPOUND

CROSS-REFERENCE TO RELATED APPLICATIONS

This application claims priority to and the benefit of Japanese Patent Application No. 2018-248443, filed on Dec. 28, 2018, in the Japanese Patent Office and Korean Patent Application No. 10-2019-0079003, filed on Jul. 1, 2019, in the Korean Intellectual Property Office, and all the benefits accruing therefrom under 35 U.S.C. § 119, the contents of which are incorporated herein in their entireties by reference.

BACKGROUND

1. Field

The present disclosure relates to a heterocyclic compound, a composition (e.g., for an organic light-emitting device) including the heterocyclic compound, and an organic light-emitting device including the heterocyclic compound.

2. Description of the Related Art

Organic light-emitting devices (OLEDs) are self-emissive devices that, as compared with other types of devices of the related art, have wide viewing angles, high contrast ratios, and short response times, and excellent characteristics in terms of luminance, driving voltage, and response speed. In addition, OLEDs may produce full-color images.

OLEDs include an anode, a cathode, and an organic layer between the anode and the cathode and including an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state to thereby generate light.

SUMMARY

Provided are a heterocyclic compound, a composition including the heterocyclic compound, and an organic light-emitting device including the heterocyclic compound.

In general, in preparation of an organic light-emitting device, an organic film included in the organic light-emitting device is formed by a dry deposition method such as a vapor deposition method. However, film formation by the dry deposition method such as the vapor deposition method has problems in terms of time and cost. Therefore, instead of a dry deposition method, use of a wet deposition method, such as a solution coating method, (hereinafter, a coating method), which may save time and cost, is examined.

However, when the wet deposition method is applied to existing compounds, there is a problem in that the pot life of a solution is short because the solubility of the compound is poor. In addition, the organic light-emitting device using such compounds has a problem of low efficiency and short lifespan.

Therefore, a compound is provided, which may have high solubility and/or long pot life of a solution and/or may achieve an organic light-emitting device having high efficiency and/or long lifespan.

In particular, an organic light-emitting device including the heterocyclic compound may have high luminescence efficiency and/or long lifespan. In addition, the heterocyclic compound has a low glass transition temperature and/or high solubility, thereby increasing the pot life of the solution containing the compound. Thus, the heterocyclic compound may be suitable for use in a solution coating method.

Additional aspects will be set forth in part in the description which follows and, in part, will be apparent from the description, or may be learned by practice of the presented embodiments.

According to an aspect of an embodiment, a heterocyclic compound is represented by Formula 1:

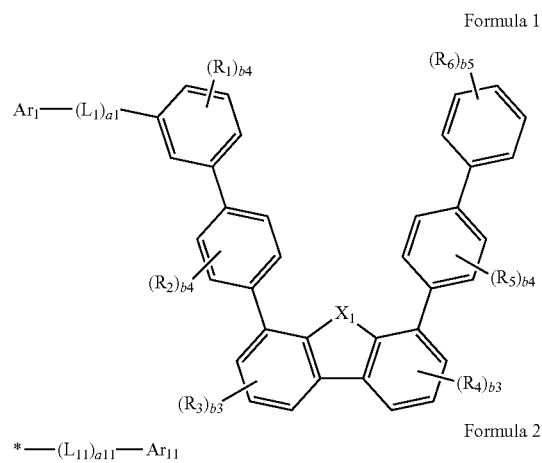

Formula 1

Formula 2

$*$—$(L_{11})_{a11}$—$Ar_{11}$ wherein, in Formulae 1 and 2, $X_1$ is O, S, or Se, $L_1$ and $L_{11}$ are each independently a single bond, a substituted or unsubstituted benzene group, or a substituted or unsubstituted naphthalene group, a1 and a11 are each independently an integer from 1 to 10, $Ar_1$ and $Ar_{11}$ are each independently a substituted or unsubstituted benzene group, or a substituted or unsubstituted naphthalene group, $R_1$ to $R_6$ are each independently a group represented by Formula 2, hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, or a substituted or unsubstituted $C_1$-$C_{60}$ alkoxy group, b3 is an integer from 0 to 3, b4 is an integer from 0 to 4, b5 is an integer from 0 to 5, at least one substituent of the substituted benzene group, the substituted naphthalene group, the substituted $C_1$-$C_{60}$ alkyl group, the substituted $C_2$-$C_{60}$ alkenyl group, the substituted $C_2$-$C_{60}$ alkynyl group, and the substituted $C_1$-$C_{60}$ alkoxy group is:

deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, or any combination thereof;

a $C_1$-$C_{60}$ alkyl group, a $C_2$-$C_{60}$ alkenyl group, a $C_2$-$C_{60}$ alkynyl group, a $C_1$-$C_{60}$ alkoxy group, or any combination thereof, each substituted with at least one deuterium, —F, —Cl, —Br, —I, —$CD_3$, —$CD_2H$, —$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, $Si(Q_{11})(Q_{12})(Q_{13})$, —$N(Q_{11})(Q_{12})$, —$C(=O)(Q_{11})$, or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, or any combination thereof:

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, or any combination thereof, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, —$Si(Q_{21})(Q_{22})(Q_{23})$, —$N(Q_{21})(Q_{22})$, —$C(=O)(Q_{21})$, or any combination thereof; or —$Si(Q_{31})(Q_{32})(Q_{33})$, —$N(Q_{31})(Q_{32})$, —$C(=O)(Q_{31})$, or any combination thereof, wherein $Q_{11}$ to $Q_{13}$, $Q_{21}$ to $Q_{23}$, and $Q_{31}$ to $Q_{33}$ are each independently hydrogen, deuterium, a $C_1$-$C_{20}$ alkyl group, a $C_1$-$C_{20}$ alkoxy group, a phenyl group, or a biphenyl group, and

* indicates a binding site to an adjacent atom.

According to another aspect, a composition includes at least one heterocyclic compound represented by Formula 1.

According to still another aspect, an organic light-emitting device includes: a first electrode; a second electrode; and an organic layer between the first electrode and the second electrode and including an emission layer and at least one heterocyclic compound described above.

BRIEF DESCRIPTION OF THE DRAWINGS

These and/or other aspects will become apparent and more readily appreciated from the following description of the embodiments, taken in conjunction with the accompanying drawings in which:

FIG. 5 is a schematic cross-sectional view illustrating an organic light-emitting device according to an embodiment.

DETAILED DESCRIPTION

Figure 1:
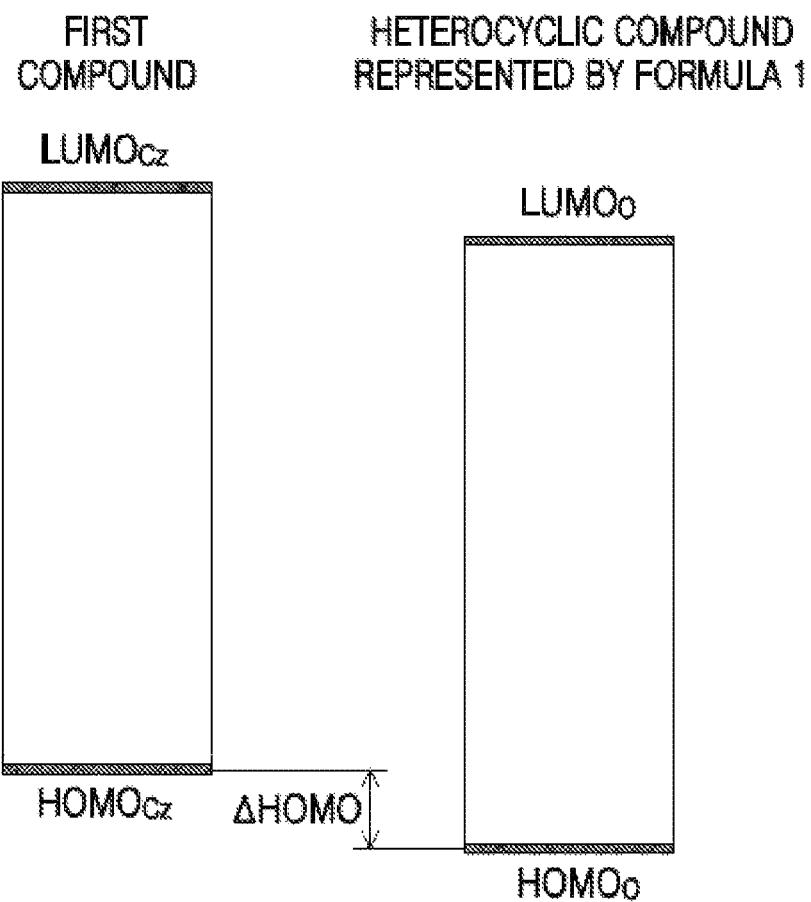
FIG. 1 is a diagram for illustrating an exemplary energy level relationship between the heterocyclic compound represented by Formula 1 and a first compound containing a carbazole group in a composition according to one or more embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween In contrast, when an element is referred to as being "directly on" another element, there are no intervening elements present It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section Thus, a first element, component, region, layer or section discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise.

"Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded Thus, the regions illustrated in the figures are schematic in nature and their shapes are not intended to illustrate the precise shape of a region and are not intended to limit the scope of the present claims.

Heterocyclic Compound

A heterocyclic compound according to one or more embodiments is represented by Formula 1:

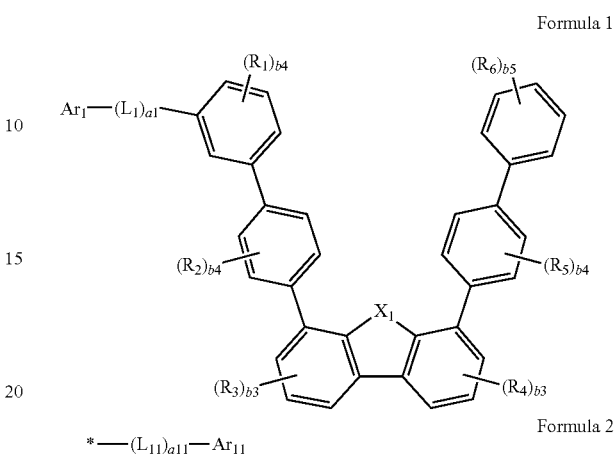

Formula 1

Formula 2 wherein, in Formula 1, X1 is O, S, or Se.

In some embodiments, $X_1$ may be O or S.

In Formulae 1 and 2, $L_1$ and $L_{11}$ are each independently a single bond, a substituted or unsubstituted benzene group, or a substituted or unsubstituted naphthalene group.

In some embodiments, $L_1$ and $L_{11}$ may each independently be a single bond or a group represented by Formulae 3-1 or 3-2, and when a1 and a11 are each 2 or greater, $(L_1)_{a1}$ and $(L_{11})_{a11}$ may each independently be a single bond or a group represented by Formulae 3-1 to 3-3:

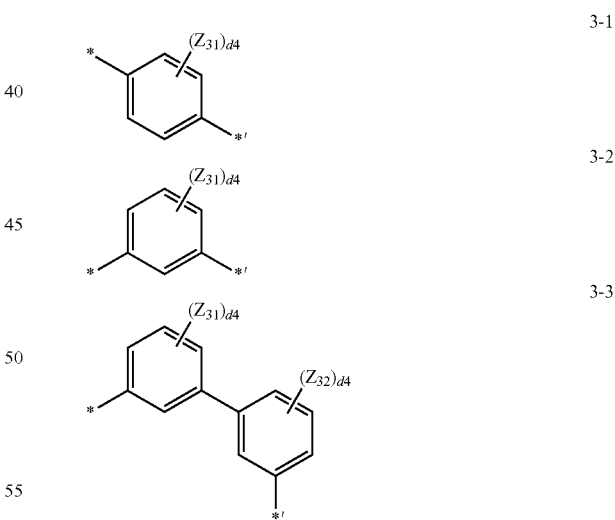

wherein, $Z_{31}$ and $Z_{32}$ may each independently be hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, or —Si($Q_{31}$)($Q_{32}$)($Q_{33}$), d4 may be an integer from 0 to 4, $Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group, and

* and *' each indicate a binding site to an adjacent atom.

In Formulae 1 and 2, a1 and a11 are each independently an integer from 1 to 10, a1 indicates the number of $L_1$(s); when a1 is 2 or greater, $L_1$(s) in the number of a1 may be identical to or different from each other, a11 indicates the number of $L_{11}$(s); when a11 is 2 or greater, $L_{11}$(s) in the number of a11 may be identical to or different from each other.

In some embodiments, a1 and a11 may each independently be an integer 1 or 2, but embodiments are not limited thereto.

In some embodiments, i) $L_1$ may be a single bond, $L_{11}$ may be a substituted or unsubstituted benzene group, and a11 may be 1 or 2;

ii) $L_1$ and $L_{11}$ may each be a substituted or unsubstituted benzene group, and a1 and a11 may each be 1;

iii) $L_1$ and $L_{11}$ may each be a substituted or unsubstituted benzene group, a1 may be 1, and a11 may be 2; or iv) $L_1$ and $L_{11}$ may each be a substituted or unsubstituted benzene group, and a1 and a11 may each be 2.

In Formulae 1 and 2, $Ar_1$ and $Ar_{11}$ are each independently a substituted or unsubstituted benzene group, or a substituted or unsubstituted naphthalene group.

In some embodiments, the moiety represented by *-$(L_1)_{a1}$-$Ar_1$ may be represented by any one of Formulae 4-1 to 4-5:

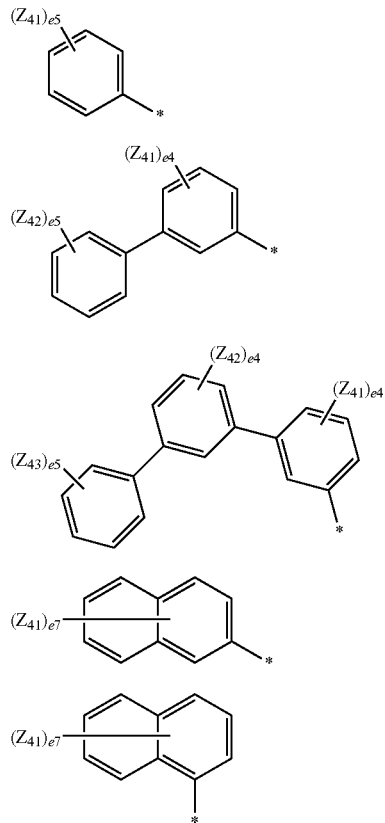

wherein, $Z_{41}$ to $Z_{43}$ may each independently be hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, or —Si($Q_{31}$)($Q_{32}$)($Q_{33}$), e4 may be an integer from 0 to 4, e5 may be an integer from 0 to 5, e7 may be an integer from 0 to 7, $Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group, and * indicates a binding site to an adjacent atom.

In some embodiments, the group represented by Formula 2 may be any group represented by any of Formulae 2-1 to 2-6:

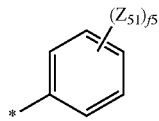

2-1

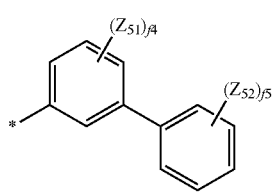

2-2

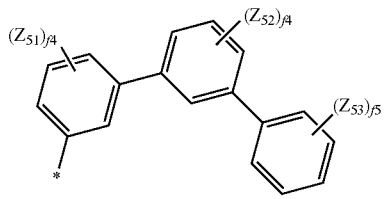

2-3

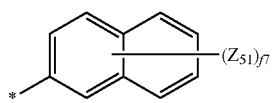

2-4

2-5

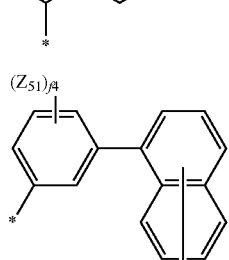

2-6 wherein, $Z_{51}$ to $Z_{53}$ may each independently be hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, or —Si($Q_{31}$)($Q_{32}$)($Q_{33}$), f4 may be an integer from 0 to 4, f5 may be an integer from 0 to 5, f7 may be an integer from 0 to 7, $Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group, and

* indicates a binding site to an adjacent atom.

In some embodiments, i) the moiety represented by *-$(L_1)_{a1}$-$Ar_1$ may be a group represented by Formula 4-1, and the group represented by Formula 2 may be represented by any of Formulae 2-1 to 2-3, 2-5, or 2-6;

ii) the moiety represented by *-$(L_1)_{a1}$-$Ar_1$ may be a group represented by Formula 4-2, and the group represented by Formula 2 may be represented by Formulae 2-2 or 2-3;

iii) the moiety represented by *-$(L_1)_{a1}$-$Ar_1$ may be a group represented by Formula 4-3, and the group represented by Formula 2 may be represented by Formula 2-3;

iv) the moiety represented by *-$(L_1)_{a1}$-$Ar_1$ may be a group represented by Formula 4-4, and the group represented by Formula 2 may be represented by Formulae 2-2 or 2-3; or v) the moiety represented by *-$(L_1)_{a1}$-$Ar_1$ may be a group represented by Formula 4-5, and the group represented by Formula 2 may be represented by Formulae 2-2 or 2-6:

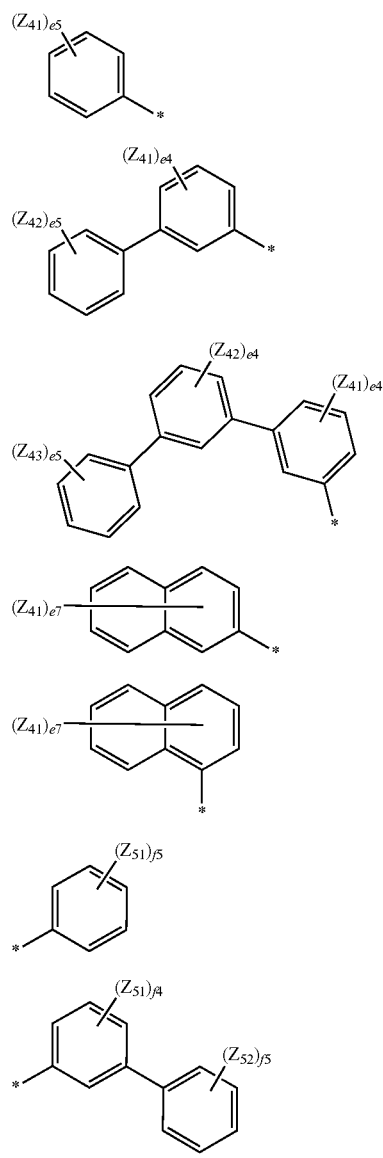

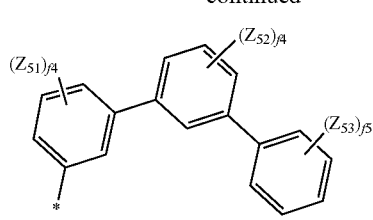

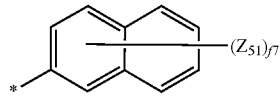

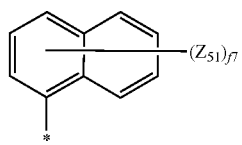

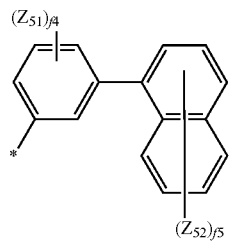

wherein, $Z_{41}$ to $Z_{43}$ and $Z_{51}$ to $Z_{53}$ may each independently be hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, or —Si$(Q_{31})(Q_{32})(Q_{33})$, e4 and f4 may each independently be an integer from 0 to 4, e5 and f5 may each independently be an integer from 0 to 5, e7 and f7 may each independently be an integer from 0 to 7, $Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group, and

* indicates a binding site to an adjacent atom.

In Formulae 1 and 2, $R_1$ to $R_6$ are each independently a group represented by Formula 2, hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, or a substituted or unsubstituted $C_1$-$C_{60}$ alkoxy group, b3 may be an integer from 0 to 3, b4 may be an integer from 0 to 4, and b5 may be an integer from 0 to 5.

In some embodiments, $R_1$ and $R_6$ may each independently be a group represented by Formula 2 or hydrogen.

In some embodiments, $R_2$ to $R_5$ may each independently be hydrogen, deuterium, —F, —Cl, —Br, —I, a cyano group, a $C_1$-$C_{20}$ alkyl group, a $C_2$-$C_{20}$ alkenyl group, a $C_2$-$C_{20}$ alkynyl group, a $C_1$-$C_{20}$ alkoxy group; or a $C_1$-$C_{20}$ alkyl group, a $C_2$-$C_{20}$ alkenyl group, a $C_2$-$C_{20}$ alkynyl group, or a $C_1$-$C_{20}$ alkoxy group, each substituted with at least one deuterium, —F, —Cl, —Br, —I, a cyano group, or any combination thereof.

In some embodiments, the heterocyclic compound may be represented by any of Formulae 1-1 to 1-4:

Formula 1-1

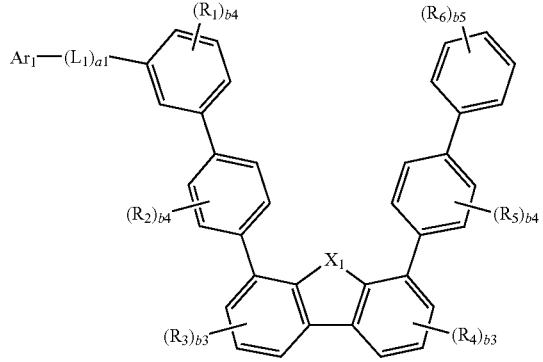

Formula 1-2

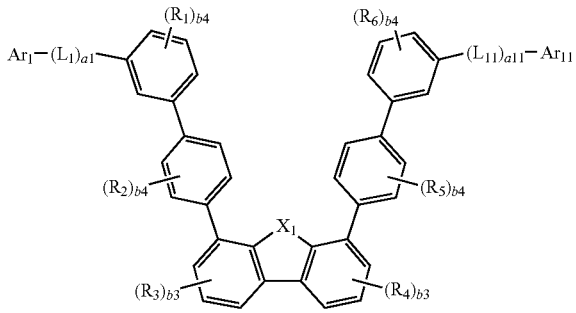

Formula 1-3

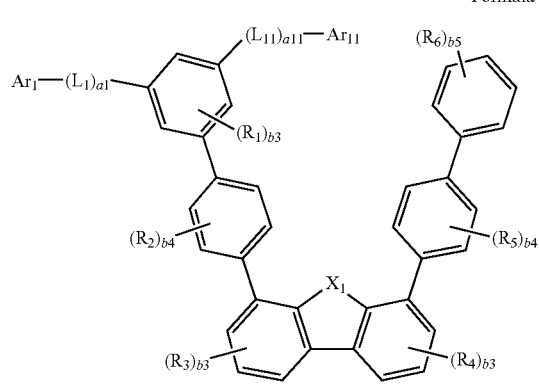

Formula 1-4

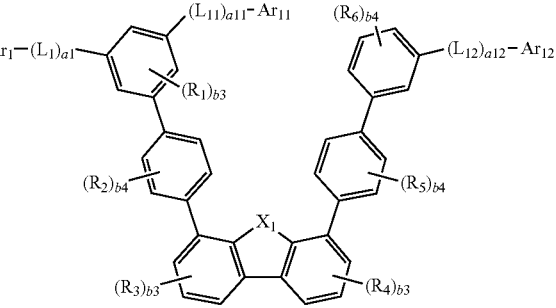

wherein, in Formulae 1-1 to 1-4, $X_1$, $L_1$, $L_{11}$, a1, a11, $Ar_1$, $Ar_{11}$, b3, b4, and b5 may respectively be understood by referring to the descriptions of $X_1$, $L_1$, $L_{11}$, a1, a11, $Ar_1$, $Ar_{11}$, b3, b4, and b5 described above, $L_{12}$, a12 and $Ar_{12}$ may respectively be understood by referring to the descriptions of $L_{11}$, a11, and $Ar_{11}$ described above, and $R_1$ to $R_6$ may each independently be hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, or a substituted or unsubstituted $C_1$-$C_{60}$ alkoxy group.

In some embodiments, in Formula 1-2, *-$(L_1)_{a1}$-$Ar_1$ and *-$(L_{11})_{a11}$-$Ar_{11}$ may be different from each other, but embodiments are not limited thereto.

In some embodiments, in Formula 1-4, *-$(L_1)_{a1}$-$Ar_1$ and *-$(L_{12})_{a12}$-$Ar_{12}$ may be different from each other, but embodiments are not limited thereto.

In some embodiments, the heterocyclic compound may include five or more benzene groups, but embodiments are not limited thereto.

In some embodiments, the heterocyclic compound may satisfy Equation 1:

$$|E_{HOMO} - E_{LUMO}| \geq 3.0 \text{ eV} \qquad \text{Equation 1}$$

wherein, in Equation 1, $E_{HOMO}$ indicates the highest occupied molecular orbital (HOMO) energy level value of the heterocyclic compound, and $E_{LUMO}$ indicates the lowest unoccupied molecular orbital (LUMO) energy level value of the heterocyclic compound.

The value of $|E_{HOMO} - E_{LUMO}|$ is not particularly limited provided that the value satisfies Equation 1. For example, the value of $|E_{HOMO} - E_{LUMO}|$ may be 3.1 eV or higher, or for example, 3.2 eV or higher.

For example, the value of $|E_{HOMO} - E_{LUMO}|$ may be 6.0 eV or lower.

For example, the heterocyclic compound may satisfy Equation 1-1:

$$3.0 \text{ eV} \leq |E_{HOMO} - E_{LUMO}| \leq 6.0 \text{ eV}. \qquad \text{Equation 1-1}$$

In some embodiments, the heterocyclic compound may have a glass transition temperature ($T_g$) of 140° C. or lower. In some embodiments, a glass transition temperature ($T_g$) of the heterocyclic compound is not particularly limited; however, the glass transition temperature ($T_g$) may be 120° C. or lower, for example, 105° C. or lower, and 60° C. or higher.

In some embodiments, the heterocyclic compound may be at least one of Compounds 1 to 24, but embodiments are not limited thereto:

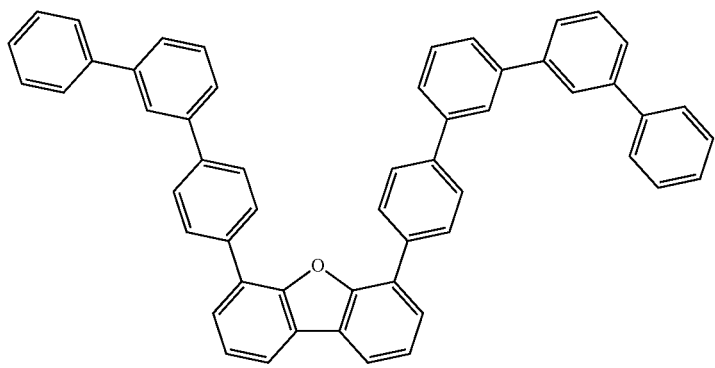
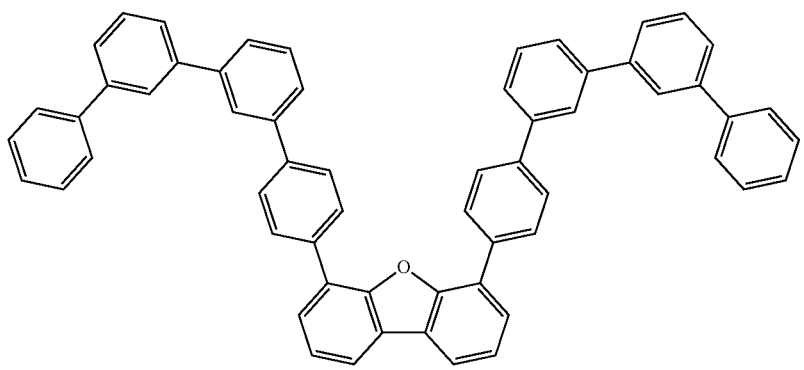
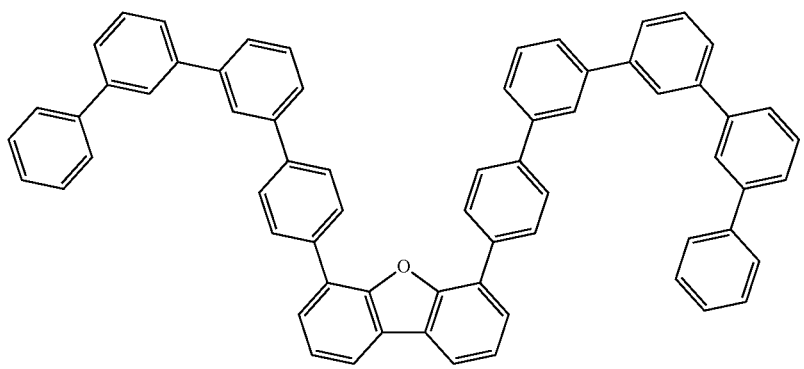
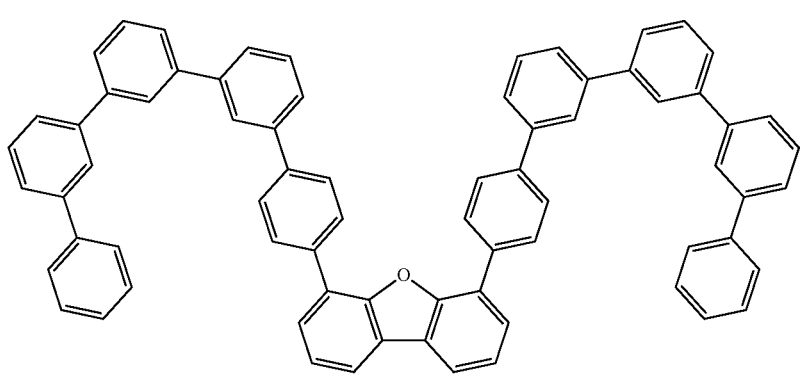

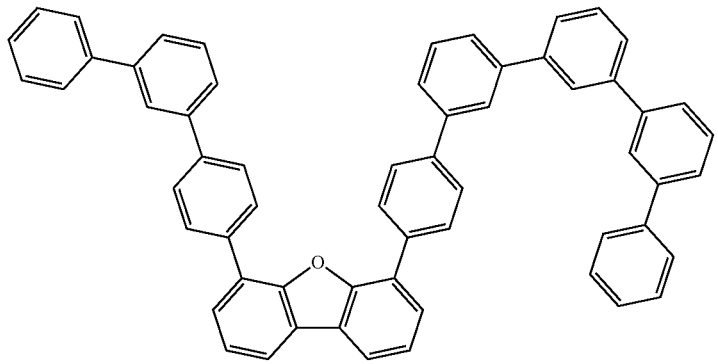
5
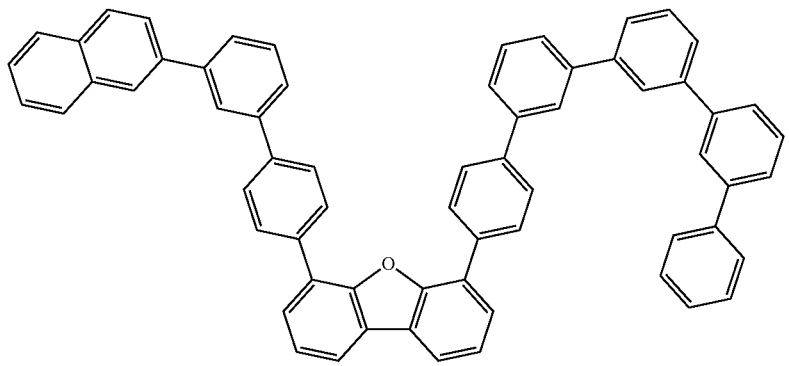
6
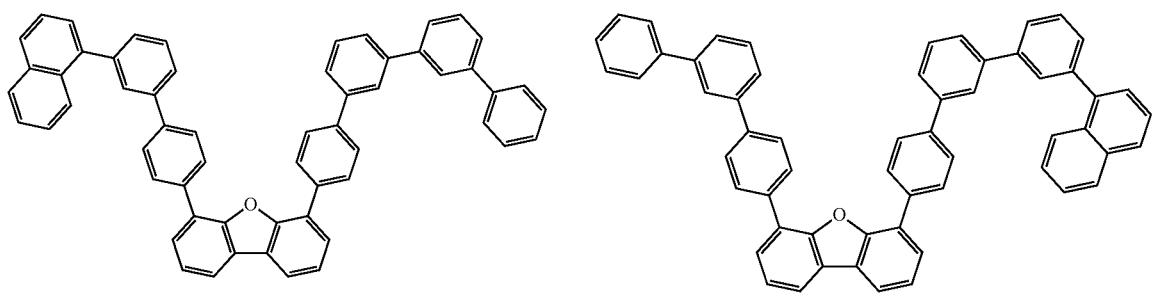
7 8
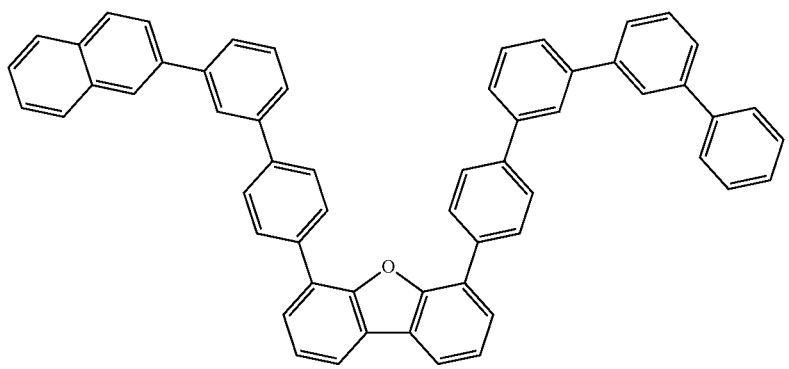
9

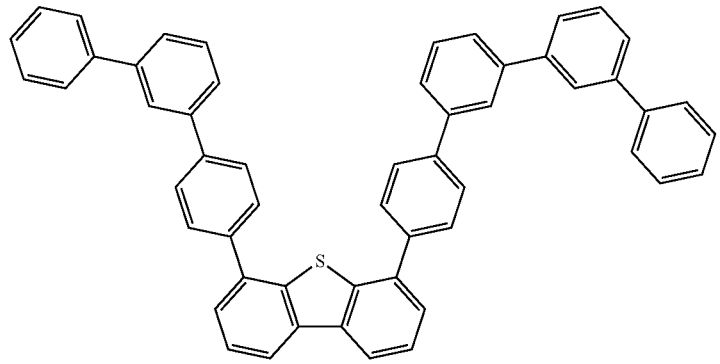
10
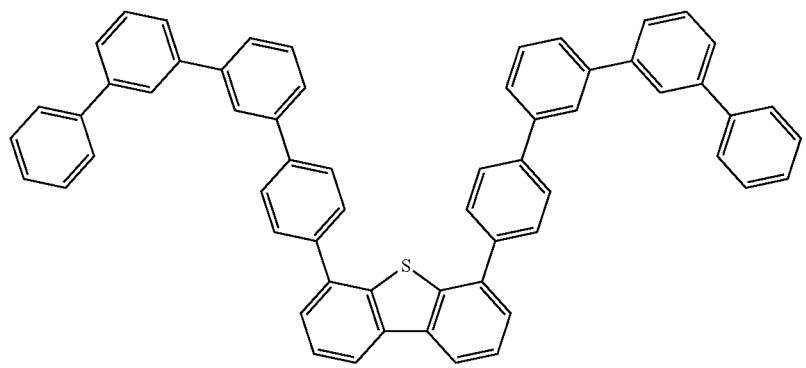
11
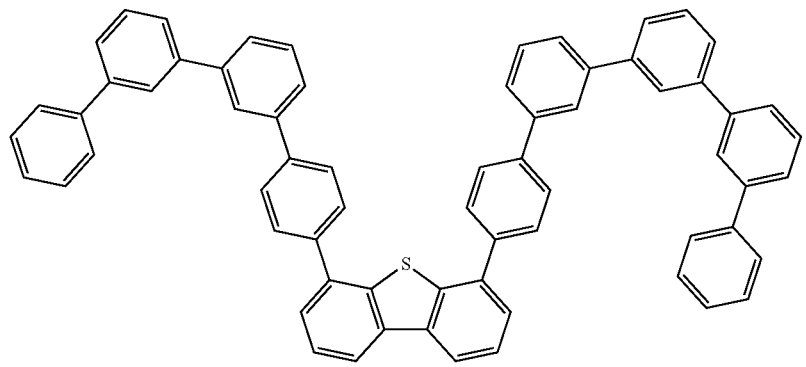
12
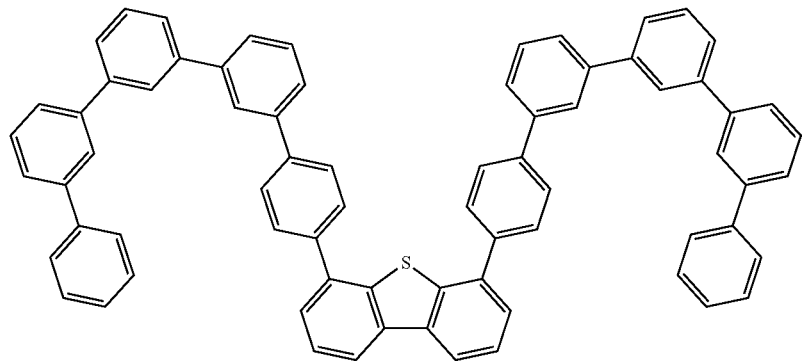
13

-continued
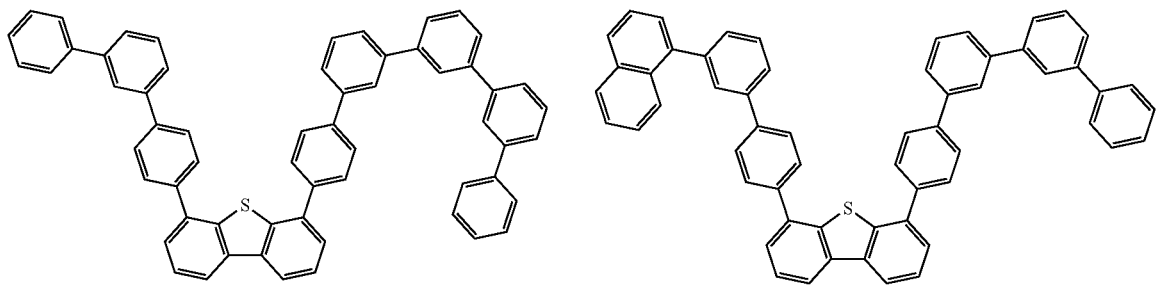
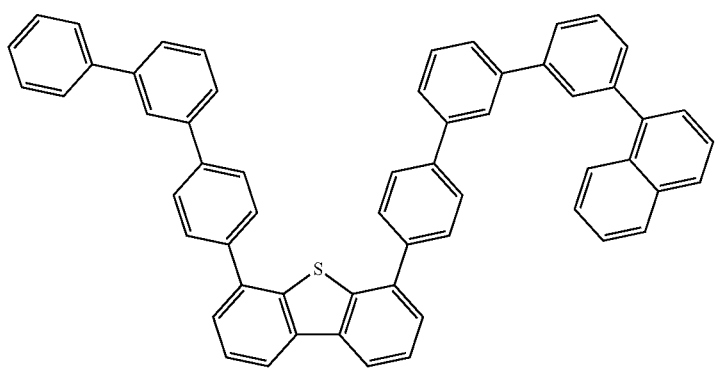
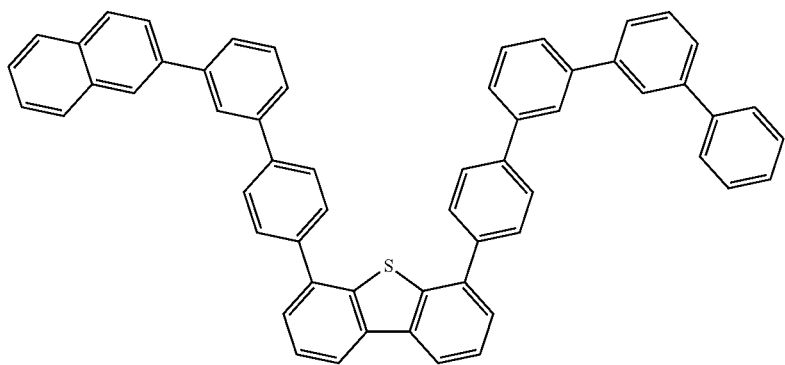
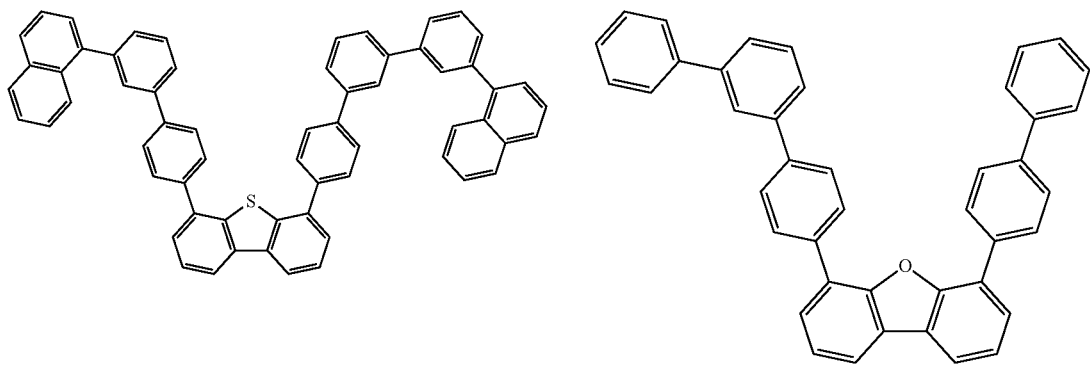

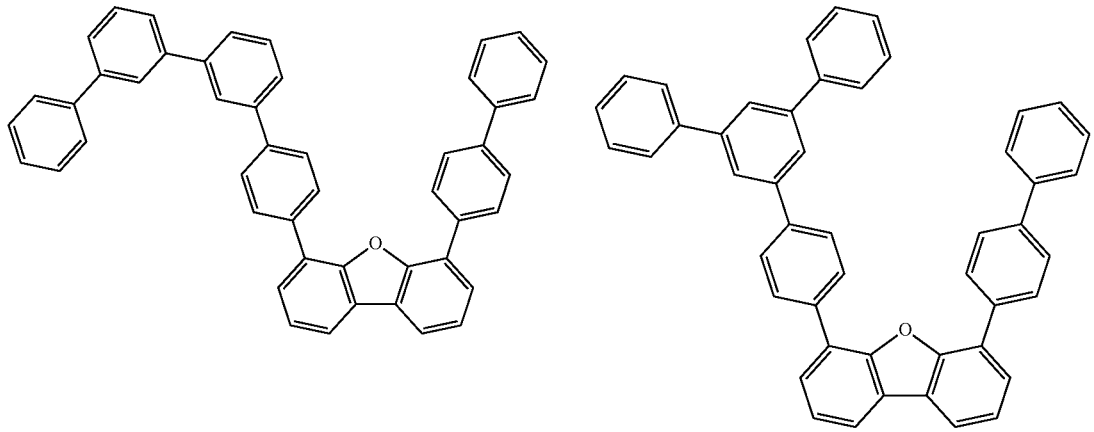

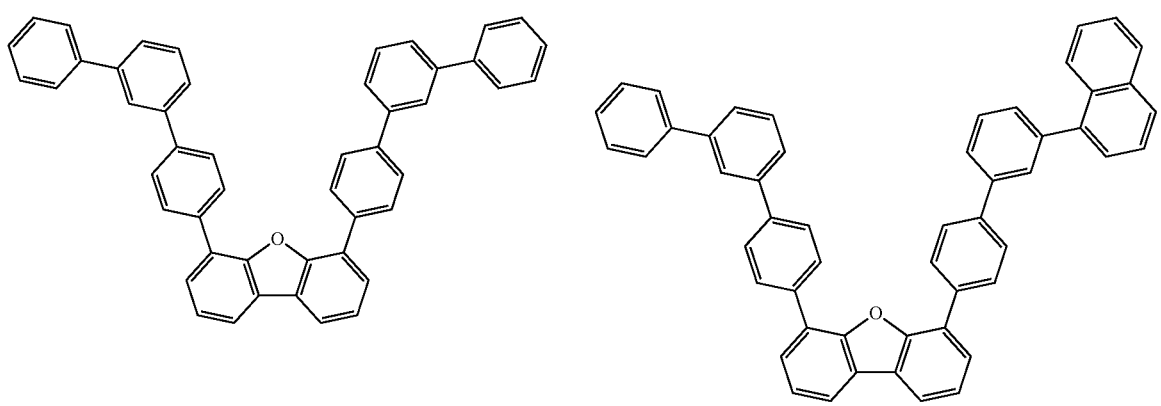

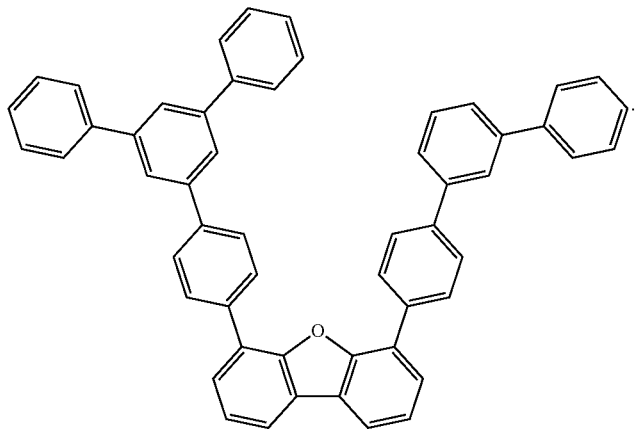

In some embodiments, the heterocyclic compound represented by Formula 1 may be at least one of Compounds 1, 2, and 11, but embodiments are not limited thereto.

The heterocyclic compound represented by Formula 1 may not further include a condensed ring in which three or more rings are condensed, other than a dibenzofuran moiety, a dibenzothiophene moiety, or a dibenzoselenophene moiety containing $X_1$.

When a condensed ring in which three or more rings are condensed is further included in a compound, although the compound has a molecular weight similar to that of the heterocyclic compound represented by Formula 1, the compound has a lower number of conformations (number of conformation patterns) than the heterocyclic compound represented by Formula 1. In addition, in a compound further including a condensed ring in which three or more rings are condensed, since there is a strong cohesion force between planes, aggregation of molecules may be prone to occur, and crystallization may also be prone to occur. Therefore, when such a compound is applied to a wet deposition method, dispersion of the compound in the solvent is difficult to achieve at a molecular level, and solubility of the compound may be low. Moreover, even when a solution containing such a compound is prepared, precipitation in a crystallization solution may be facilitated, and the pot life of the solution may be short. In addition, such a compound may have a high glass transition temperature ($T_g$) due to the aforementioned molecular structure. As a result, when forming an organic light-emitting device, at least one of the central position and the steric conformation of the molecule of such a compound in a film containing the compound is firmly fixed. In a drying process of removing a solvent, pores through which volatile impurity molecules (e.g., a solvent, water, oxygen, etc.) pass through a film are less likely to occur. Therefore, volatile impurity molecules are not completely removed, resulting in lower luminescence efficiency or shorter emission lifespan of an organic light-emitting device.

In addition, in a compound further containing an azine-based moiety containing at least one nitrogen atom, unlike a benzene group or a naphthalene group defined in Formula 1; other than the condensed ring having three or more rings, a depth of the LUMO level and carrier mobility of at least one of electrons and holes may greatly differ. Accordingly, with the compound containing an azine-based moiety, it is difficult to adjust the carrier balance. As a result, distributions of recombination of charges and formation of excitons in a layer containing the compound are concentrated in one position, a load is concentrated, and thus, emission lifespan of the organic light-emitting device may be shortened.

On the other hand, the heterocyclic compound represented by Formula 1 may have an increased the number of conformations, and thus, aggregation of molecules and/or crystallization may be prevented. In addition, the heterocyclic compound represented by Formula 1 may have a relatively low glass transition temperature by not including two or more rigid condensed rings, such as dibenzofuran, in which three or more rings are condensed. As a result, the compound may have high solubility, precipitation in a solution may be difficult, and the pot life of the solution may also become long. In addition, because of the relatively low glass transition temperature, the compound molecules in the film containing the heterocyclic compound represented by Formula 1 may be thermally moved relatively easily during drying process of removing the solvent. Therefore, pores through which volatile impurity molecules pass through are likely to occur, and diffusion and removal of volatile impurity molecules may be facilitated. Accordingly, the organic light-emitting device may have improved luminescence efficiency and emission lifespan.

In addition, the heterocyclic compound represented by Formula 1 may have a 4,6-di(1,1'-biphenyl-4-yl)benzo[b,d]furan structure, a 4,6-di(1,1'-biphenyl-4-yl)benzo[b,d]thiophene structure, or a 4,6-di(1,1'-biphenyl-4-yl)benzo[b,d]selenophene structure in the molecular core thereof. By having such a structure, a balance of a LUMO level and carrier mobility of electrons and holes are improved. As a result, distributions of recombination of charges and formation of excitons in a layer containing the heterocyclic compound represented by Formula 1 are dispersed, and the load is also dispersed, thereby improving lifespan of the organic light-emitting device.

Thus, the heterocyclic compound represented by Formula 1 may achieve both a low glass transition temperature and a low amorphousness, which has been difficult to achieve in the past. The heterocyclic compound represented by Formula 1 also achieves an excellent balance between a LUMO level and carrier mobility of electrons and holes. In addition, since the heterocyclic compound represented by Formula 1 has both high solubility and long life of a solution, high efficiency and long lifespan of an organic light-emitting device may be obtained.

Since the heterocyclic compound represented by Formula 1 has only a benzene group or a naphthalene group as a ring-type substituent, volatile impurity molecules may be easily removed in a subsequent solvent drying process.

The heterocyclic compound represented by Formula 1 may be a wide band gap material, since the gap between HOMO and LUMO energy levels may be 3.0 eV or higher.

In addition, since the heterocyclic compound represented by Formula 1 has a substituent represented by $Ar_1$ connected to a biphenyl group in a meta position, solubility is improved by the law of entropy increase due to an increase in the number of conformations of molecules by rotation of a single bond.

In addition, since the heterocyclic compound represented by Formula 1 contains biphenyl groups at two or more positions in a core thereof, the heterocyclic compound may have a LUMO level formed continuously from dibenzofuran, dibenzothiophene, and the like to biphenyl groups by the π-conjugation effect. Thus, high stability for electron injection and highly suitable electron mobility may be achieved.

The heterocyclic compound represented by Formula 1 may be included in an organic layer between a pair of electrodes in an organic light-emitting device. In some embodiments, the heterocyclic compound represented by Formula 1 may be included in an emission layer and be suitable to serve as a host.

The heterocyclic compound represented by Formula 1 may impart high luminescence efficiency and emission lifespan to an organic light-emitting device. The reason is understood that the heterocyclic compound represented by Formula 1 has a low glass transition temperature, and a satisfactory balance between a LUMO level and carrier mobility of electrons and holes, as described above.

Further, precipitation of the heterocyclic compound represented by Formula 1 in a solution may be difficult, and pot life of the solution may be long. Thus, the heterocyclic compound may impart high luminescence efficiency and emission lifespan to an organic light-emitting device, even when a wet deposition method is used.

The heterocyclic compound represented by Formula 1 may be synthesized by any suitable known organic synthetic method. Methods of synthesizing the heterocyclic compound represented by Formula 1 should be readily apparent to those of ordinary skill in the art by referring to Examples described herein.

Composition

Hereinafter, a composition according to an exemplary embodiment will be described in detail.

The composition may include at least one heterocyclic compound represented by Formula 1 described above.

The heterocyclic compound represented by Formula 1 may be included in an organic layer between a pair of electrodes in an organic light-emitting device. In some embodiments, the heterocyclic compound represented by Formula 1 may be included in an emission layer and be suitable to serve as a host.

The heterocyclic compound represented by Formula 1 may impart high luminescence efficiency and emission lifespan to an organic light-emitting device. The reason is understood that the heterocyclic compound represented by Formula 1 has a low glass transition temperature, and a satisfactory balance between a LUMO level and carrier mobility of electrons and holes, as described above.

Further, precipitation of the heterocyclic compound in a solution may be difficult, and pot life of the solution may be long. Thus, the heterocyclic compound may impart high luminescence efficiency and emission lifespan to an organic light-emitting device, even when a wet deposition method is used.

In some embodiments, the composition may further include a first compound including a carbazole-based moiety.

In some embodiments, the composition may further include a second compound including an azine-based moiety.

In some embodiments, the composition may further include a luminescent material.

In some embodiments, the composition may further include at least one of a first compound containing a carbazole-based moiety, a second compound containing an azine-based moiety, and a luminescent material.

In some embodiments, in the composition, a content of the heterocyclic compound represented by Formula 1 may be in a range of about 5 percent by weight (wt %) to about 95 wt % relative to the total weight of the composition, for example, about 10 wt % to about 90 wt %, or for example, about 20 wt % to about 80 wt %.

Within this range, the solubility of the heterocyclic compound represented by Formula 1 is further improved, and precipitation is less likely to occur in the solution, resulting in a longer pot life of the solution. Accordingly, the organic light-emitting device may have improved luminescence efficiency and emission lifespan.

Hereinafter, the luminescent material, the first compound, and the second compound will be described in detail.

As described above, the first compound may include a carbazole moiety. That is, the composition according to the embodiment may include a compound containing a carbazole moiety to further enhance suppression of molecule aggregation and also to improve balance of carrier mobility between electrons and holes. Within this range, the solubility of the composition is further improved, and precipitation is less likely to occur in the solution, resulting in a longer pot life of the solution. Accordingly, the organic light-emitting device may have further improved luminescence efficiency and emission lifespan. The first compound may be represented by the following Formula 5.

As described above, the second compound may include an azine moiety, the second compound may be represented by the following Formula 6.

In some embodiments, the composition may further include at least one of a first compound represented by Formula 5 and a second compound represented by Formula 6:

Formula 5

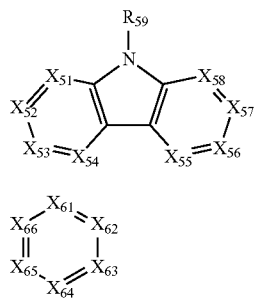

Formula 6 wherein, in Formulae 5 and 6, $X_{51}$ may be N or $C(R_{51})$, $X_{52}$ may be N or $C(R_{52})$, $X_{53}$ may be N or $C(R_{53})$, $X_{54}$ may be N or $C(R_{54})$, $X_{55}$ may be N or $C(R_{55})$, $X_{56}$ may be N or $C(R_{56})$, $X_{57}$ may be N or $C(R_{57})$, $X_{58}$ may be N or $C(R_{58})$, $X_{61}$ may be N or $C(R_{61})$, $X_{62}$ may be N or $C(R_{62})$, $X_{63}$ may be N or $C(R_{63})$, $X_{64}$ may be N or $C(R_{64})$, $X_{65}$ may be N or $C(R_{65})$, $X_{66}$ may be N or $C(R_{66})$, provided that at least one of $X_{61}$ to $X_{66}$ may be N, $R_{51}$ to $R_{58}$ and $R_{61}$ to $R_{66}$ may each independently be hydrogen, deuterium, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, $R_{59}$ may be a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, and at least one of $R_{61}$ to $R_{66}$ may be a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

In some embodiments, in Formulae 5 and 6, two adjacent groups among $R_{51}$ to $R_{58}$ and $R_{61}$ to $R_{66}$ may optionally be bound to form a ring, but embodiments are not limited thereto.

In some embodiments, the first compound may be at least one of compounds represented by Formulae H1-1 to H1-13, H2-1 to H2-34, and H3-1 to H3-3:

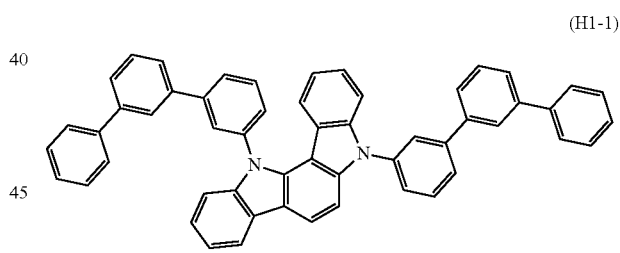
(H1-1)

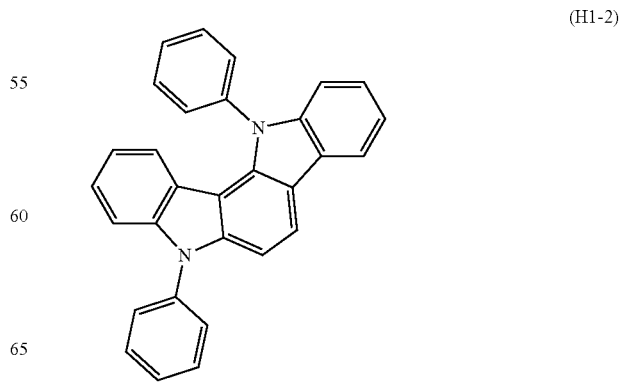
(H1-2)

(H1-3)
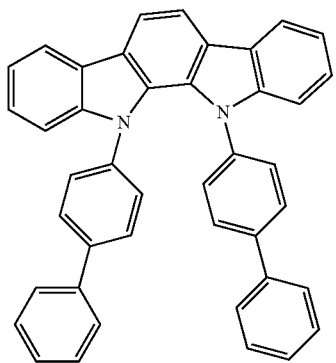
(H1-4)
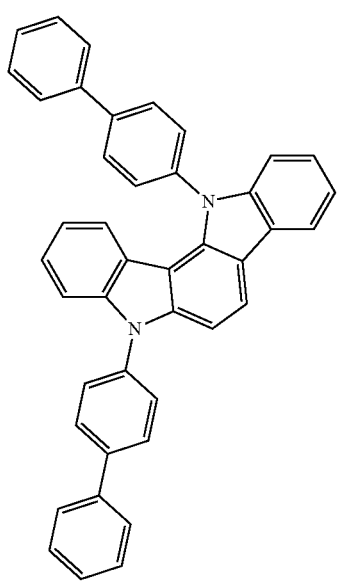
(H1-5)
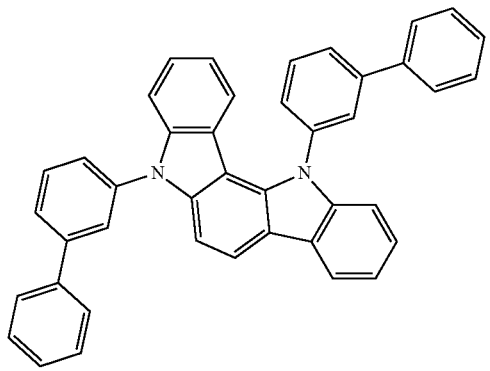
(H1-6)
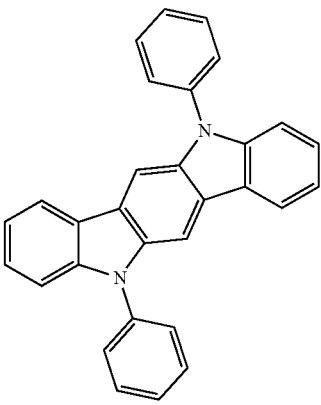
(H1-7)
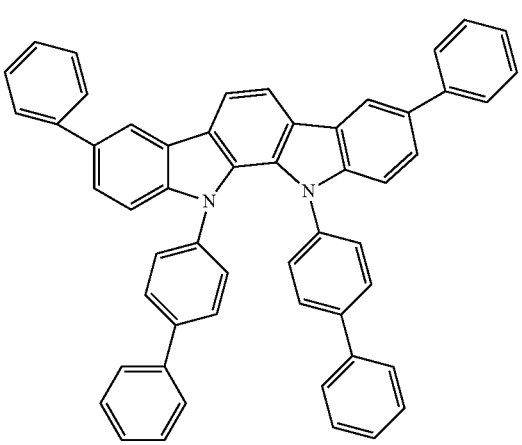
(H1-8)
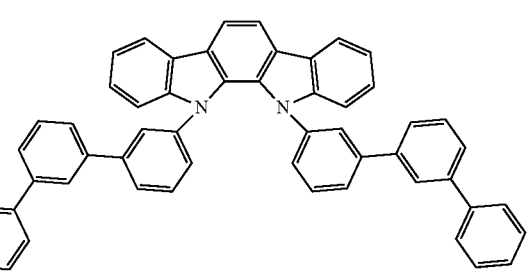
(H1-9)
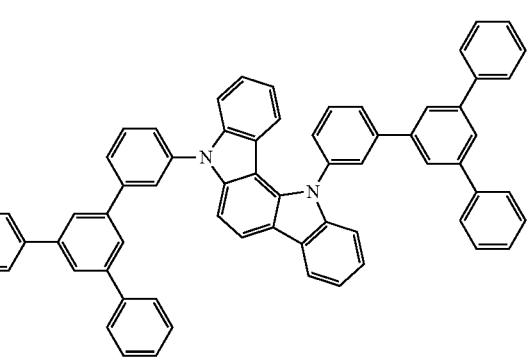

(H1-10)
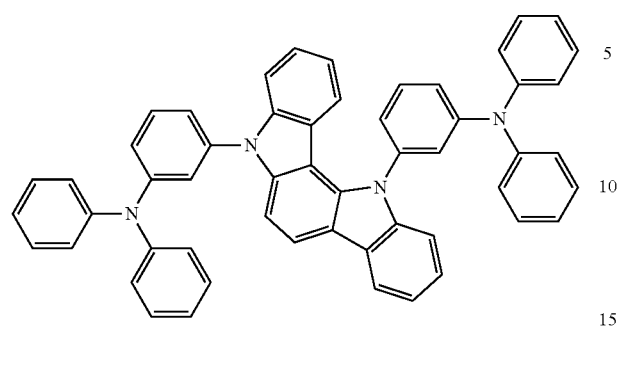
(H1-13)
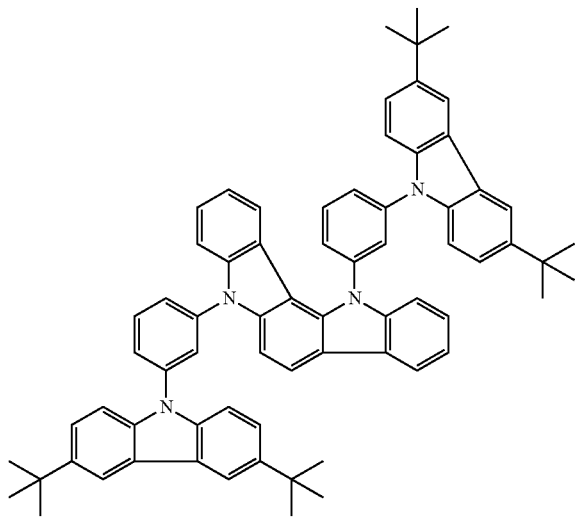
(H1-11)
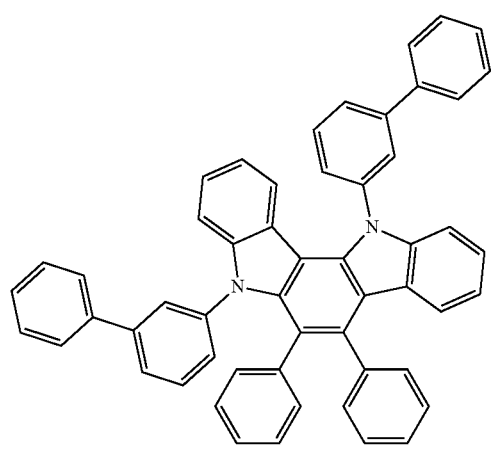
(H2-1)
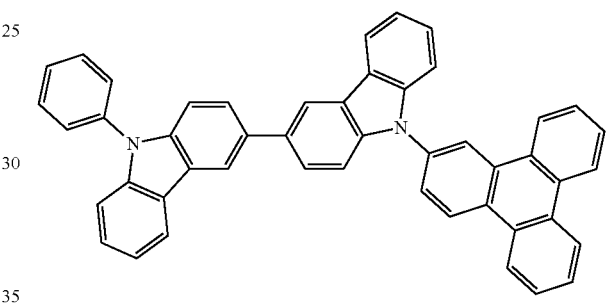
(H2-2)
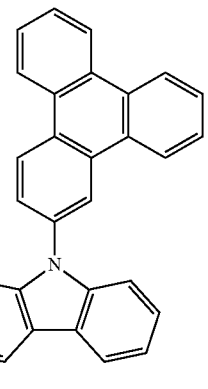
(H1-12)
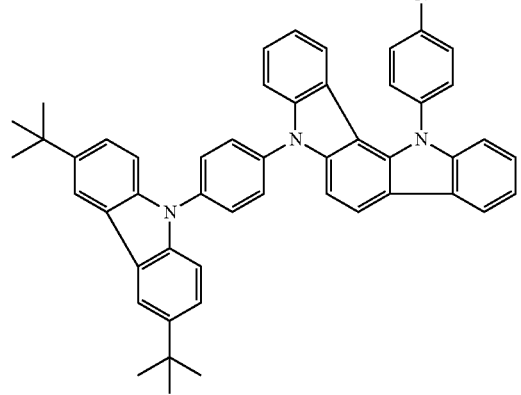
(H2-3)
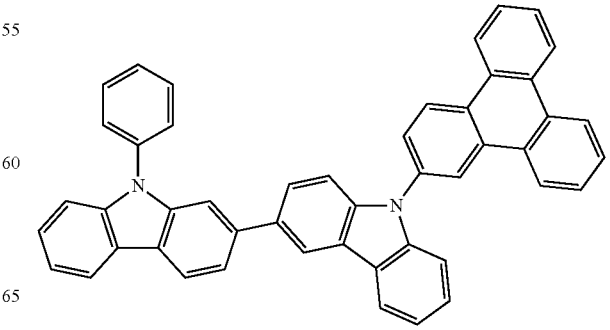

(H2-4)
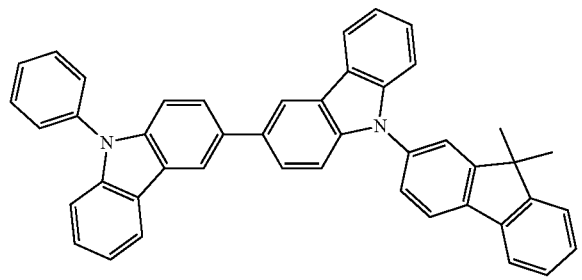
(H2-5)
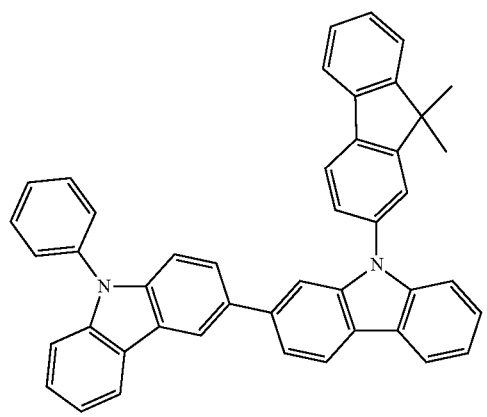
(H2-6)
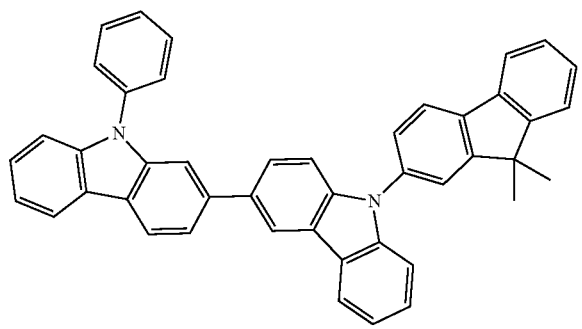
(H2-7)
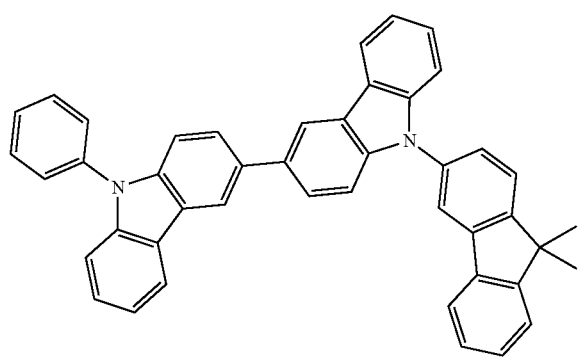
(H2-8)
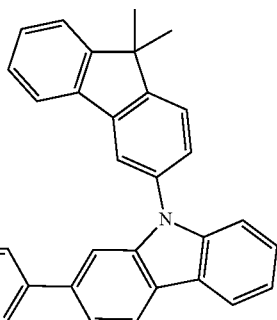
(H2-9)
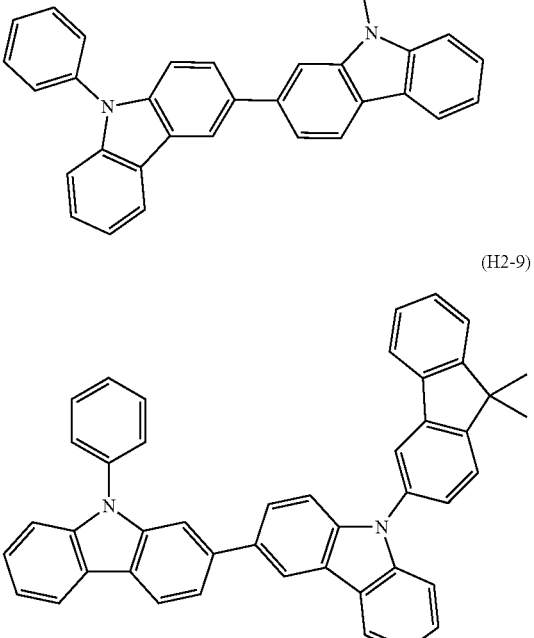
(H2-10)
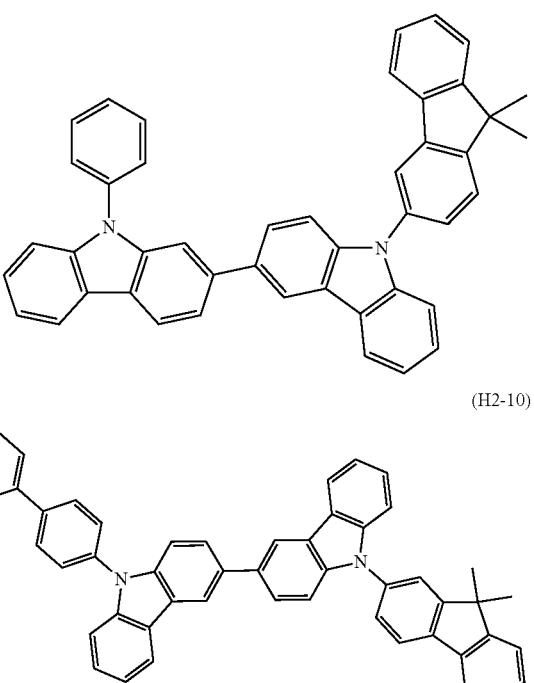
(H2-11)
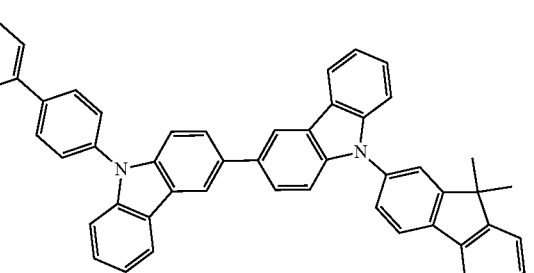

(H2-12)
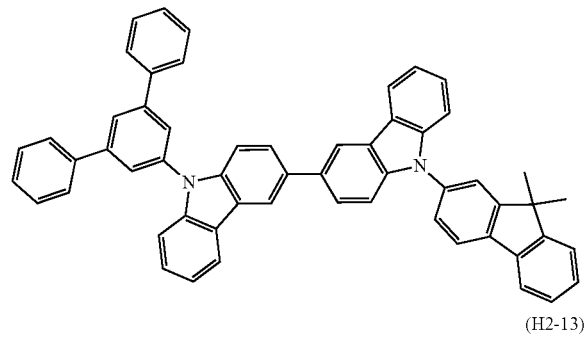
(H2-13)
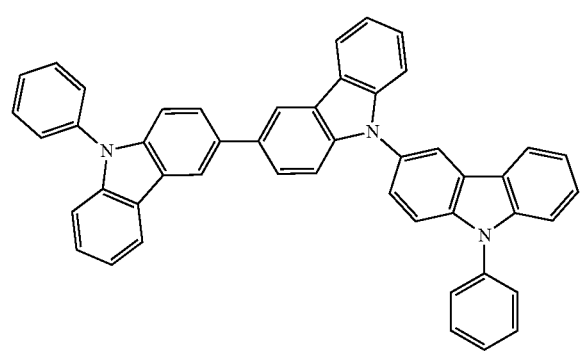
(H2-14)
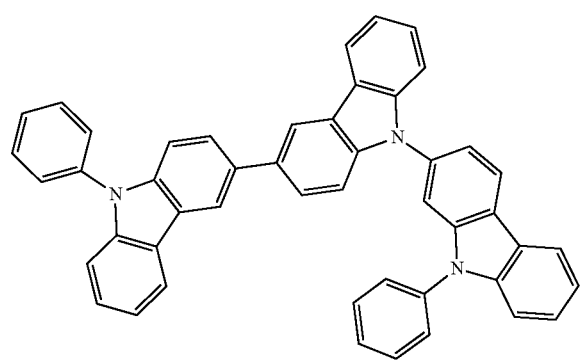
(H2-13)
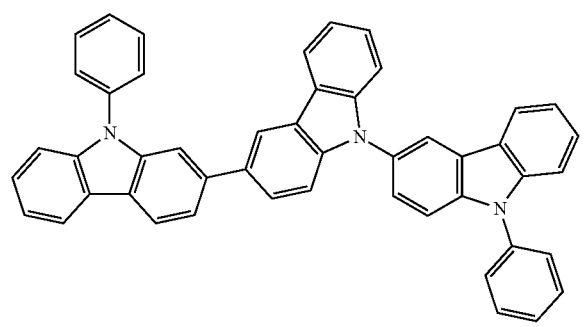
(H2-15)
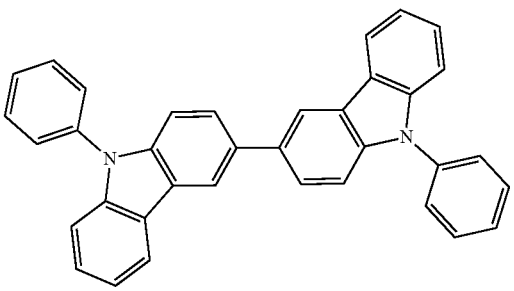
(H2-16)
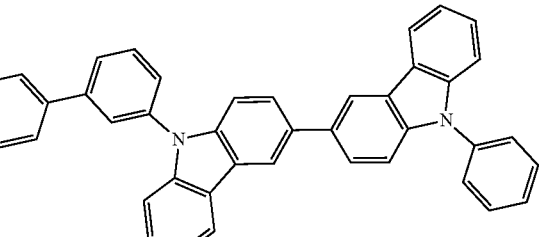
(H2-17)
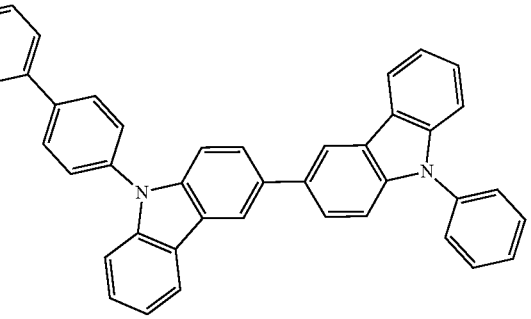
(H2-18)
(H2-19)
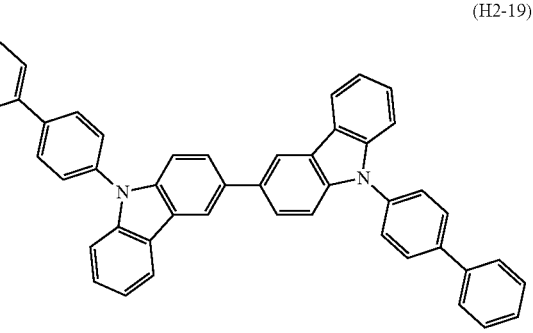

(H2-20)
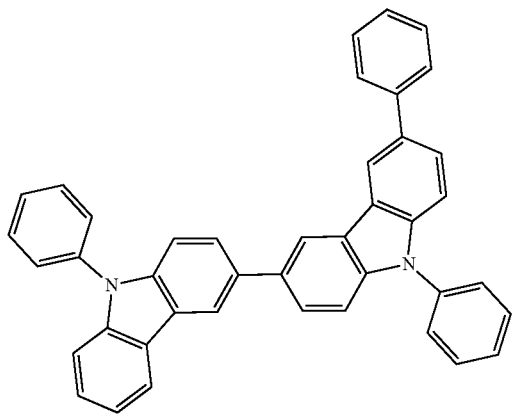
(H2-21)
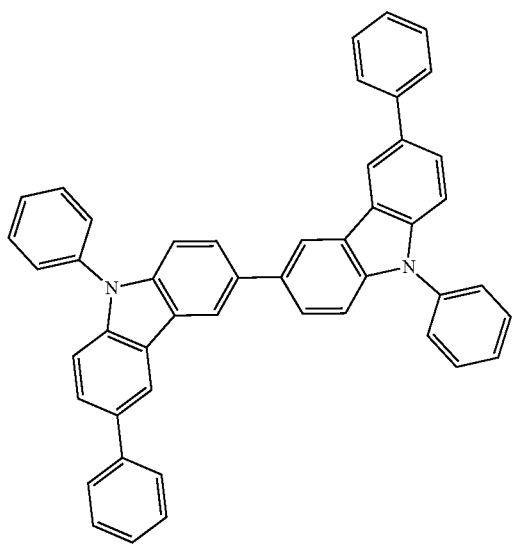
(H2-22)
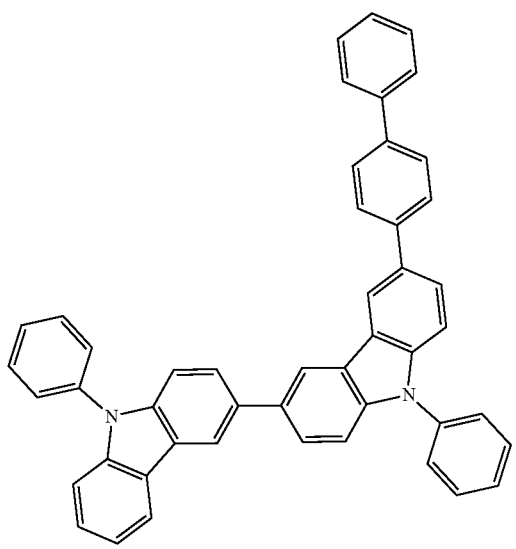
(H2-23)
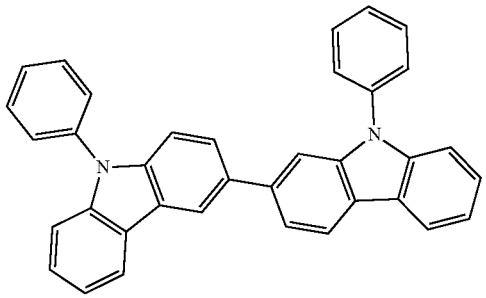
(H2-24)
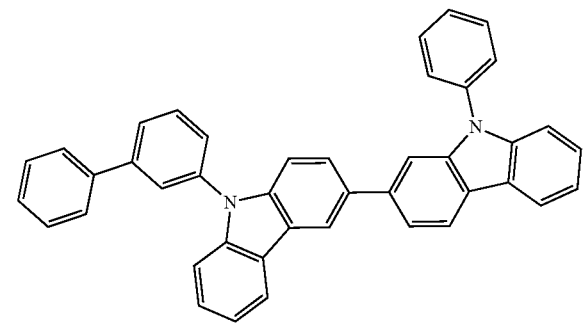
(H2-25)
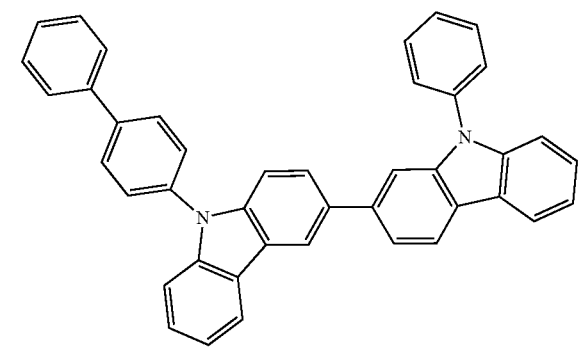
(H2-26)
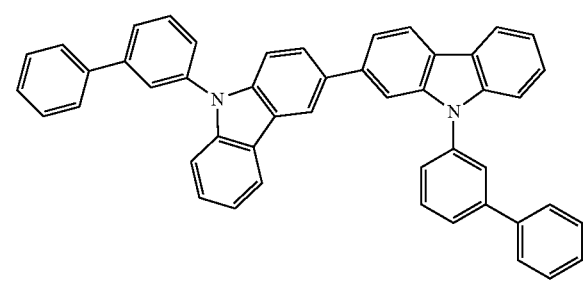

(H2-27)
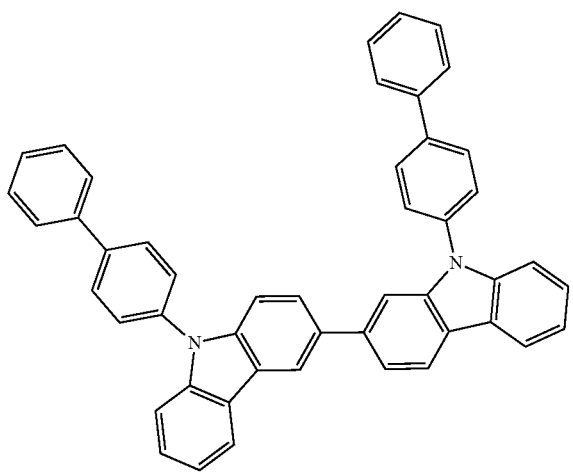
(H2-28)
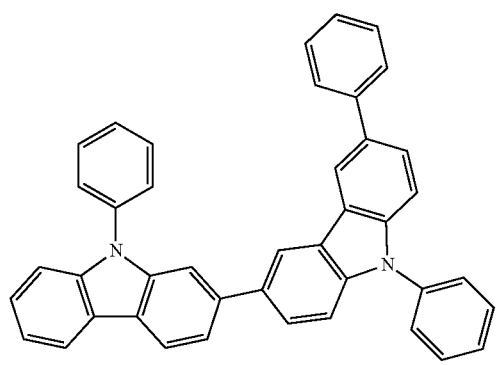
(H2-29)
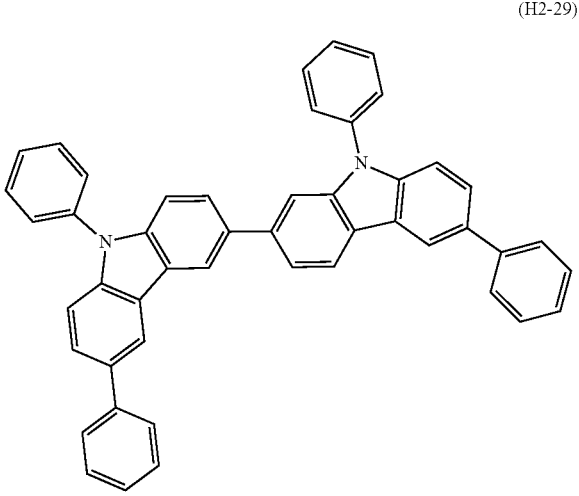
(H2-30)
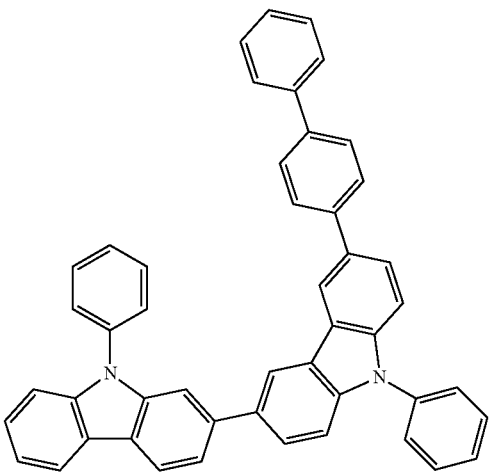
(H2-31)
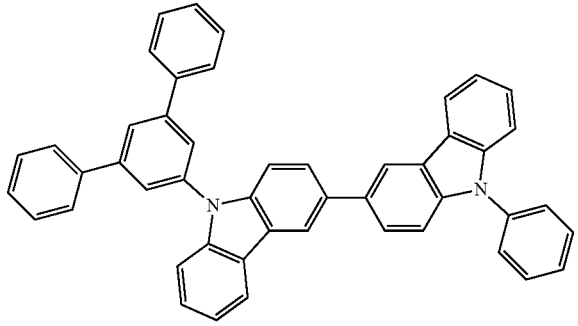
(H2-32)
(H2-33)
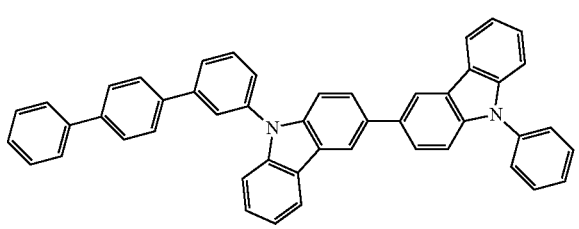

(H2-34)
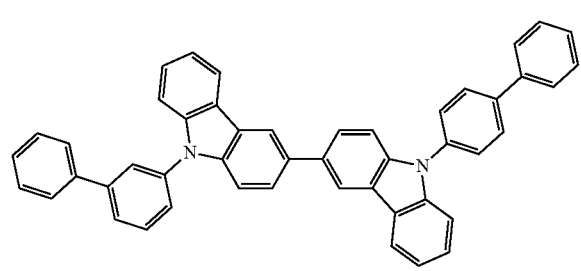
(H3-1)
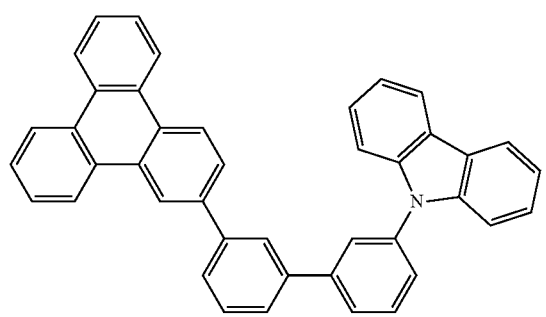
(H3-2)
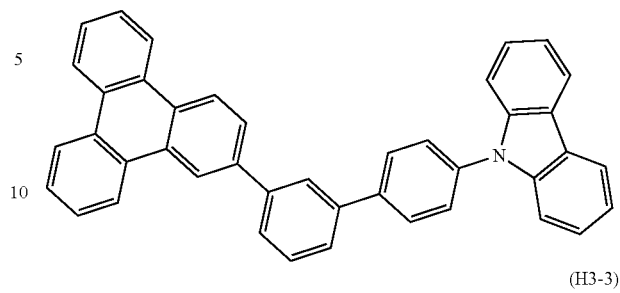
(H3-3)
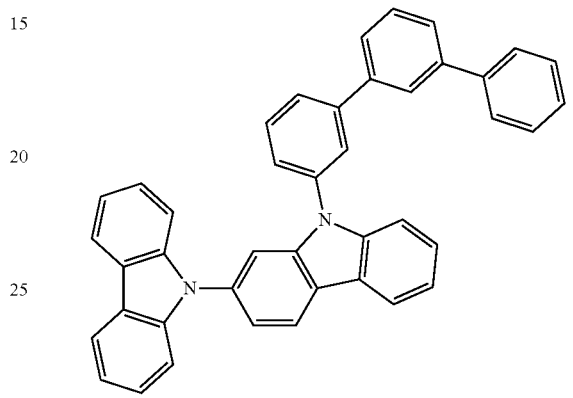
In some embodiments, the second compound may be compounds represented by Formulae Az1 to Az38:
Az1
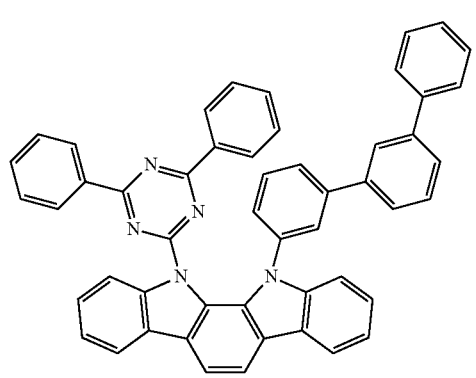
Az2
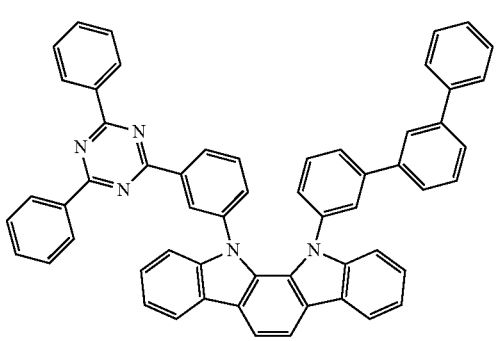
Az3
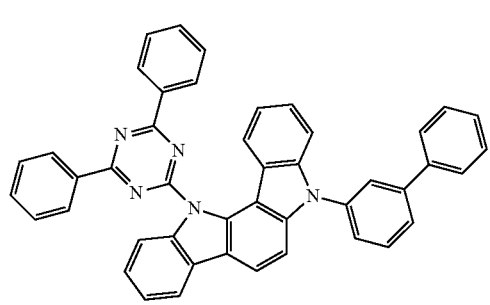
Az4
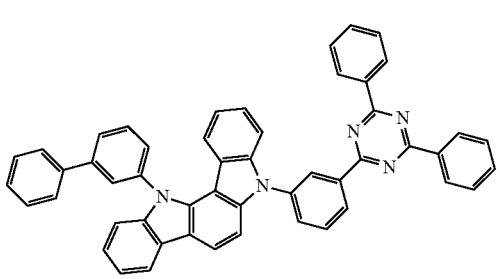

-continued
Az5
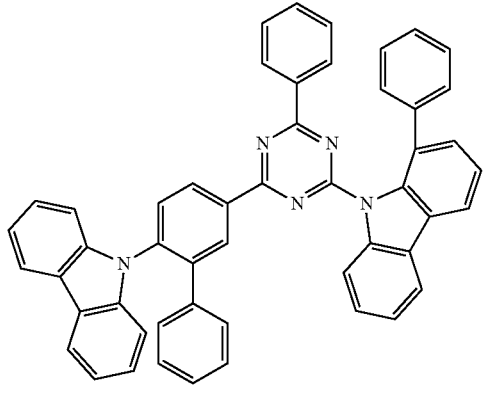
Az6
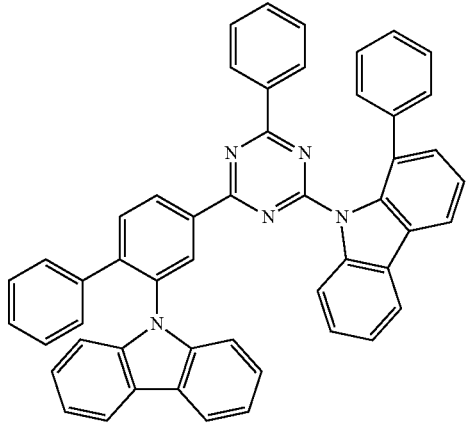
Az7
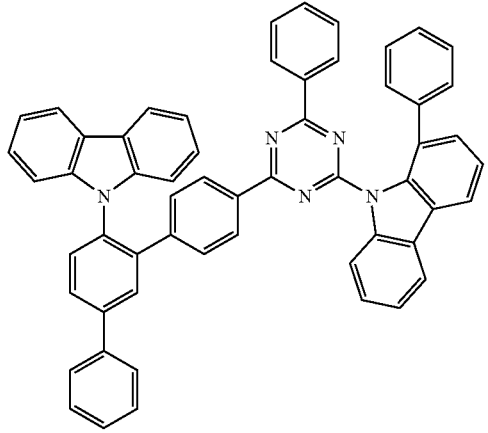
Az8
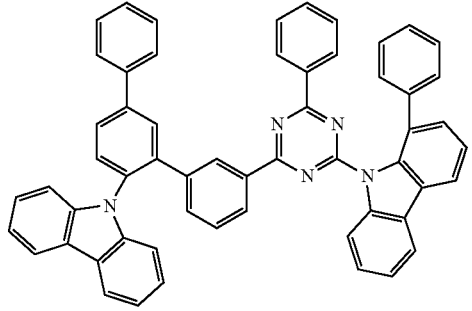
Az9
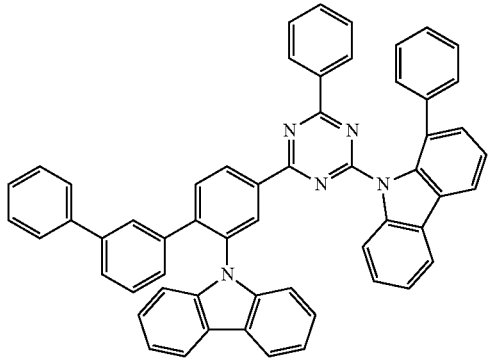
Az10
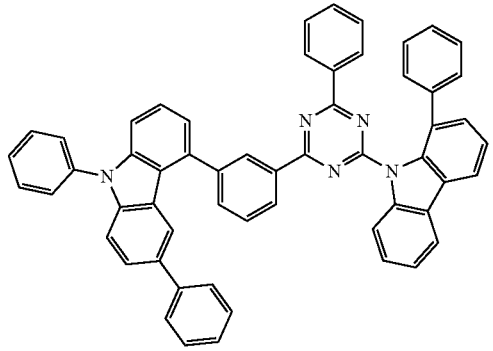

-continued
Az11
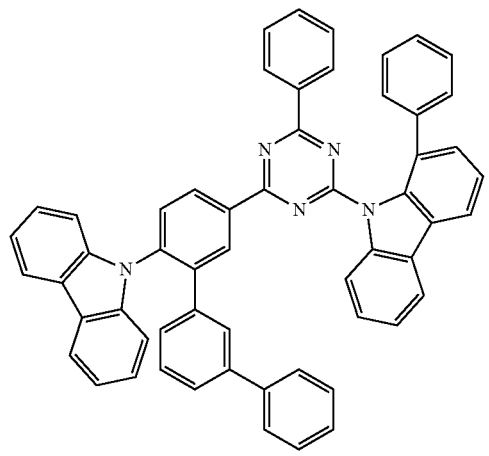
Az12
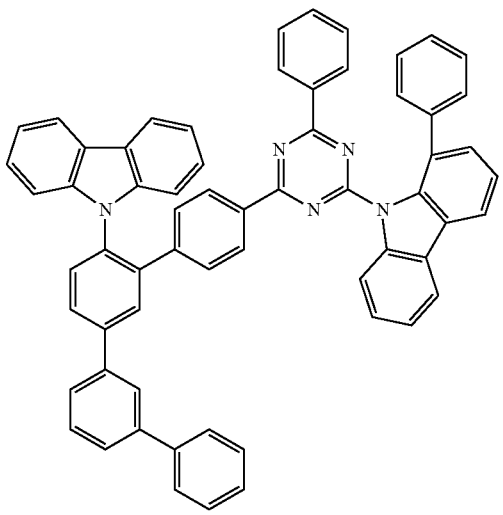
Az13
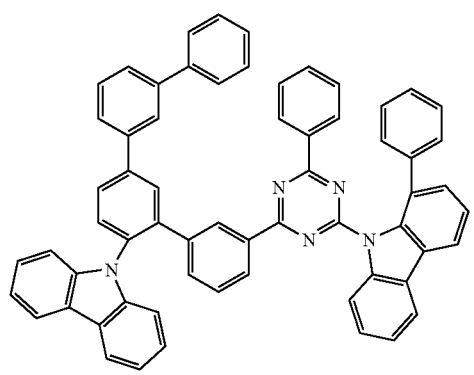
Az14
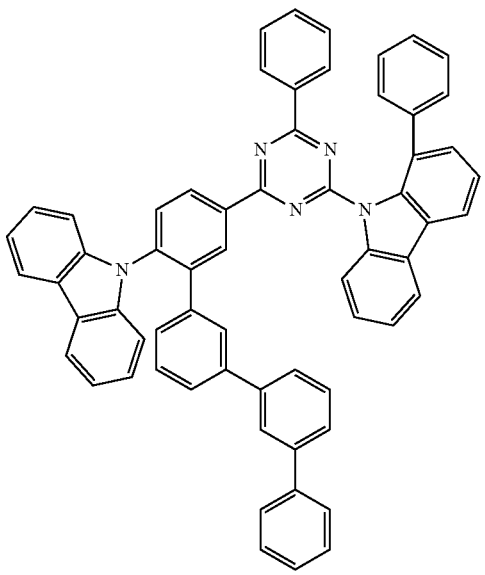
Az15
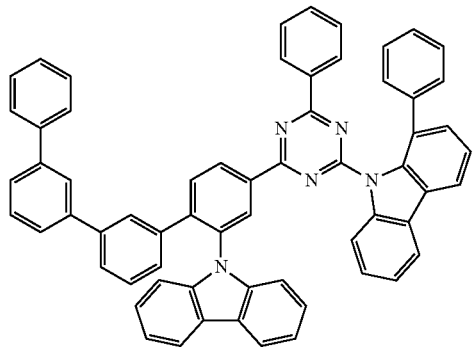
Az16
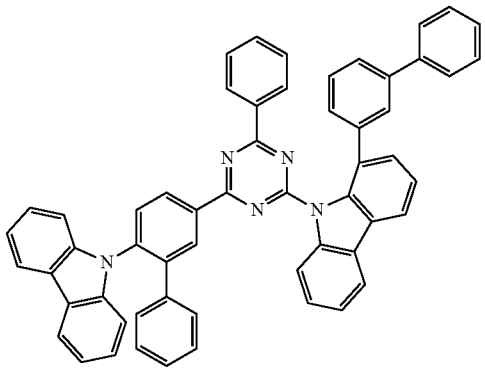

-continued
Az17
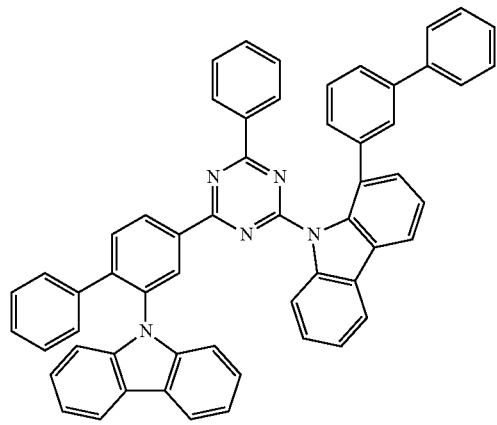
Az18
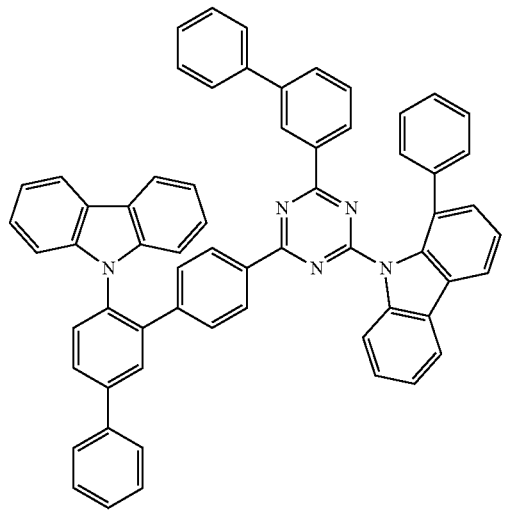
Az19
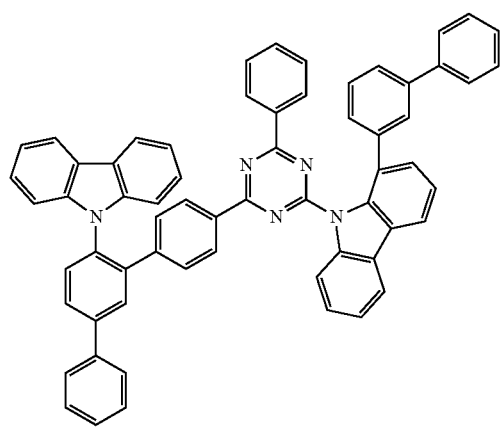
Az20
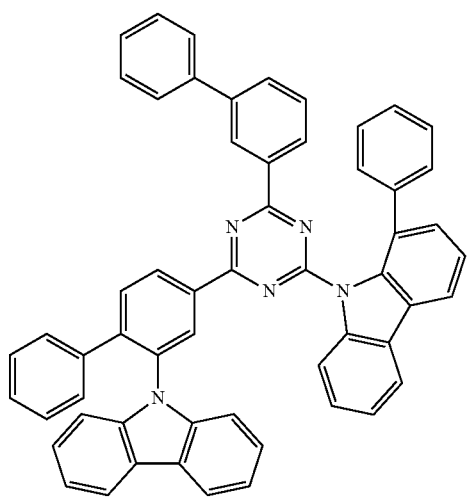
Az21
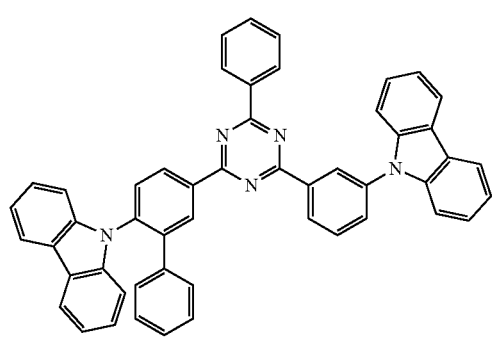
Az22
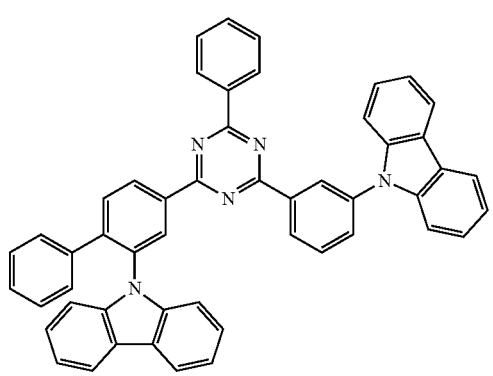

-continued
Az23
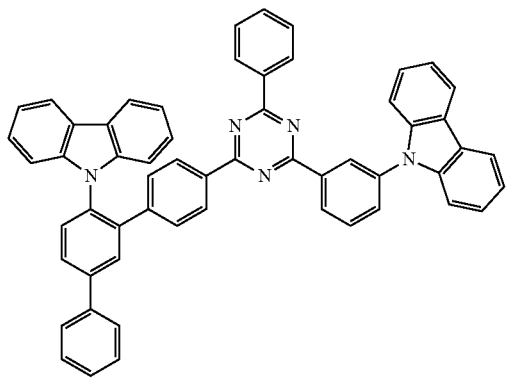
Az24
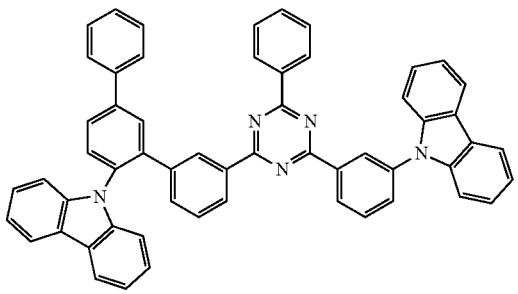
Az25
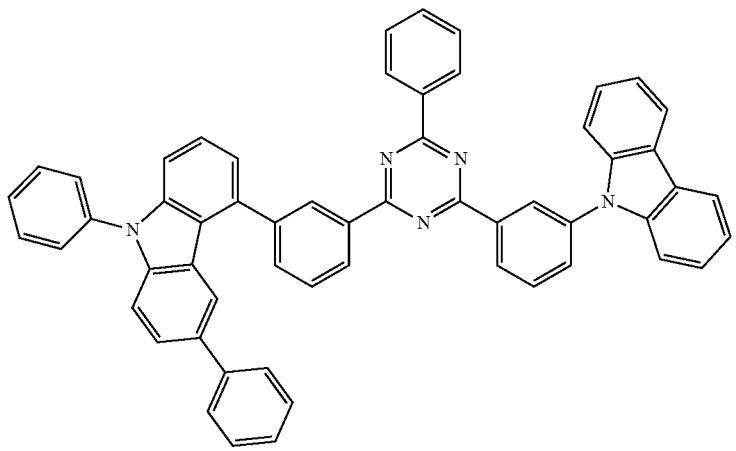
Az26
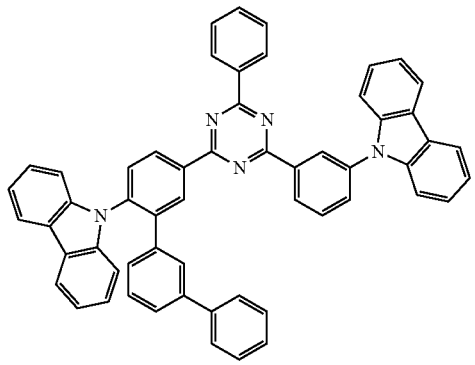
Az27
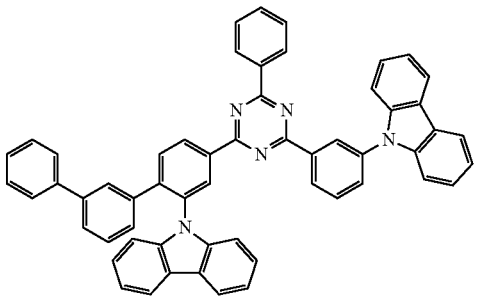
Az28
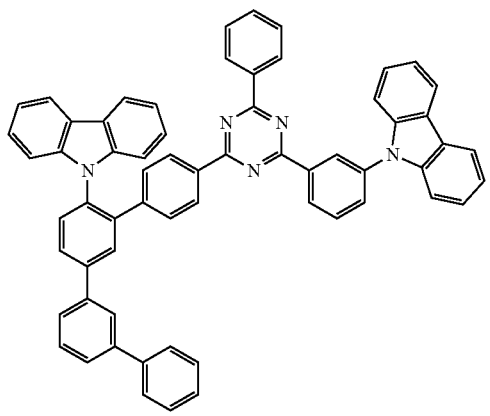
Az29
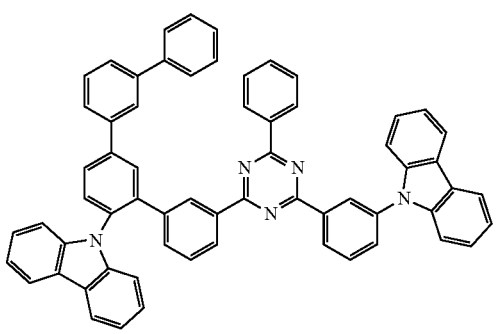

Az30
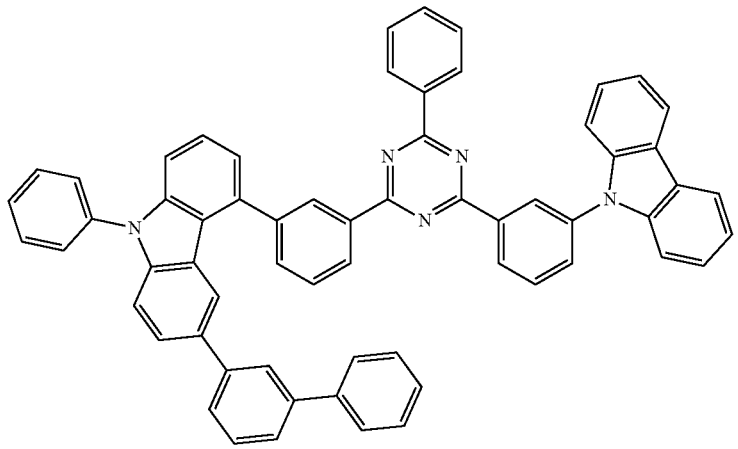
Az31
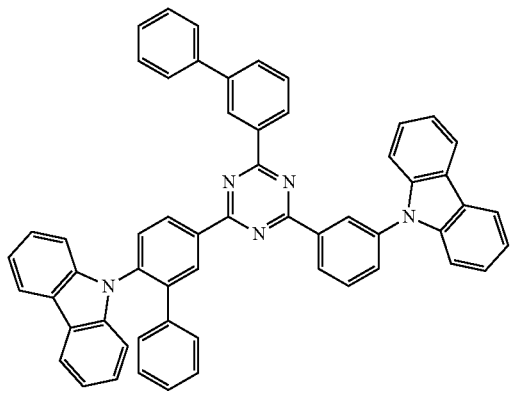
Az32
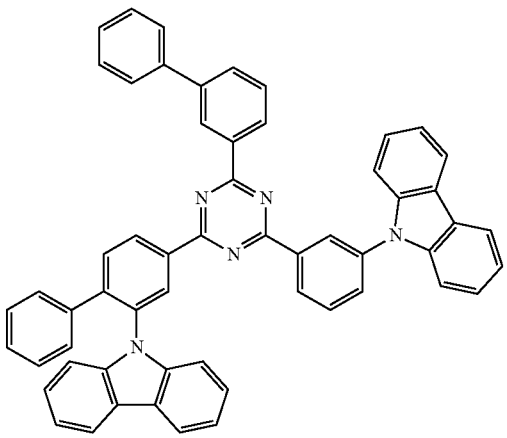
Az33
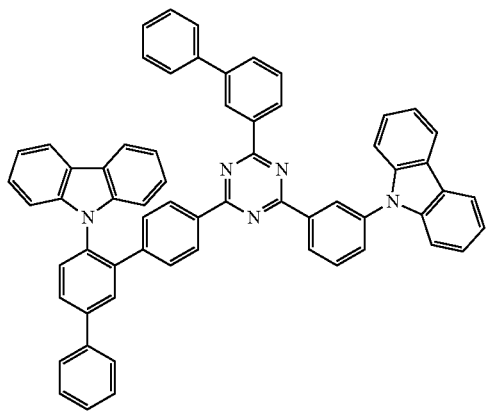
Az34
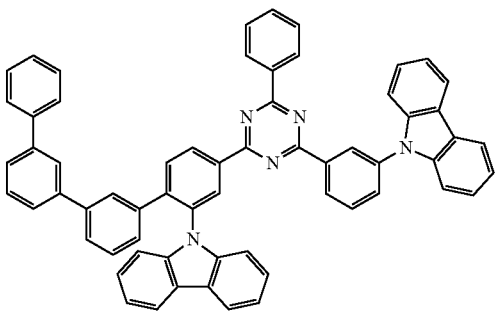
Az35
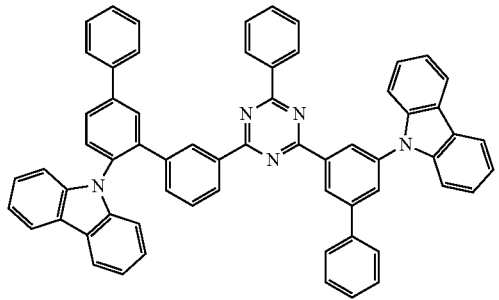
Az36
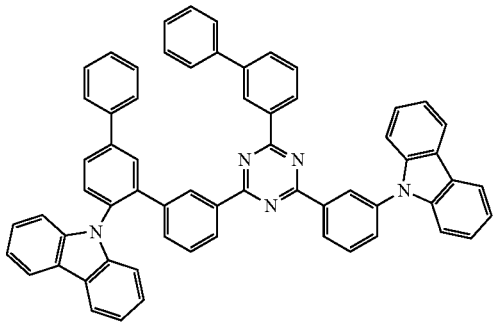

Az37

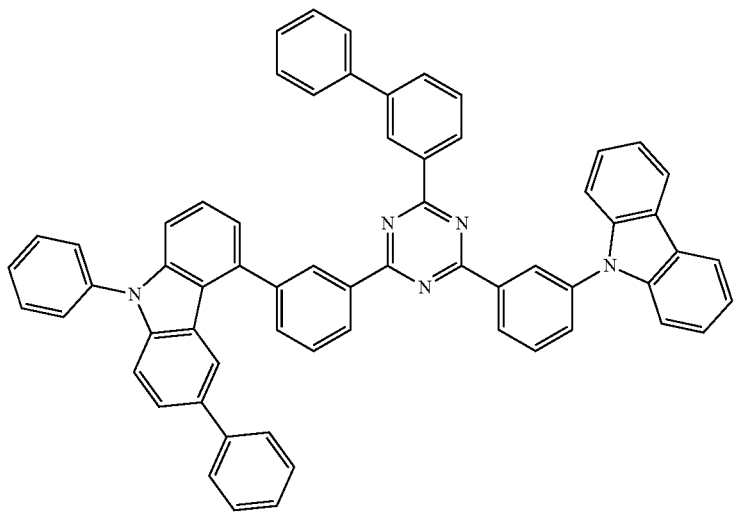

Az38

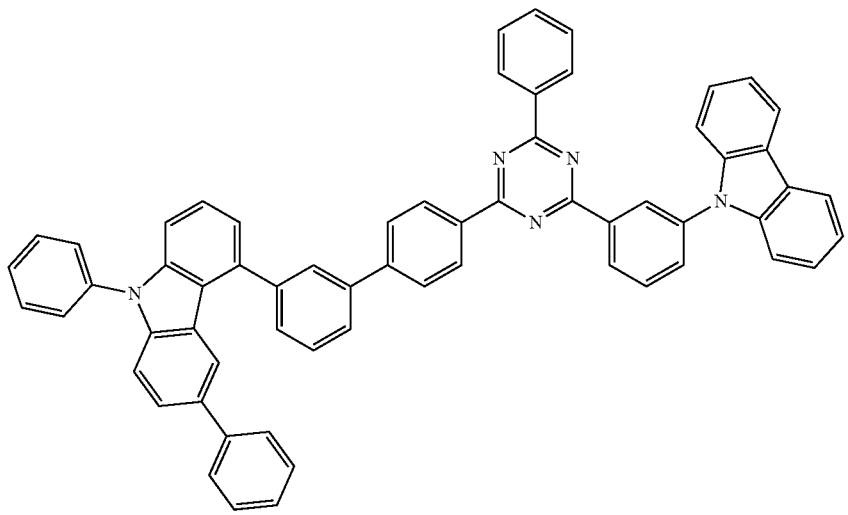

The first compound may have the lowest HOMO energy level except for the luminescent material (dopant) among the compounds included in the composition. Thus, the first compound may have high hole injectability and/or hole transportability.

Accordingly, by adjusting the ratio of the first compound in the composition, it is possible to control the hole injectability and/or hole transportability of the composition. Thus, a hole density profile according to a number of holes in the emission layer and a thickness direction of the emission layer of the organic light-emitting device employing the composition may be easily controlled.

When the composition further includes the first compound, a difference ($\Delta$HOMO, a hole trap depth) between a HOMO energy level ($HOMO_0$) of the heterocyclic compound represented by Formula 1 and a HOMO energy level ($HOMO_{Cz}$) of the first compound may be calculated by Mathematical Equation 1. Here, $HOMO_0$ and $HOMO_{Cz}$ are each a negative number.

$$\Delta HOMO = HOMO_{Cz} - HOMO_0 \quad \text{Mathematical Equation 1}$$

$\Delta$HOMO may be, for example, about 0.05 eV to about 1.0 eV, for example, about 0.10 eV to about 0.8 eV, or for example, about 0.15 eV to about 0.7 eV.

FIG. 1 is a diagram for illustrating an exemplary energy level relationship between the heterocyclic compound represented by Formula 1 and a first compound containing a carbazole group in a composition according to one or more embodiments. Referring to FIG. 1, a desirable relationship between $HOMO_0$ and $HOMO_{Cz}$ may be known. Within the above range, an organic light-emitting device may have further improved luminescence efficiency and emission lifespan.

The second compound may have the deepest LUMO energy level among the compounds included in the composition. Thus, the second compound may have high electron injectability and/or electron transportability.

Accordingly, by adjusting the ratio of the second compound in the composition, it is possible to control the electron injectability and/or electron transportability of the composition. Thus, an electron density profile according to an amount of electrons in the emission layer and a thickness direction of the emission layer of the organic light-emitting device employing the composition may be easily controlled.

When the composition further includes the second compound, a difference ($\Delta$LUMO, an electron trap depth) between a LUMO energy level ($LUMO_0$) of the heterocyclic compound represented by Formula 1 and a LUMO energy level (LUMO$_{Azine}$) of the second compound may be calculated by Mathematical Equation 2. Here, LUMO$_0$ and LUMO$_{Azine}$ are each a negative number.

$$\Delta LUMO = LUMO_0 - LUMO_{azine} \qquad \text{Mathematical Equation 2}$$

ΔLUMO may be, for example, about 0.05 eV to about 1.0 eV, for example, about 0.05 eV to about 0.5 eV, or for example, about 0.05 eV to about 0.3 eV.

Figure 2:
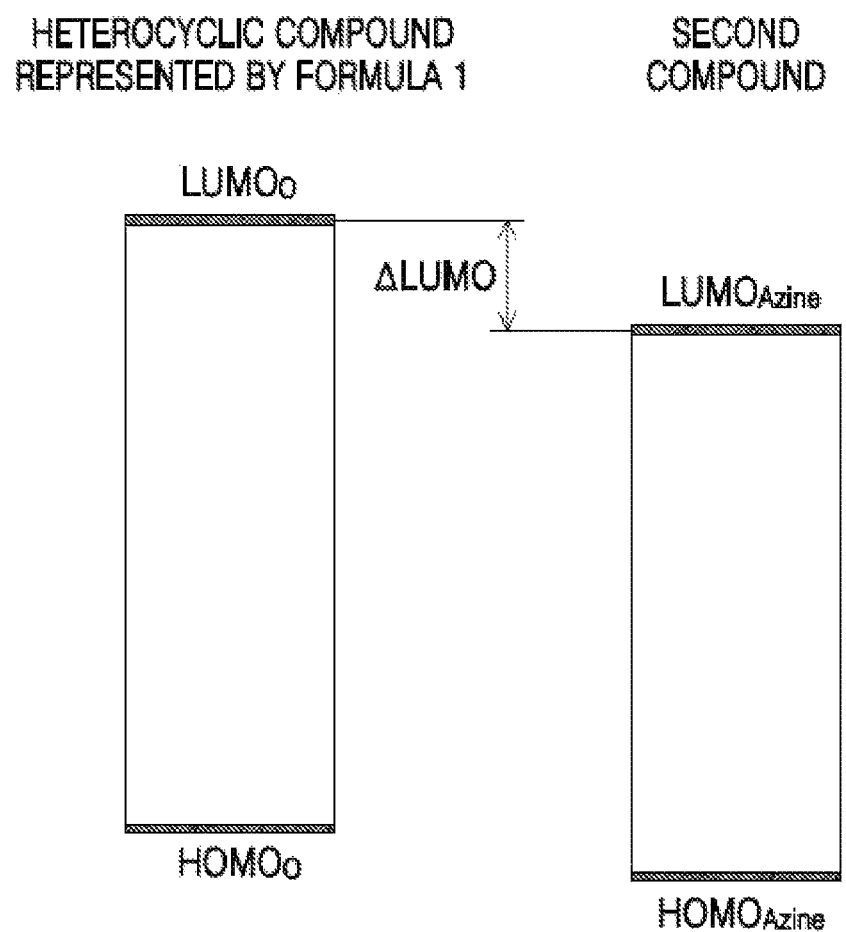
FIG. 2 is a diagram for illustrating an exemplary energy level relationship between the heterocyclic compound represented by Formula 1 and a second compound containing an azine group in a composition according to one or more embodiments.

FIG. 2 is a diagram for illustrating an exemplary energy level relationship between the heterocyclic compound represented by Formula 1 and a second compound containing an azine group in a composition according to one or more embodiments. Referring to FIG. 2, a desirable relationship between LUMO$_0$ and LUMO$_{azine}$ may be known. Within the above range, an organic light-emitting device may have further improved luminescence efficiency and emission lifespan.

When the composition includes the heterocyclic compound represented by Formula 1 and the first compound, the composition may have improved hole injectability and/or hole transportability, and the composition may be used in a hole injection layer, a hole transport layer, and/or an emission layer of an organic light-emitting device.

When the composition includes the heterocyclic compound represented by Formula 1 and the second compound, the composition may have improved electron injectability and/or electron transportability, and the composition may be used in an electron injection layer, an electron transport layer, and/or an emission layer of an organic light-emitting device.

When the composition includes the heterocyclic compound represented by Formula 1 and the first and second compounds, the composition may have improved hole injectability, hole transportability, electron injectability, and/or electron transportability, and the composition may be used in a hole injection layer, a hole transport layer, an electron injection layer, an electron transport layer, and/or an emission layer of an organic light-emitting device.

In some embodiments, the composition may include the first compound and the second compound, but embodiments are not limited thereto. When the composition includes the first compound and the second compound together, controlling of holes and controlling of electrons may each be independently performed. Thus, optimizing performance of an organic light-emitting device employing such a composition may be convenient.

The composition may further include a luminescent material.

The luminescent material is not particularly limited as long as the luminescent material may emit light. For example, the luminescent material may be a fluorescent dopant, a phosphorescent dopant, a quantum dot, or the like.

The fluorescent dopant may be a compound that may emit light from singlet excitons. The fluorescent dopant may be, for example, perylene and a derivative thereof, rubrene and a derivative thereof, coumarin and a derivative thereof, 4-(dicyanomethylene)-2-(p-dimethylaminostyryl)-6-methyl-4H-pyran (DCM) and a derivative thereof, or any combination thereof, or the like, but embodiments are not limited thereto.

The phosphorescent dopant may be a compound that may emit light from triplet excitons, and for example, the phosphorescent dopant may be an organometallic compound. For example, the phosphorescent dopant may be an iridium complex such as bis[2-(4,6-difluorophenyl)pyridinate] picolinate iridium (Ill) (Flrpic), bis(1-phenylisoquinoline) (acetylacetonate) iridium (Ill) (Ir(piq)$_2$(acac)), tris(2-phenylpyridine) iridium (III) (Ir(ppy)$_3$), and tris(2-(3-p-xylyl) phenylpyridine) iridium(III), an osmium complex, a platinum complex, or the like, but embodiments are not limited thereto, In some embodiments, the phosphorescent dopant may be a phosphorescence-emitting platinum group metal complex. The platinum group metal may collectively include ruthenium (Ru), rhodium (Rh), palladium (Pd), osmium (Os), iridium (Ir), platinum (Pt), or any combination thereof. A phosphorescence-emitting iridium (Ir) complex and a platinum (Pt) complex may be preferable.

For example, the phosphorescent dopant may have at least one ligand of Formulae L1 to L17:

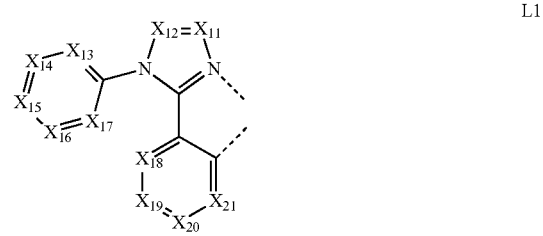

L1

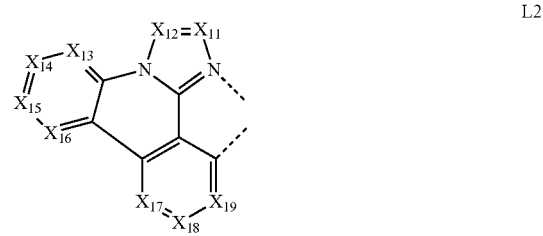

L2

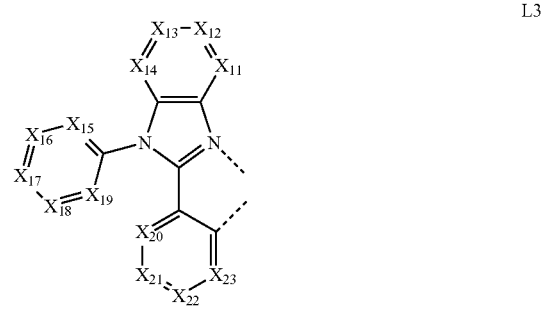

L3

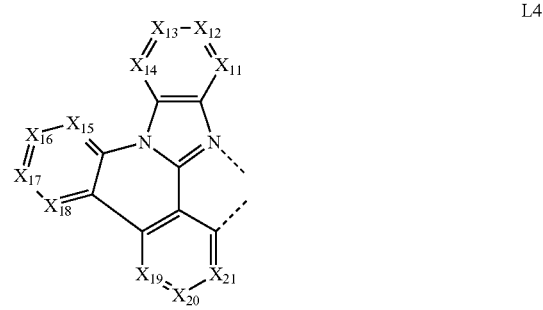

L4

-continued
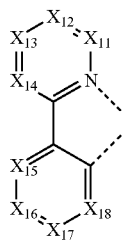
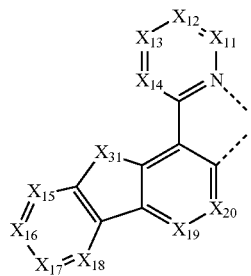
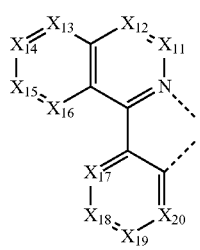
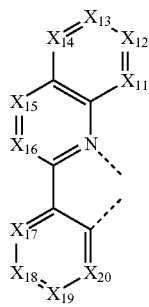
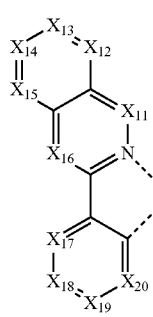
-continued
L5
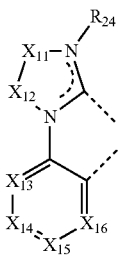
L6
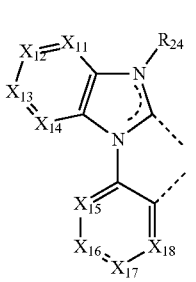
L7
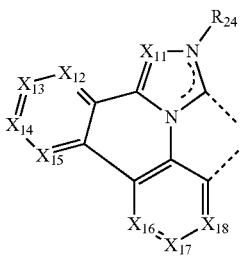
L8
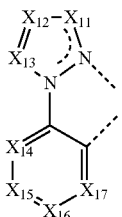
L9
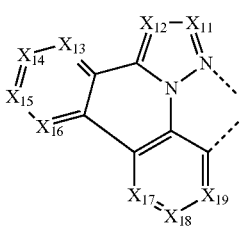
L10
L11
L12
L13
L14
L15
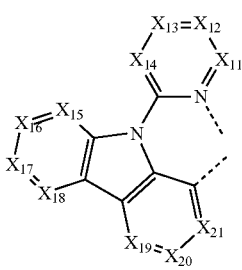

L16

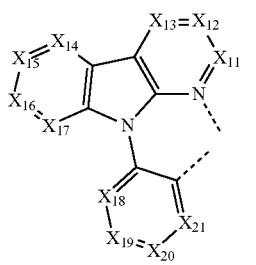

L17

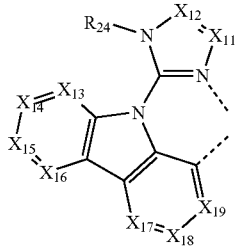

wherein, in Formulae L1 to L17, $X_{11}$ to $X_{23}$ may each independently be $C(R_{21})$ or N, $X_{31}$ may be $B(R_{22})$, $N(R_{22})$, $P(R_{22})$, O, S, Se, C=O, S=O, $SO_2$, $C(R_{22})(R_{23})$, $Si(R_{22})(R_{23})$, or $Ge(R_{22})(R_{23})$, $R_{21}$ to $R_{24}$ may each independently be a hydrogen atom, a deuterium atom, a halogen atom, a substituted or unsubstituted $C_1$-$C_{60}$ alkyl group, a substituted or unsubstituted $C_3$-$C_{60}$ cycloalkyl group, a substituted or unsubstituted $C_1$-$C_{60}$ heteroalkyl group, a substituted or unsubstituted $C_7$-$C_{60}$ arylalkyl group, a substituted or unsubstituted $C_1$-$C_{60}$ alkoxy group, a substituted or unsubstituted $C_6$-$C_{60}$ aryloxy group, an amino group, a silyl group, a substituted or unsubstituted $C_2$-$C_{60}$ alkenyl group, a substituted or unsubstituted $C_3$-$C_{60}$ cycloalkenyl group, a substituted or unsubstituted $C_2$-$C_{60}$ hetero alkenyl group, a substituted or unsubstituted $C_2$-$C_{60}$ alkynyl group, a substituted or unsubstituted $C_6$-$C_{60}$ aryl group, a substituted or unsubstituted $C_1$-$C_{60}$ heteroaryl group, an acyl group, a carbonyl group, a carboxylic acid group, an ester group; a nitrite group, an isonitrile group, a sulfanyl group, a sulfinyl group, a sulfonyl group, a phosphine group, or any combination thereof, and at least two of groups $R_{21}$ to $R_{24}$ may be condensed or bound to form a ring.

In some embodiments, the phosphorescent dopant may be a compound represented by Formulae D1 to D143:

D1

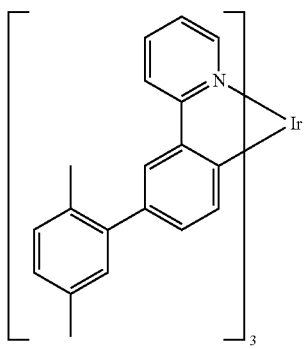

D2

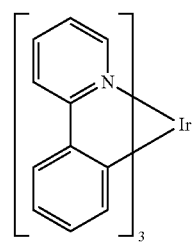

D3

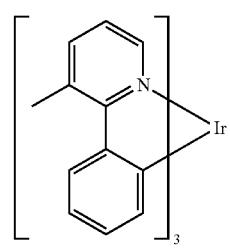

D4

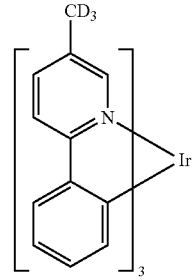

D5

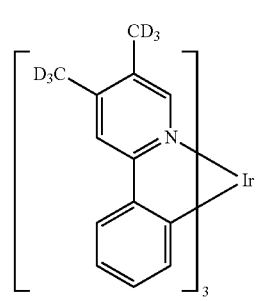

D6

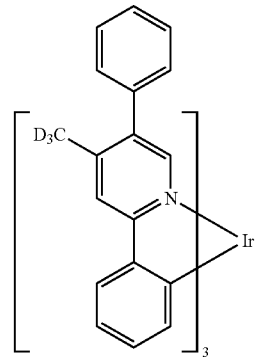

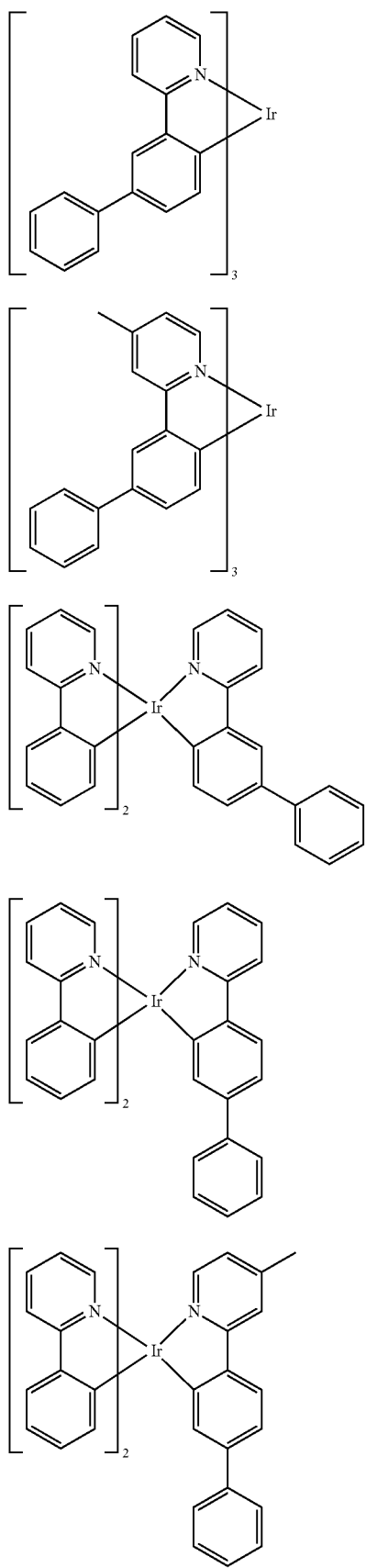
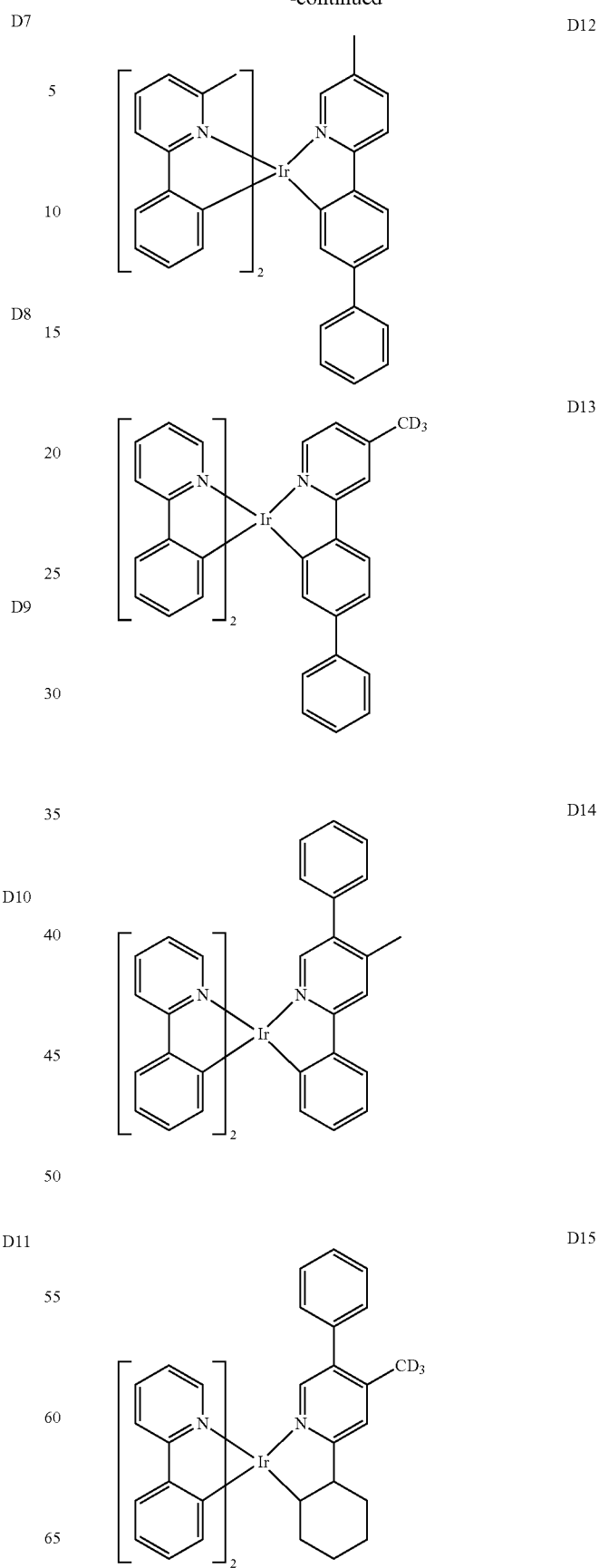

D16 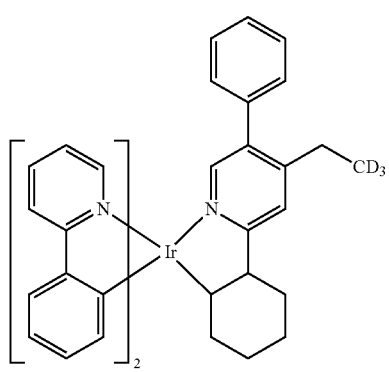
D17 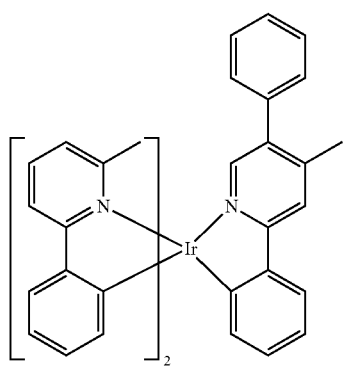
D18 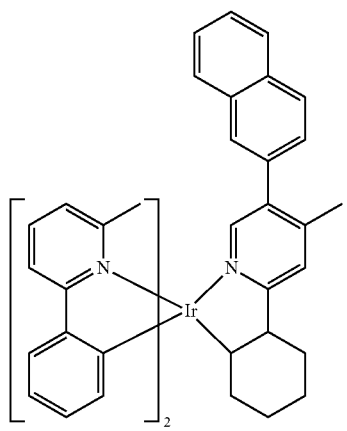
D19 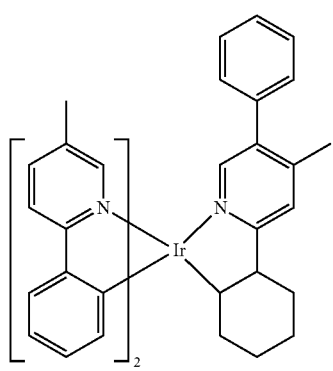
D20 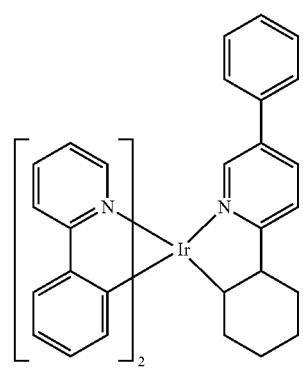
D21 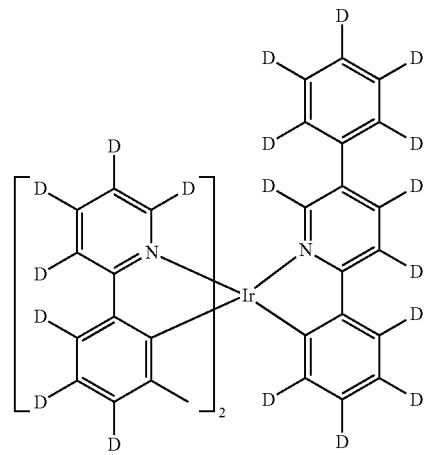
D22 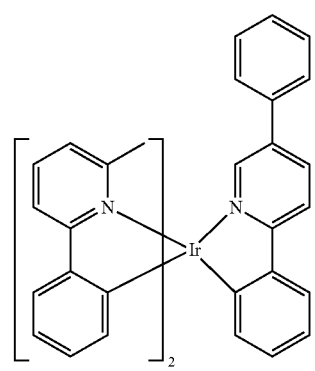
D23 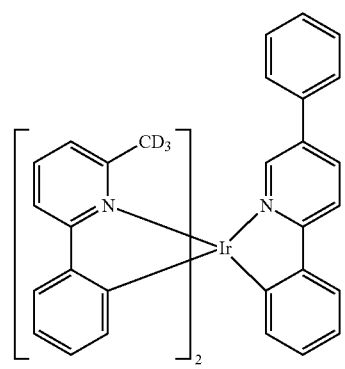

D24 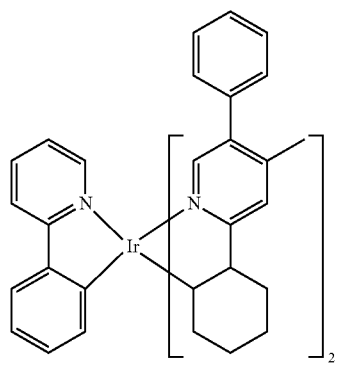
D25 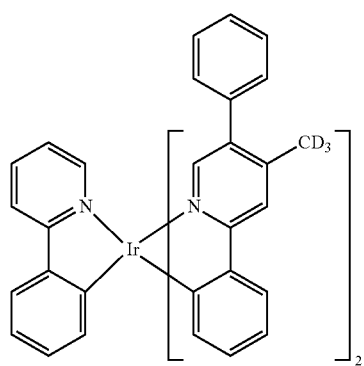
D26 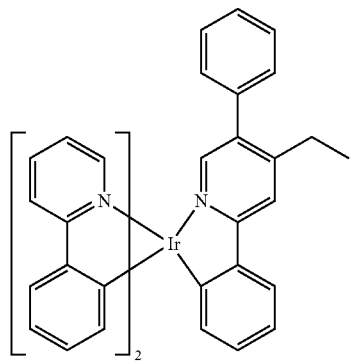
D27 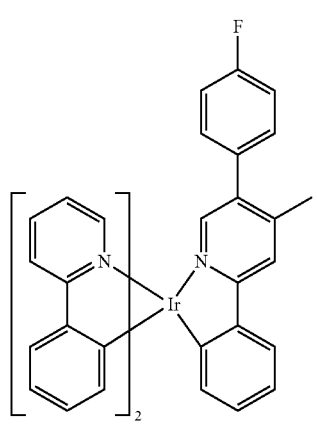
D28 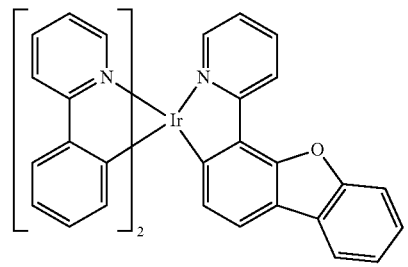
D29 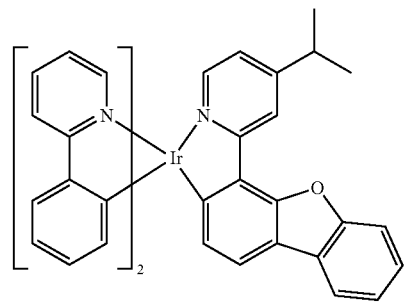
D30 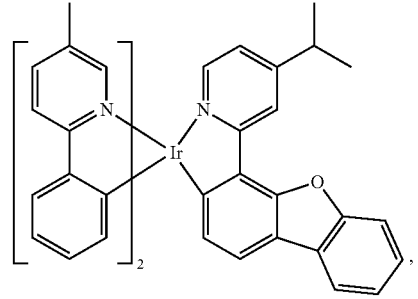
D31 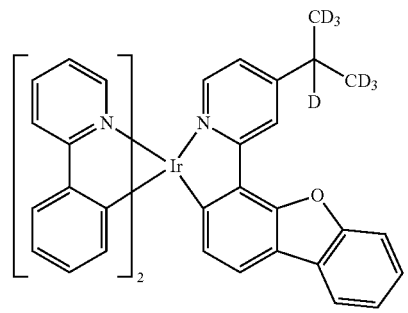
D32 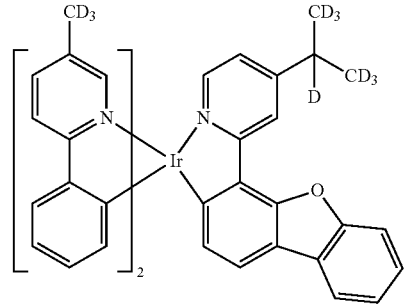

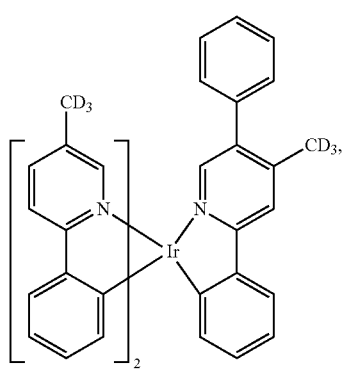
D33
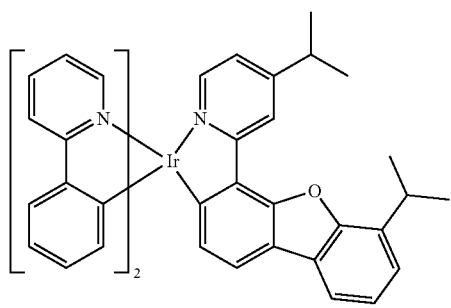
D34
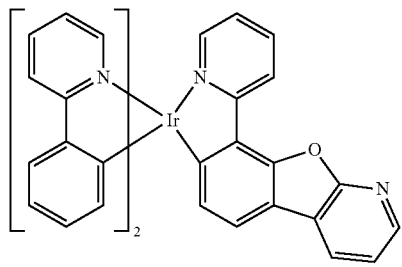
D35
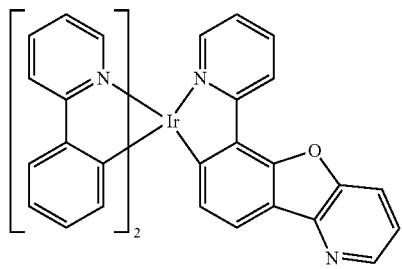
D36
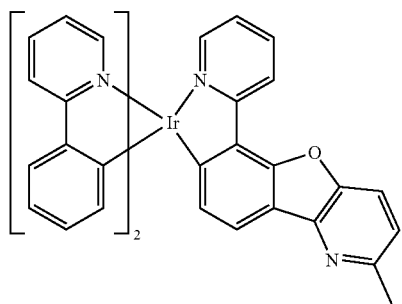
D37
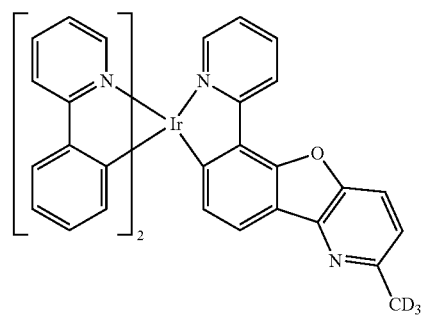
D38
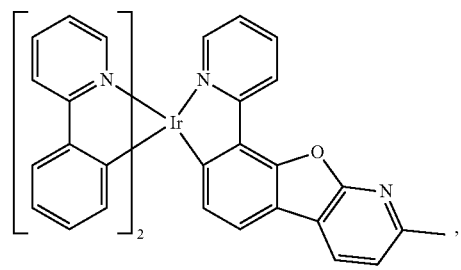
D39
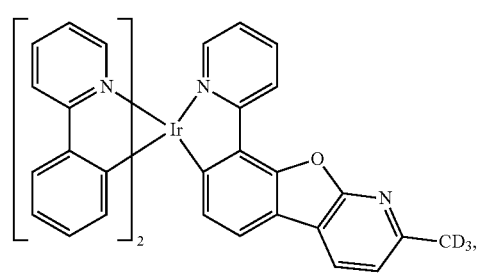
D40
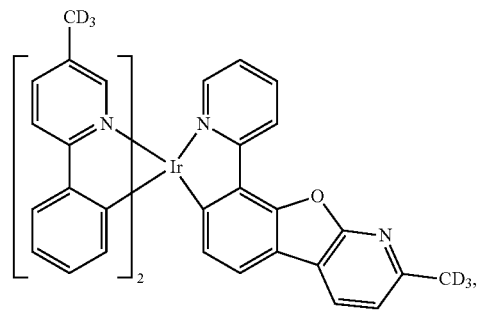
D41
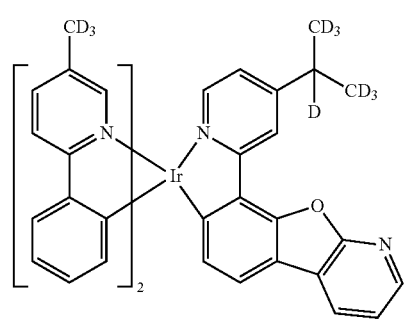
D42

D43
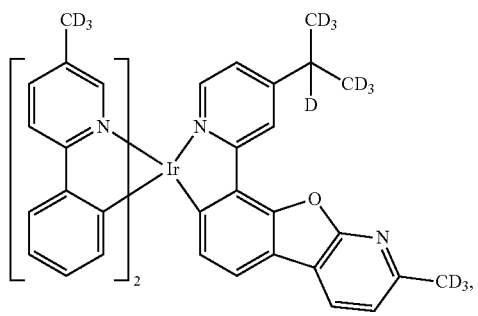
D44
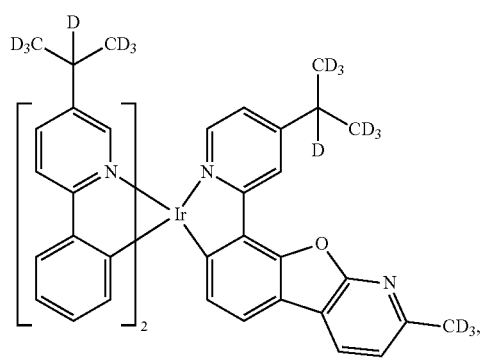
D45
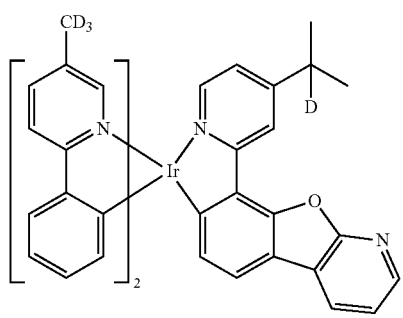
D46
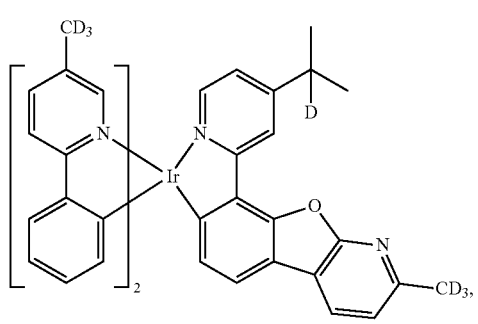
D47
D48
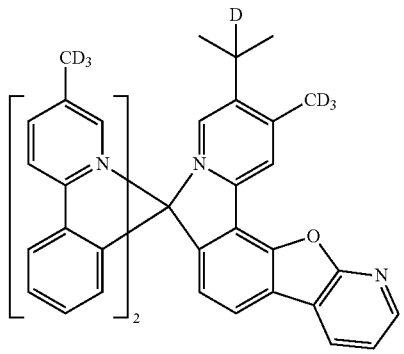
D49
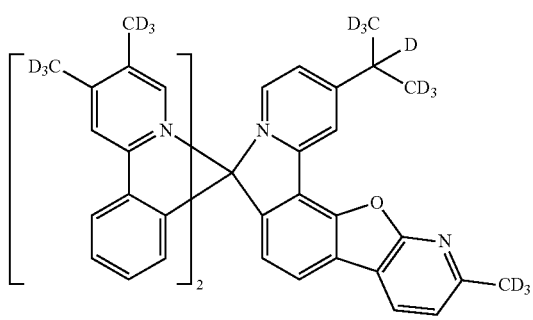
D50
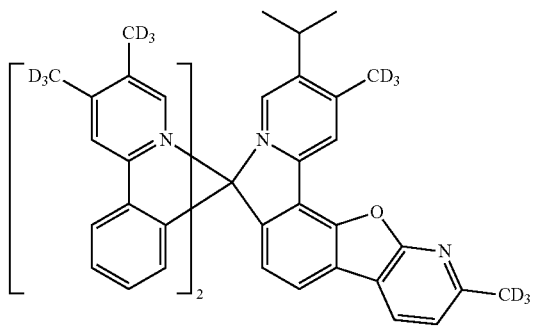
D51
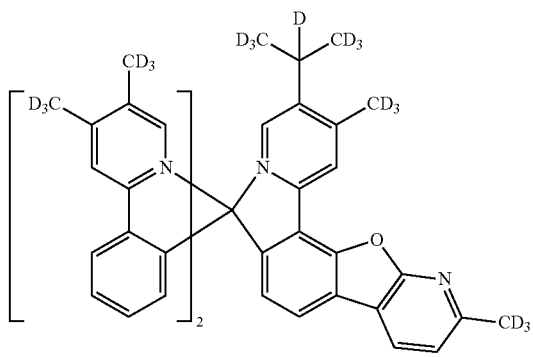

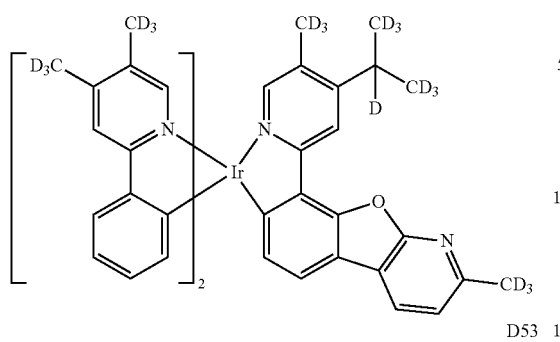
D52
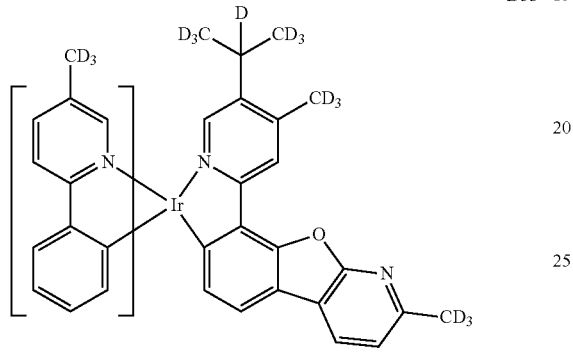
D53
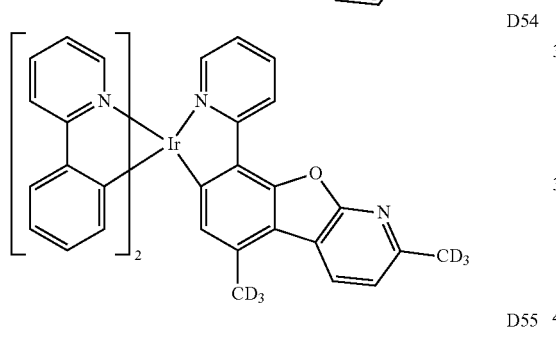
D54
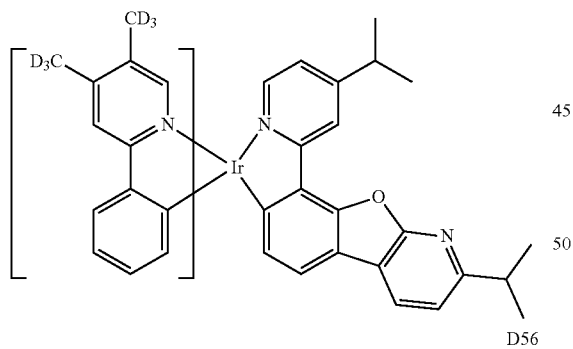
D55
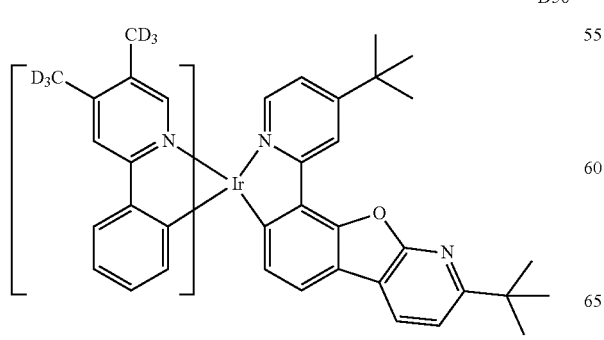
D56
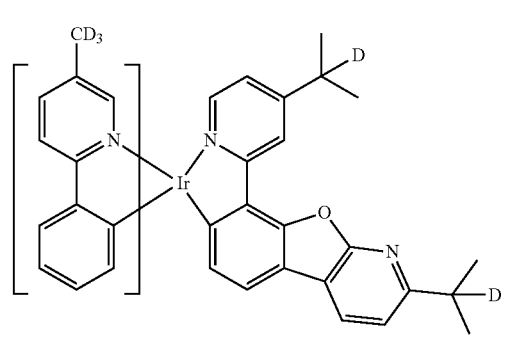
D57
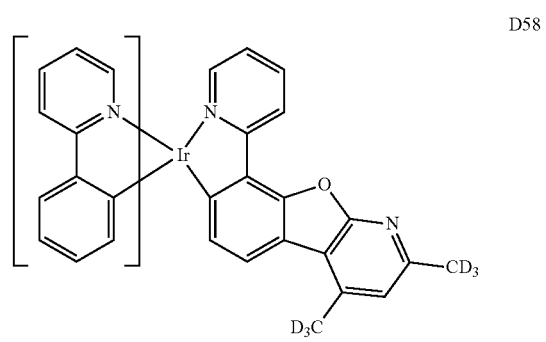
D58
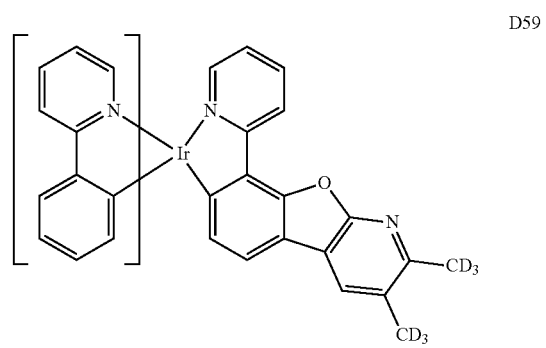
D59
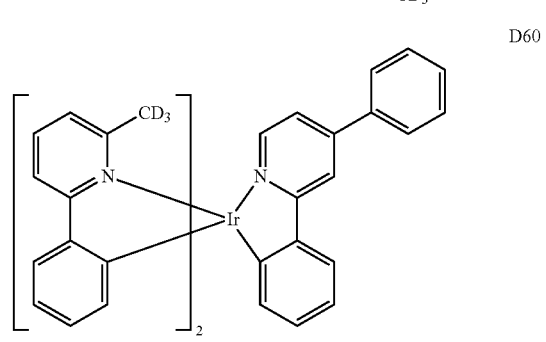
D60
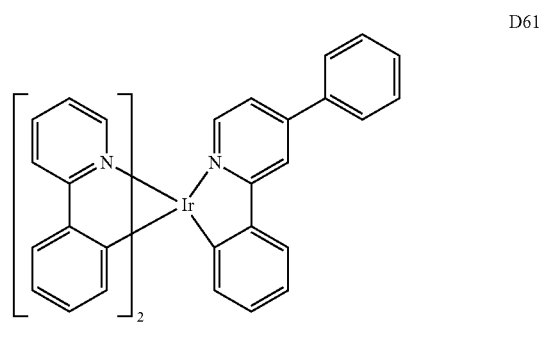
D61

D62
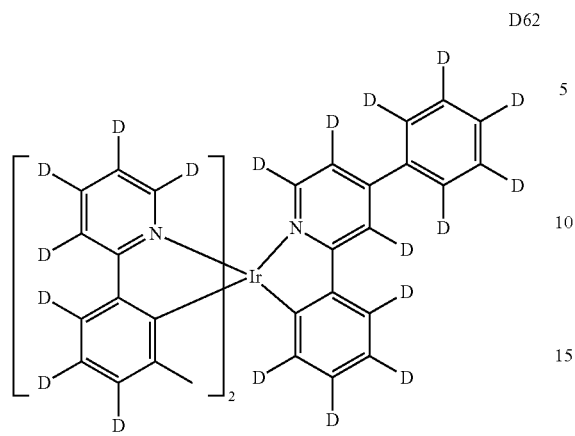
D63
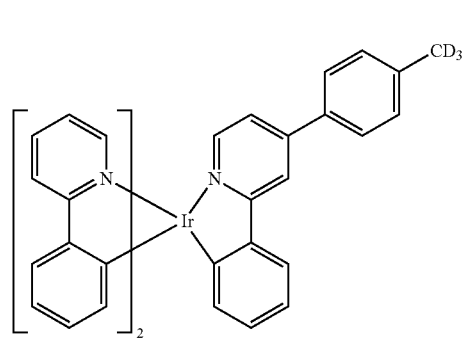
D64
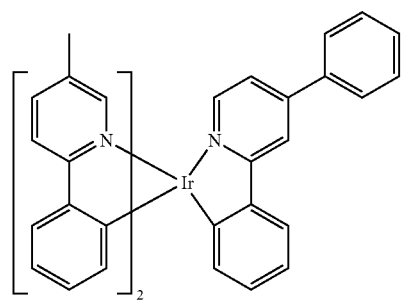
D65
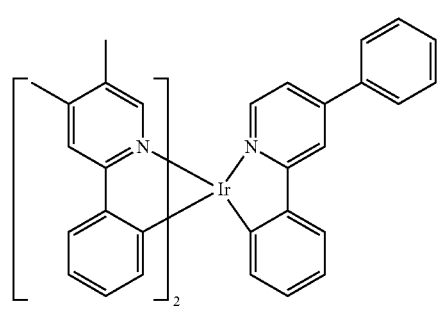
D66
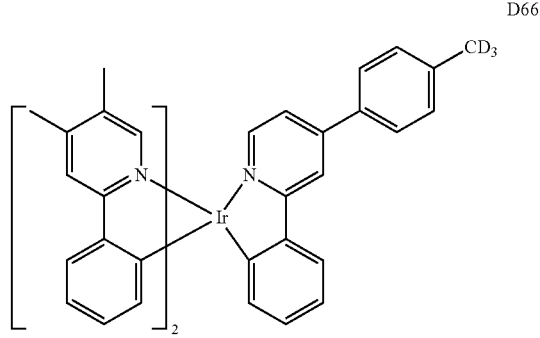
D67
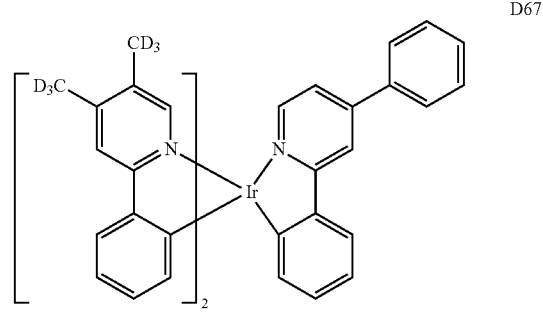
D68
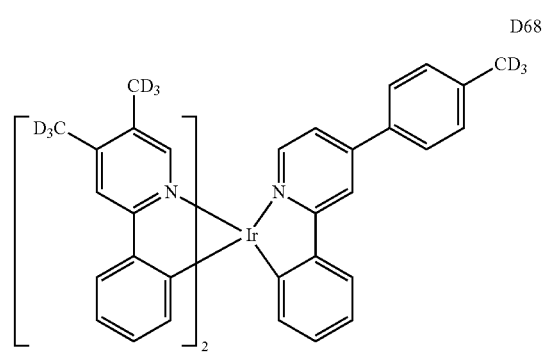
D69
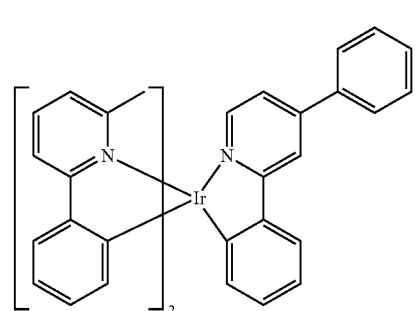
D70
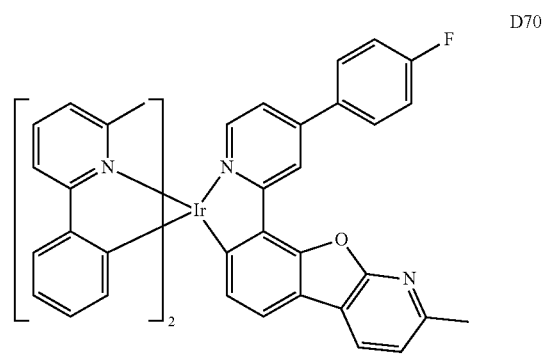

D71 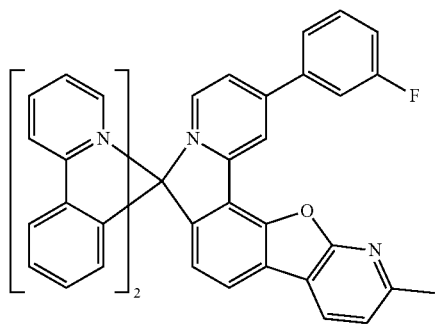
D72 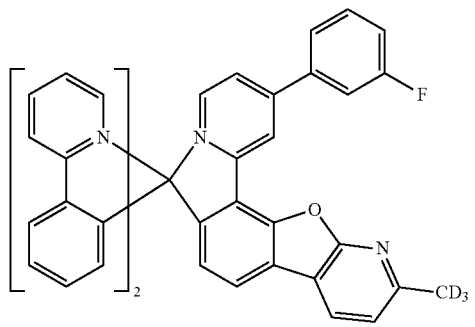
D73 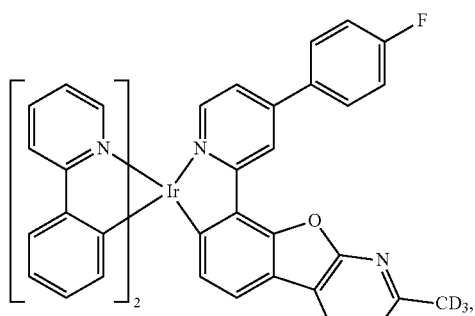
D74 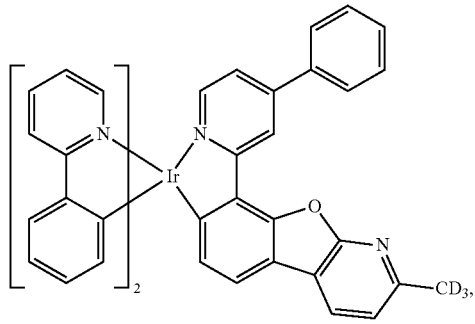
D75 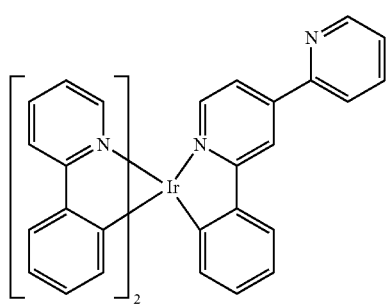
D76 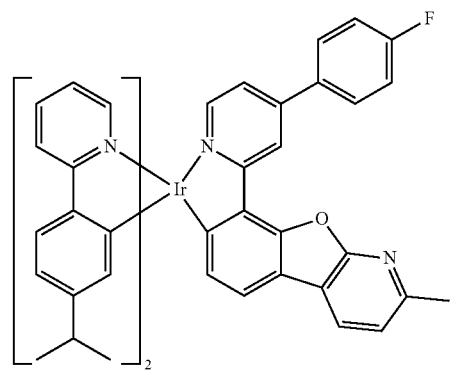
D77 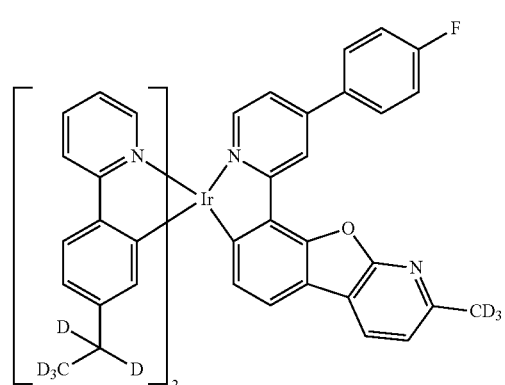
D78 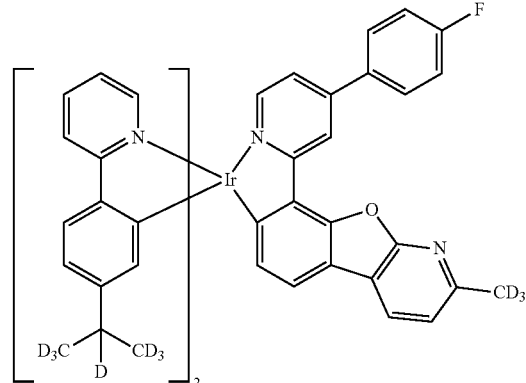
D79 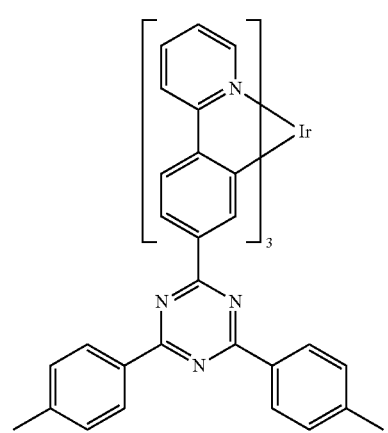

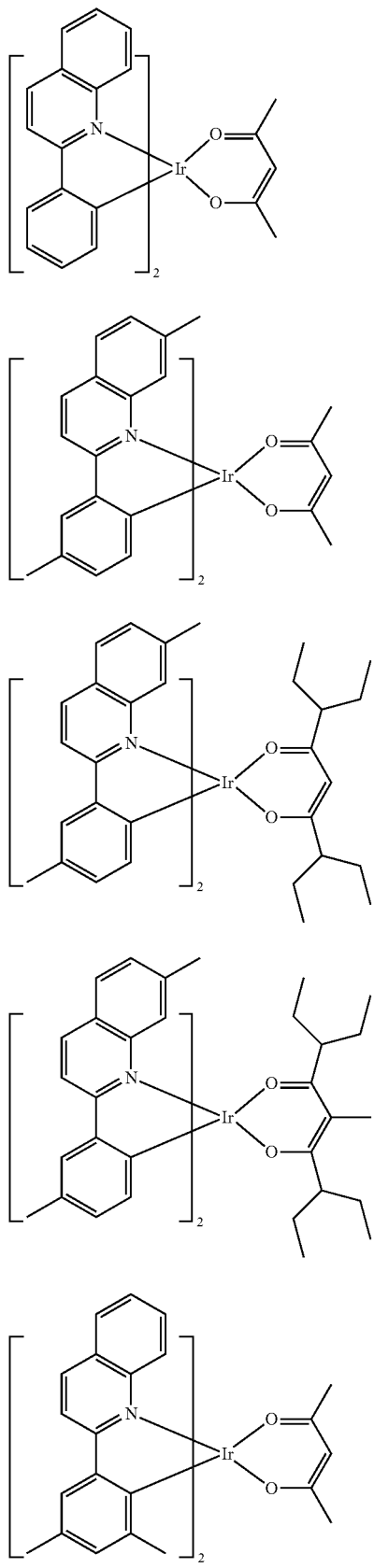
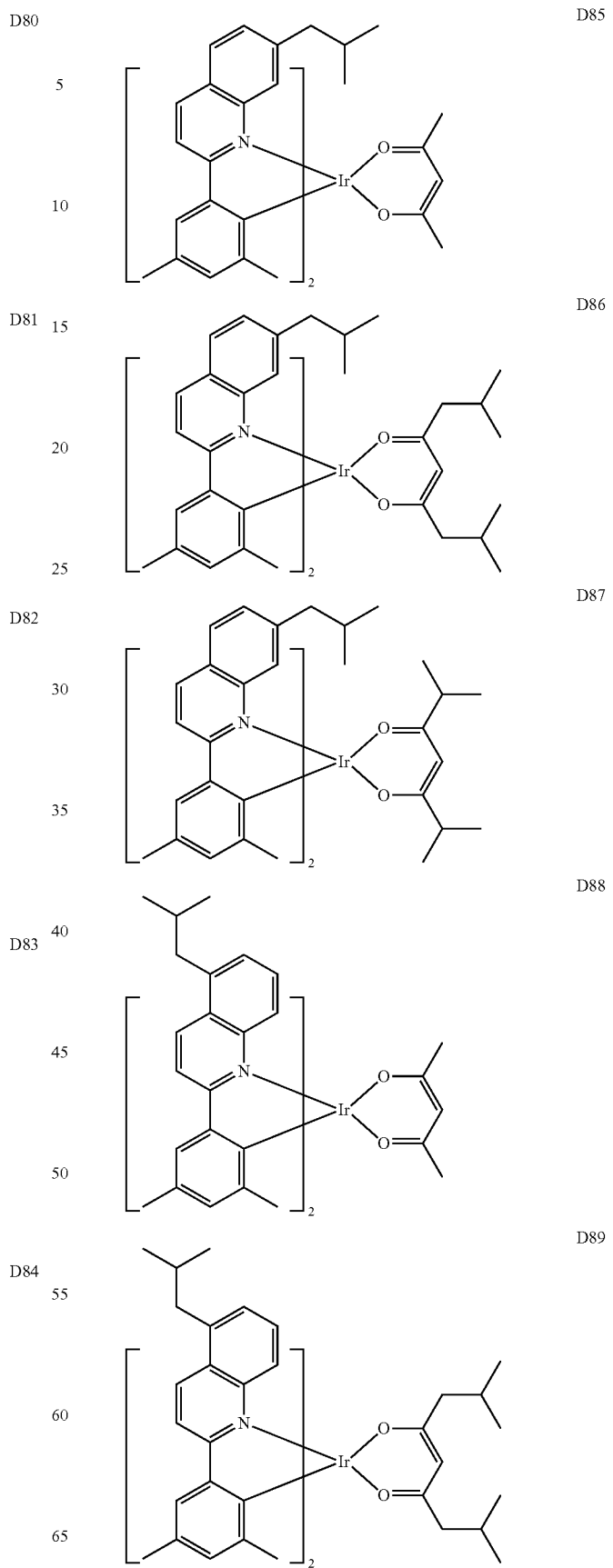

D90 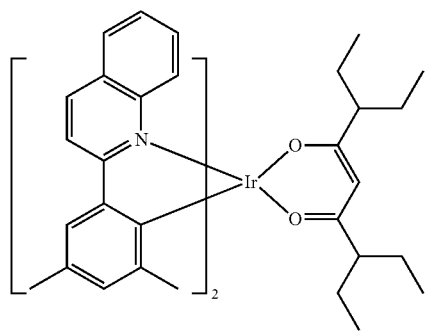
D91 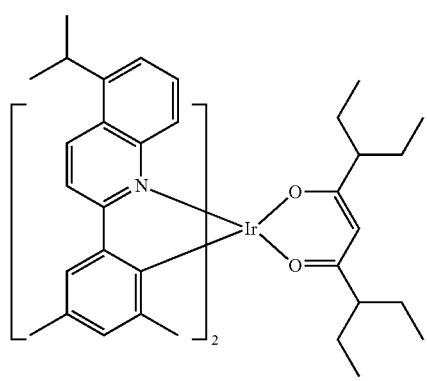
D92 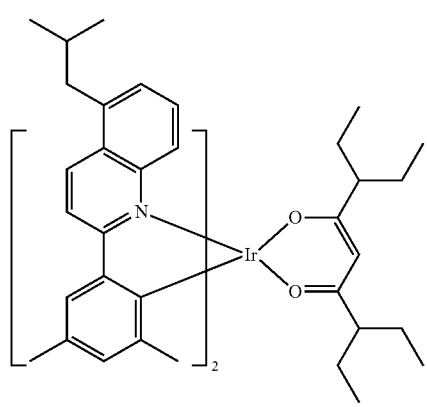
D93 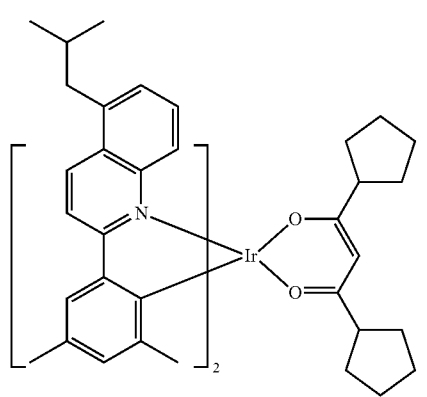
D94 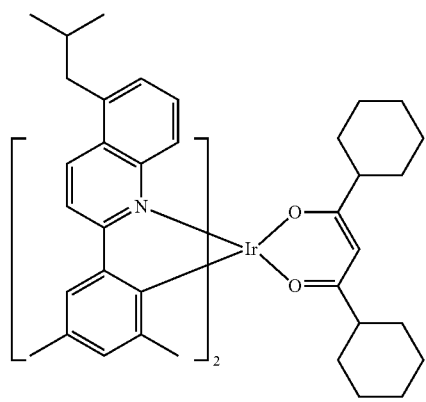
D95 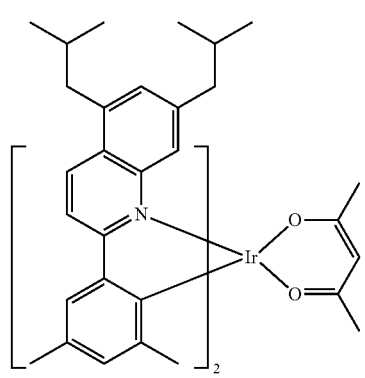
D96 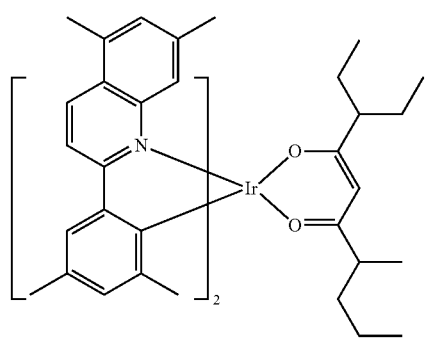
D97 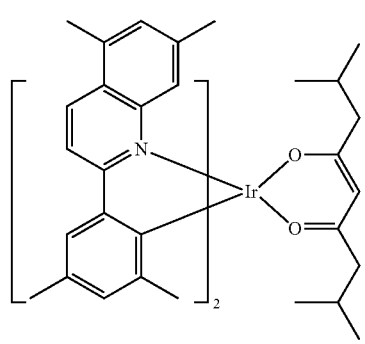

-continued
D98
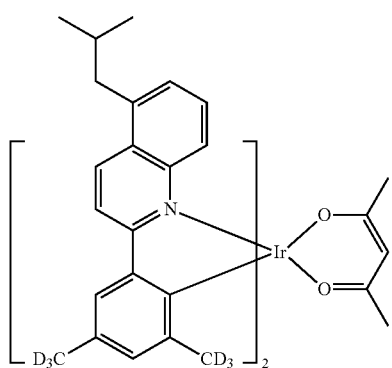
D99
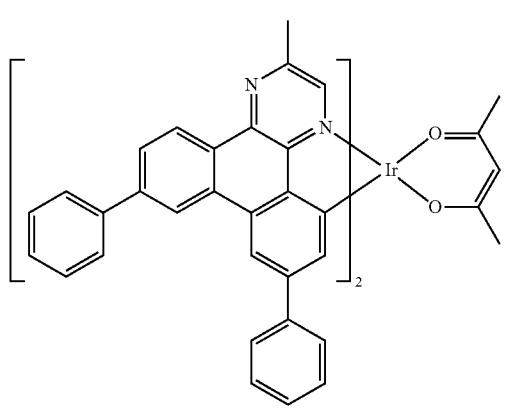
D100
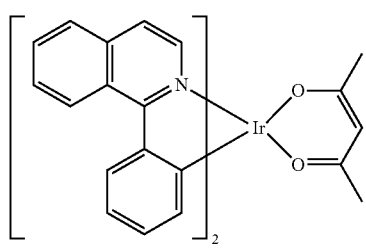
D101
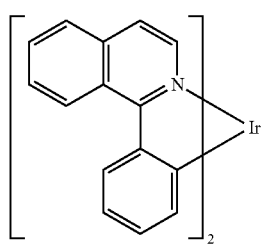
D102
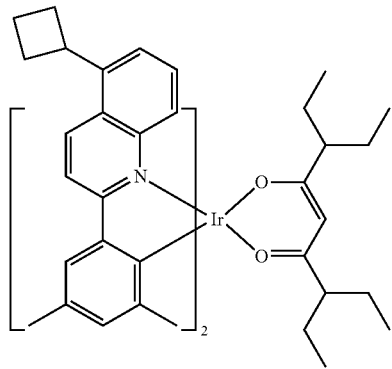
D103
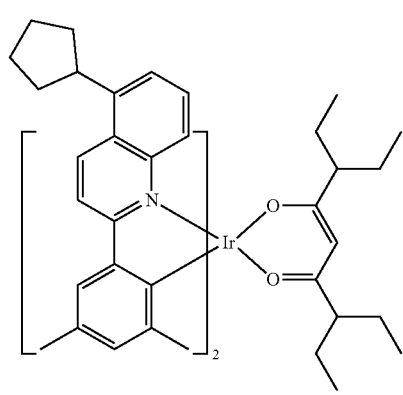
D104
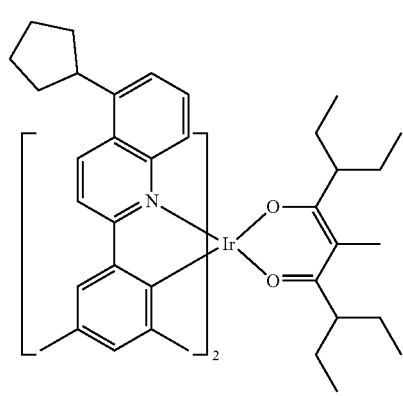
D105
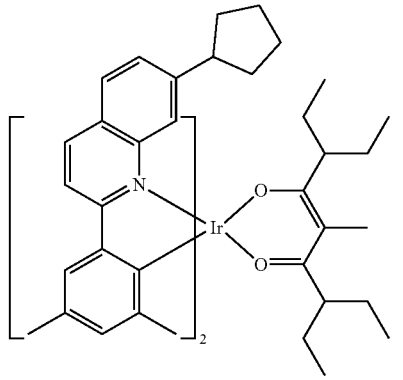
D106
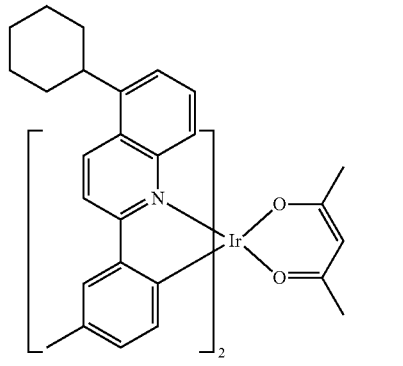

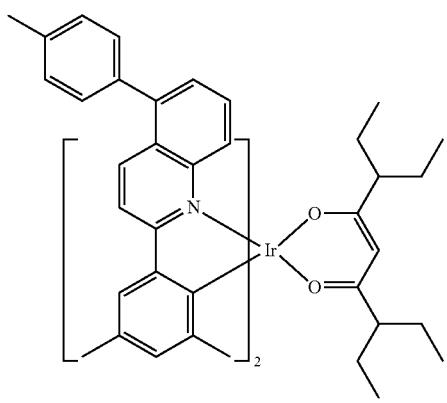
D107
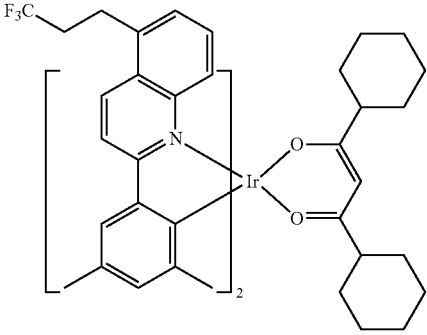
D111
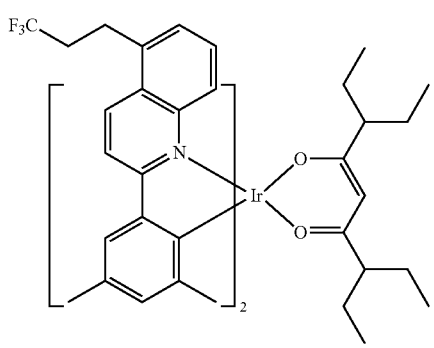
D108
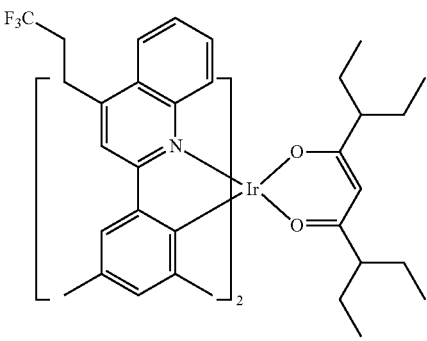
D112
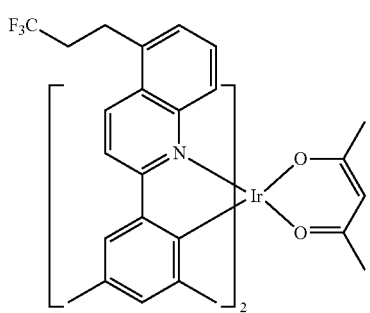
D109
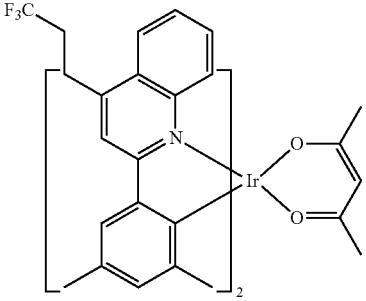
D113
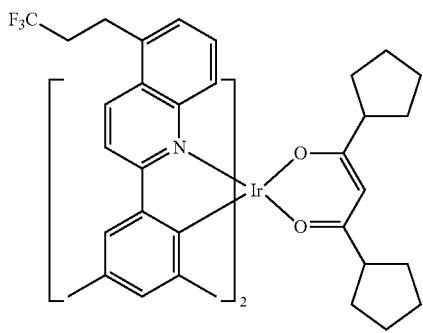
D110
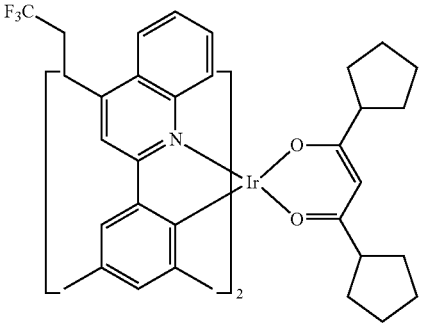
D114

D115 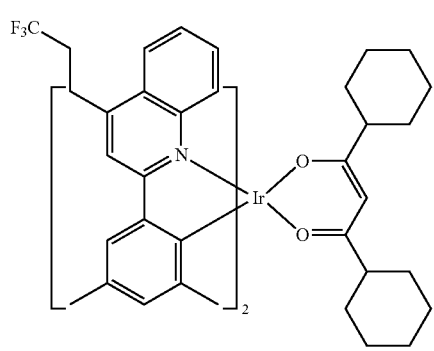
D119 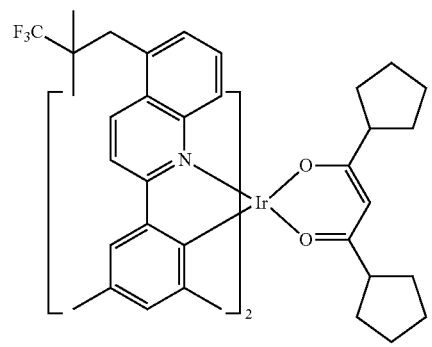
D116 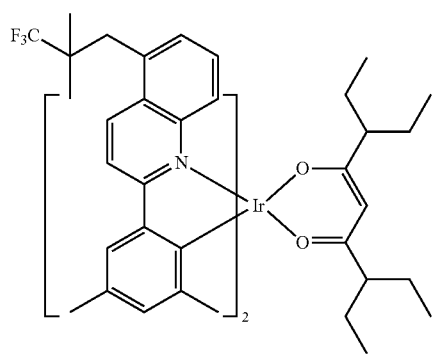
D120 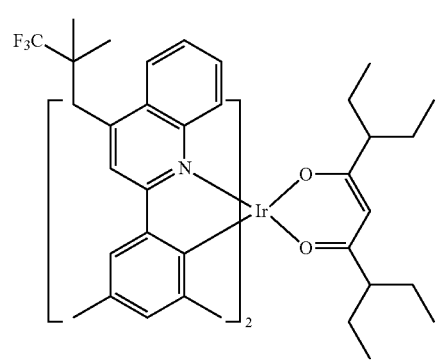
D117 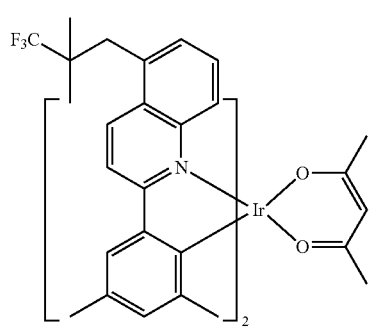
D121 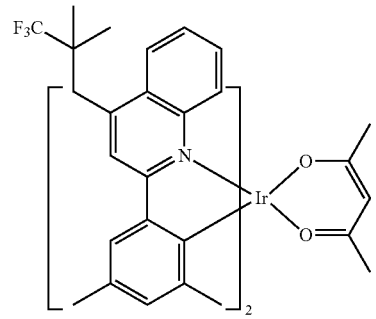
D118 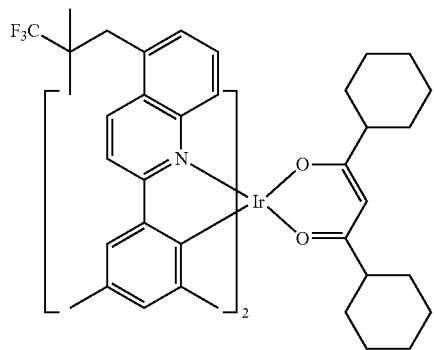
D122 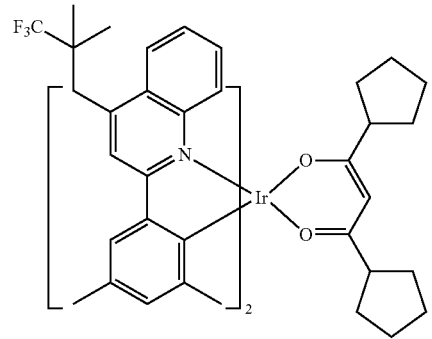

-continued
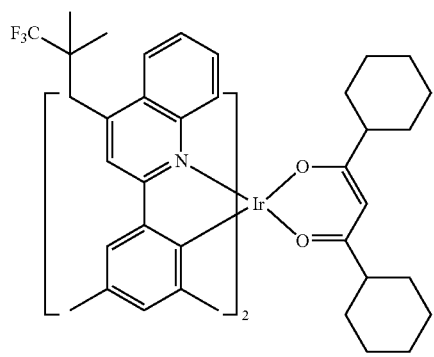
D123
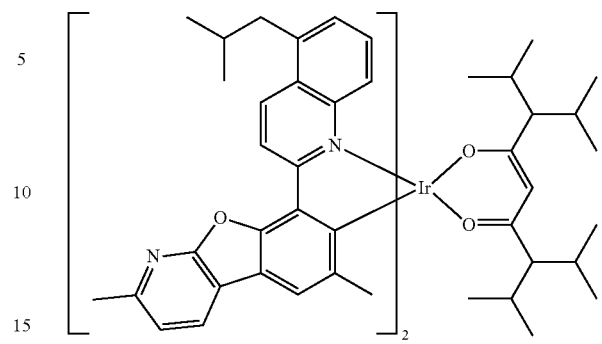
D127
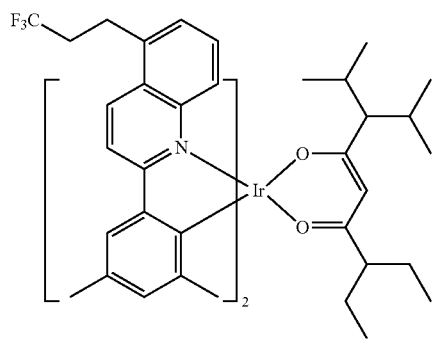
D124
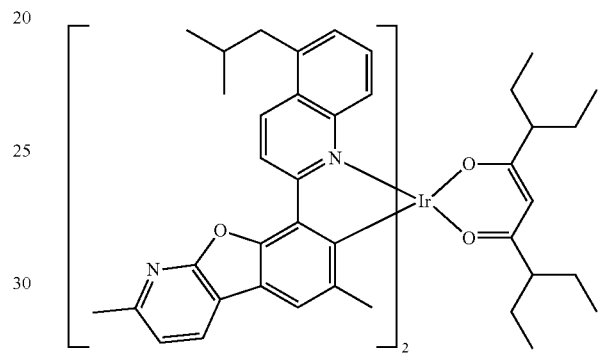
D128
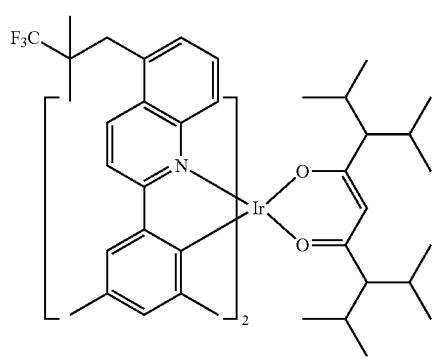
D125
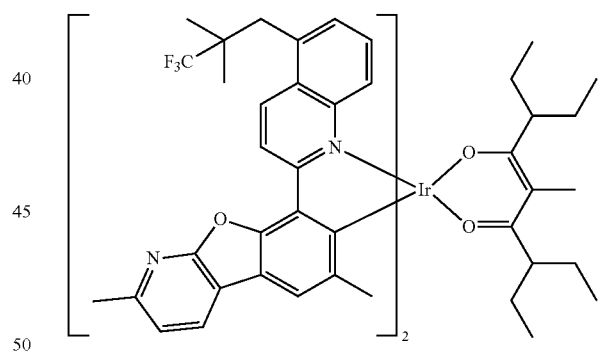
D129
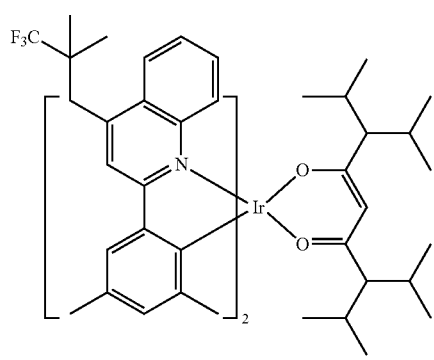
D126
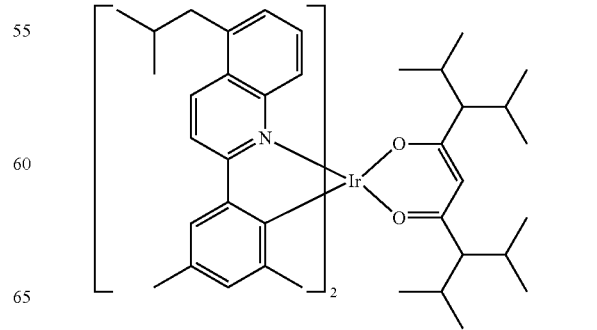
D130

D131 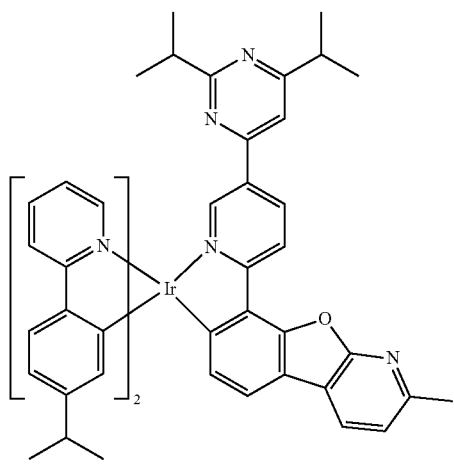
D135 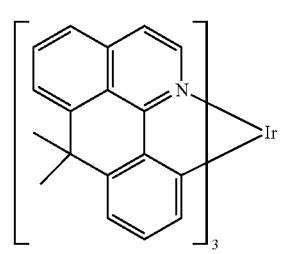
D136 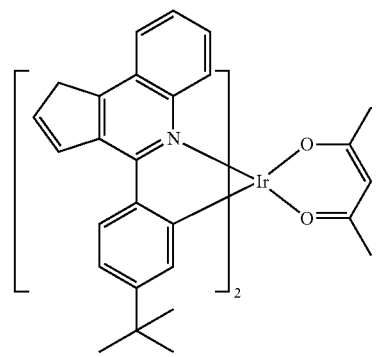
D132 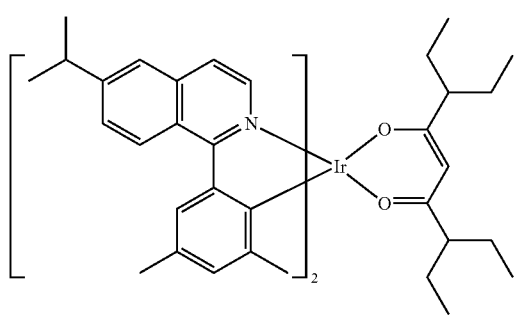
D137 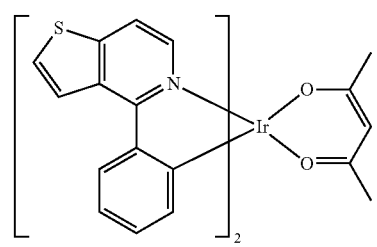
D133 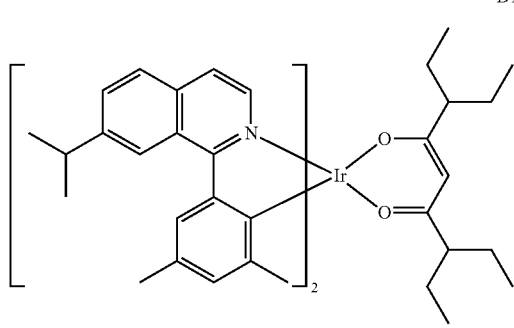
D138 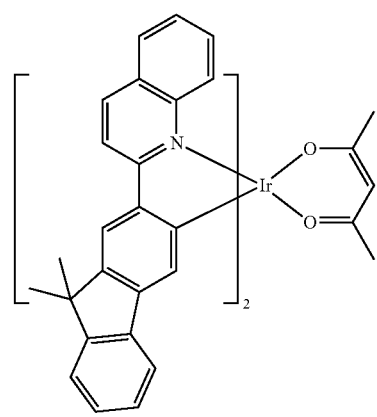
D134 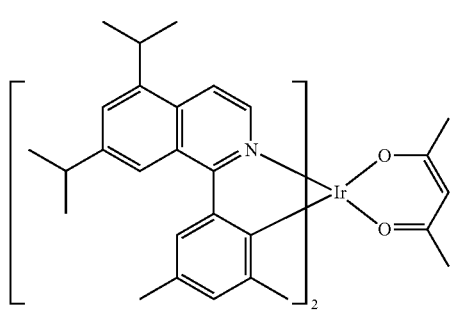
D139 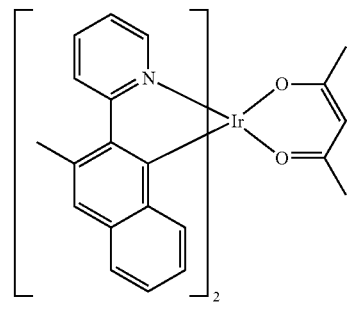

-continued

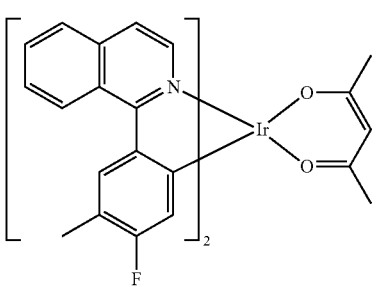

D140

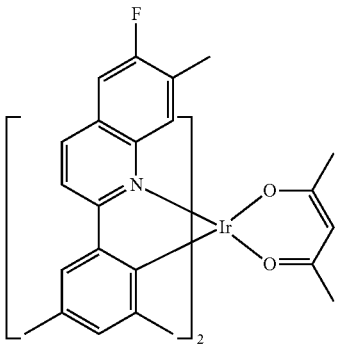

D141

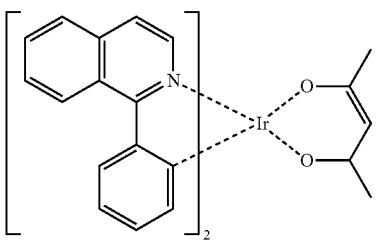

D142

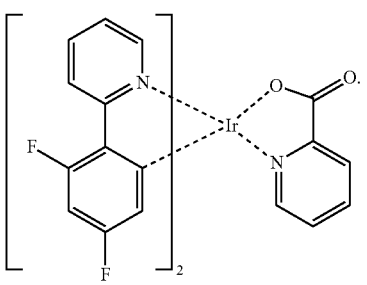

D143

The phosphorescent dopant is not limited to the above-described example compounds. For example, phosphorescence-emitting platinum group metal complexes described in paras. [0105] to [0113] in US 2016/0093808 or JP 2014-509067 are hereby incorporated by reference. Phosphorescence-emitting platinum group metal complexes described in these reference documents may be used as basis for amendments of the present specification.

The quantum dot may be a nanoparticle of a II-VI group semiconductor, a III-V group semiconductor, or a IV-VI group semiconductor For example, the quantum dot may be CdO, CdS, CdSe, CdTe, ZnO, ZnS, ZnSe, ZnTe, HgS, HgSe, HgTe, MgSe, MgS, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, GaN, GaP, GaAs, AlN, AlP, AlAs, InN, InP, InAs, InSb, GaNP, GaNAs, GaNSb, GaPAs, GaPSb, AlNP, AlNAs, AlNSb, AlPAs, AlPSb, InNP, InNAs, InPAs, InPSb, GaAlNP, SnS, SnSe, SnTe, PbS, PbSe, PbTe, SnSeS, SnSeTe, SnSTe, PbSeS, PbSeTe, PbSTe, SnPbS, SnPbSe, SnPbTe, or the like, but embodiments are not limited thereto In addition, a diameter of the quantum dot is not particularly limited; for example, the diameter may be in a range of about 1 nm to about 20 nm. The quantum dot may be in a single core structure or a core-shell structure.

A content of the luminescent material in the composition may be in a range of about 0.5 parts to about 50 parts by weight, for example about 1 part to about 30 parts by weight, or about 2 parts to about 25 parts by weight, based on 100 parts by weight of the heterocyclic compound represented by Formula 1 that may serve as a host material.

In addition, a content of the luminescent material in the composition may be in a range of about 0.5 parts to about 50 parts by weight, for example about 1 part to about 30 parts by weight, or about 2 parts to about 25 parts by weight, based on 100 parts by weight of the total weight of the heterocyclic compound represented by Formula 1, the first compound, and the second compound that may serve as a host material.

Within this range, the solubility of the composition is further improved, and precipitation is less likely to occur in the solution, resulting in a longer pot life of the solution. Accordingly, the organic light-emitting device may have improved luminescence efficiency and emission lifespan.

In some embodiments, the composition may include the heterocyclic compound represented by Formula 1, the first compound, the second compound, and a luminescent material (e.g., a phosphorescent dopant).

Figure 3:
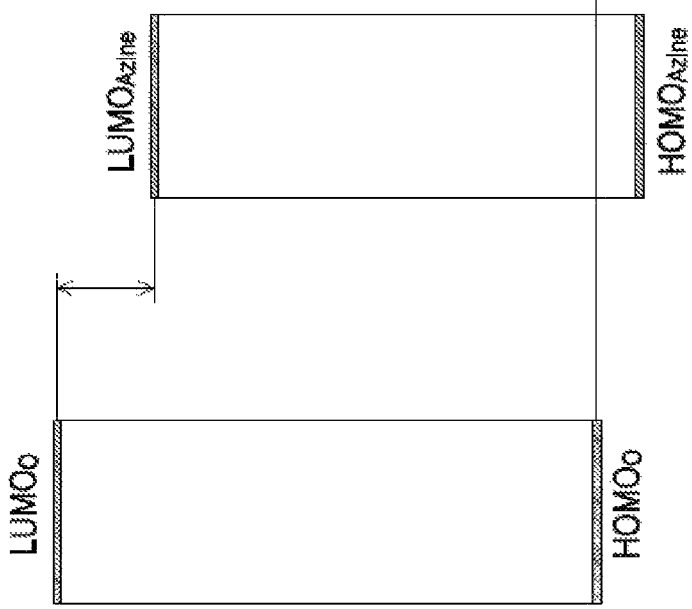
FIG. 3 is a diagram for illustrating an exemplary energy level relationship between the heterocyclic compound represented by Formula 1, the second compound containing an azine group, and a phosphorescence-emitting platinum group metal complex in a composition according to one or more embodiments.
Figure 3:
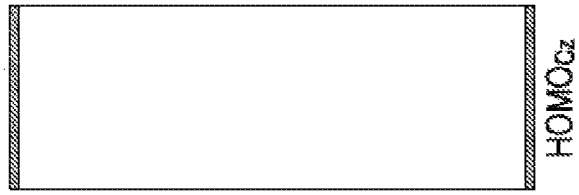
Figure 4:
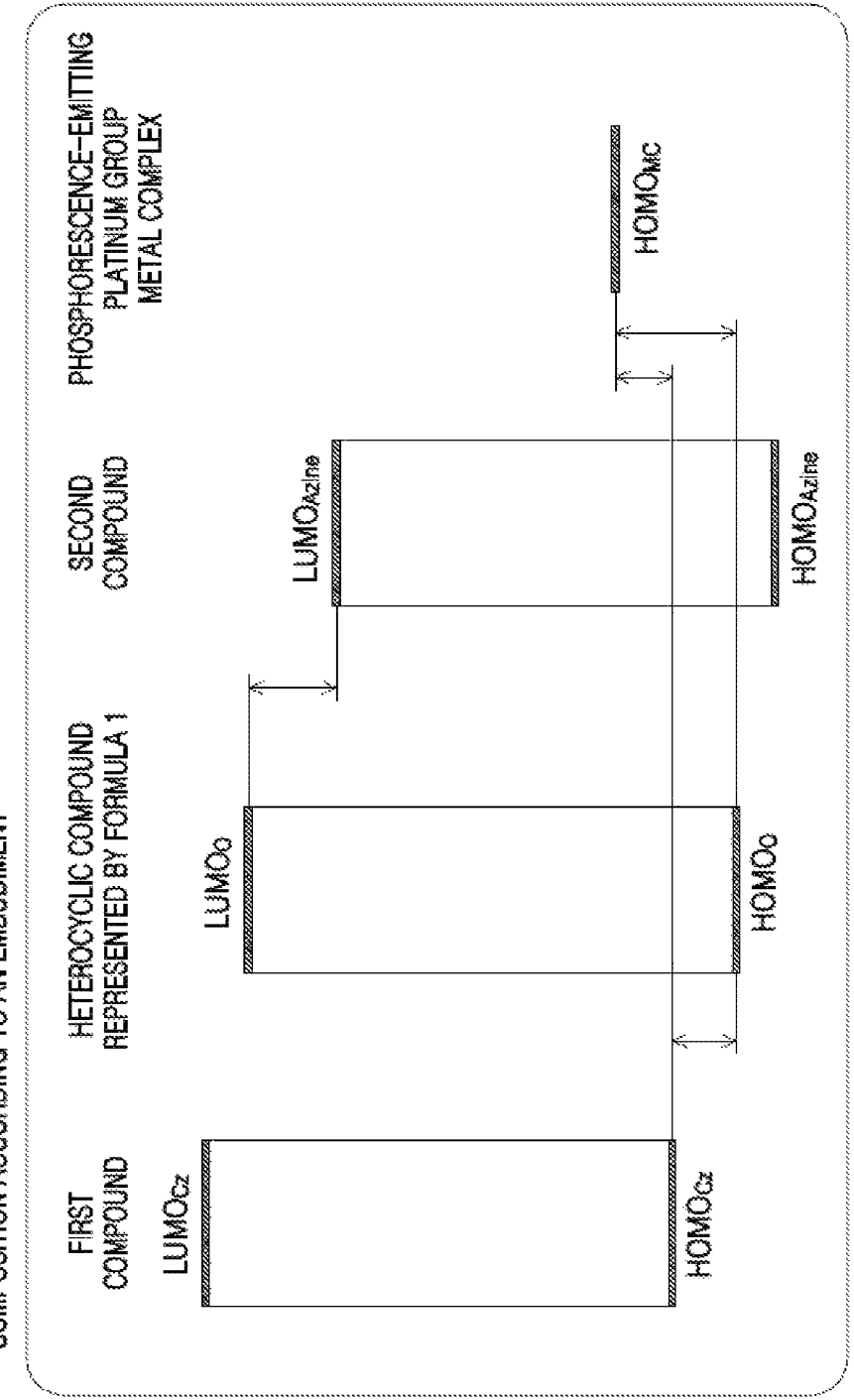
FIG. 4 is a diagram for illustrating an exemplary energy level relationship between the heterocyclic compound represented by Formula 1, the first compound containing a carbazole group, the second compound containing an azine group, and a phosphorescence-emitting platinum group metal complex in a composition according to one or more embodiments.

FIG. 3 is a diagram for illustrating an exemplary energy level relationship between the heterocyclic compound represented by Formula 1, the second compound containing an azine group, and a phosphorescence-emitting platinum group metal complex in a composition according to one or more embodiments. FIG. 4 is a diagram for illustrating an exemplary energy level relationship between the heterocyclic compound represented by Formula 1, the first compound containing a carbazole group, the second compound containing an azine group, and a phosphorescence-emitting platinum group metal complex in a composition according to one or more embodiments.

As shown in FIG. 3, in general, a LUMO of the heterocyclic compound represented by Formula 1 (LUMO$_0$) may be shallow relative to a LUMO of the second compound (LUMO$_{azine}$). In addition, in general, a HOMO of the heterocyclic compound represented by Formula 1 (HOMO$_0$) may be deeper than a HOMO (HOMO$_{Cz}$) of the first compound. Further, in general, the hole mobility of the heterocyclic compound represented by Formula 1 may be lower than the hole mobility of the first compound.

As shown in FIG. 4, LUMO$_0$ may be, in general, shallow relative to LUMO$_{azine}$. In addition, in general, HOMO$_0$ may be, deeper than HOMO$_{Cz}$. Further, in general, the hole mobility of the heterocyclic compound represented by Formula 1 may be lower than the hole mobility of the first compound.

Accordingly, when an organic layer (e.g., emission layer) includes the heterocyclic compound represented by Formula 1 or a composition containing the heterocyclic compound represented by Formula 1, a hole transporting host material such as the first compound, an electron transporting host material such as the second compound, and the phosphorescence-emitting platinum group metal complex, the following mechanism may be exhibited.

First, in an organic layer including the composition, electrons may be trapped once in the deepest LUMO$_{azine}$.

However, the trapped electrons may be detrapped in $LUMO_0$ and restart migration. Therefore, in the organic layer, electrons may be moved due to the repetition of trapping-detrapping between $LUMO_{azine}$ and $LUMO_0$, and an electron mobility decreases. This is the same in FIG. 3.

In addition, holes may be trapped in a HOMO of a phosphorescence-emitting metal complex ($HOMO_{MC}$). The trapped holes may restart migration by being detrapped in $HOMO_{Cz}$.

The composition may further include a solvent.

The solvent is not particularly limited as long as the solvent dissolves the heterocyclic compound represented by Formula 1. Preferably, the solvent further dissolves the first compound represented by Formula 5 and/or the second compound represented by Formula 6. In some embodiments, the solvent may be toluene, xylene, ethylbenzene, diethylbenzene, mesitylene, propylbenzene, cyclohexylbenzene, dimethoxybenzene, anisole, ethoxytoluene, phenoxytoluene, isopropylbiphenyl, dimethylanisole, phenyl acetate, phenyl propionate, methyl benzoate, ethyl benzoate, or any combination thereof, or the like, but embodiments are not limited thereto.

Therefore, the composition may be used as a material for a light-emitting device (e.g., an organic light-emitting device or a quantum dot light-emitting device). In particular, the composition may be used in an emission layer, a charge injection layer, and/or a charge transport layer in a light-emitting device. In particular, the composition may be used in an emission layer in a light-emitting device. In particular, the composition may be used when a light-emitting device is manufactured by a solution coating method, and in this case, current efficiency and emission lifespan of the light-emitting device may be maintained or improved.

Organic Light-Emitting Device

Hereinafter, with reference to FIG. 5, an embodiment of an organic light-emitting device will be described in detail FIG. 5 is a schematic view of an organic light-emitting device according to an embodiment.

An organic light-emitting device 100 according to an exemplary embodiment may include a substrate 110, a first electrode 120 on the substrate 110, a hole injection layer 130 on the first electrode 120, a hole transport layer 140 on the hole injection layer 130, an emission layer 150 on the hole transport layer 140, an electron transport layer 150 on the emission layer 150, an electron injection layer 170 on the electron transport layer 160, and a second electrode 180 on the electron injection layer 170.

In the organic light-emitting device 100, the heterocyclic compound represented by Formula 1 may be, for example, included in at least one organic layer (e.g., at least one organic layer selected from the hole injection layer 130, the hole transport layer 140, the emission layer 150, the electron transport layer 160, and the electron injection layer 170) between the first electrode 120 and the second electrode 180. In some embodiments, the heterocyclic compound represented by Formula 1 may be included in the emission layer 150 as a host. In some embodiments, the heterocyclic compound represented by Formula 1 may be included in an organic layer other than the emission layer 150. For example, the heterocyclic compound represented by Formula 1 may be included in the hole injection layer 130 and/or the hole transport layer 140 as a hole transport material.

The term "organic layer" as used herein refers to a single and/or a plurality of layers between the first electrode and the second electrode in an organic light-emitting device. The "organic layer" may include not only organic compounds but also organometallic compounds including metals.

As used herein, "(for example, the organic layer) including at least one heterocyclic compound represented by Formula 1 "means" (the organic layer) including one heterocyclic compound represented by Formula 1, or at least two different heterocyclic compounds represented by Formula 1."

For example, the organic layer may include Compound 1 only as the heterocyclic compound represented by Formula 1. In this embodiment, Compound 1 may be included in the emission layer of the organic light-emitting device. In some embodiments, the organic layer may include Compounds 1 and 2 as the heterocyclic compounds represented by Formula 1. In this embodiment, Compounds 1 and 2 may both be included in the same layer (for example, both Compounds 1 and 2 may be included in the emission layer).

The substrate 110 may be any suitable substrate generally used in organic light-emitting devices. For example, the substrate 110 may be a glass substrate, a silicon substrate, or a transparent plastic substrate having excellent mechanical strength, thermal stability, transparency, surface smoothness, ease of handling, and water repellency, but embodiments are not limited thereto The first electrode 120 may be formed on the substrate 110. The first electrode 120 may be an anode and be formed of a material with a relatively high work function such as a metal, an alloy, or a conductive compound, for facilitating hole injection. The first electrode 120 may be a reflective electrode, a semi-transmissive electrode, or a transmissive electrode. The first electrode 120 may have a single-layered structure or a multi-layered structure including a plurality of layers. For example, the first electrode 120 may be a transparent electrode formed of indium tin oxide (ITO), indium zinc oxide (IZO), tin oxide ($SnO_2$), or zinc oxide (ZnO) having excellent transparency and conductivity. The first electrode 120 may be a reflective electrode that may be formed by stacking magnesium (Mg), aluminum (Al), aluminum-lithium (Al—Li), calcium (Ca), magnesium-indium (Mg—In), or magnesium-silver (Mg—Ag) on the transparent electrode. For example, the first electrode 120 may have a triple-layer structure of ITO/Ag/ITO, but embodiments are not limited thereto.

A hole transport region may be formed on the first electrode 120.

The hole transport region may include at least one of the hole injection layer 130; the hole transport layer 140, an electron blocking layer (not shown), and a buffer layer (not shown).

The hole transport region may include the hole injection layer 130 only or the hole transport layer 140 only. In some embodiments, the hole transport region may include a hole injection layer and a hole transport layer which are sequentially stacked on the first electrode 120. In some embodiments, the hole transport region may include a hole injection layer, a hole transport layer, and an electron blocking layer, which are sequentially stacked on the first electrode 11.

The hole injection layer 130 may include, for example, at least one poly(ether ketone)-containing triphenylamine (TPAPEK), 4-isopropyl-4'-methyl diphenyl iodonium tetrakis (pentafluorophenyl) borate (PPBI), N,N'-diphenyl-N,N'-bis-[4-(phenyl-m-tolyl-amino)-phenyl]-biphenyl-4,4'diamine (DNTPD), copper phthalocyanine, 4,4',4"-tris(3-methyl phenyl phenyl amino) triphenylamine (m-MTDATA), N,N'-di(1-naphthyl)-N,N'-diphenylbenzidine (NPB), 4,4',4"-tris (diphenyl amino) triphenylamine (TDATA), 4,4',4"-tris(N,N-2-naphthyl phenyl amino) triphenylamine (2-TNATA), polyaniline/dodecylbenzenesulphonic acid (PAN/DBSA), poly(3,4-ethylenedioxythiophene)/poly(4-styrenesulfonate (PEDOT/PSS), polyaniline/10-camphorsulfonic acid (PANI/CSA), polyaniline/poly(4-styrenesulfonate) (PANI/PSS), or any combination thereof.

The hole injection layer 130 may be formed to a thickness of about 10 nanometers (nm) to about 1,000 nm, and more particularly, to a thickness of about 10 nm to about 100 nm.

The hole transport layer may include, for example, at least one carbazole derivatives, e.g., 1,1-bis[(di-4-tolylamino) phenyl] cyclohexane (TAPC), N-phenylcarbazole, and polyvinylcarbazole, N,N'-bis(3-methylphenyl)-N,N'-diphenyl-[1,1-biphenyl]-4,4'-diamine (TPD), 4,4',4"-tris(N-carbazolyl) triphenylamine (TCTA), N,N'-di(1-naphthyl)-N,N'-diphenylbenzidine (NPB), and poly(9,9-dioctyl-fluorene-co-N-4-butylphenyl)-diphenylamine (TFB).

The hole transport layer 140 may be formed to a thickness of about 10 nm to about 1,000 nm, and more particularly, to a thickness of about 10 nm to about 150 nm.

The hole transport region may include a charge generating material as well as the aforementioned materials, to improve conductive properties of the hole transport region. The charge generating material may be substantially homogeneously or non-homogeneously dispersed in, the hole transport region.

The charge generating material may include, for example, a p-dopant. The p-dopant may include a quinone derivative, a metal oxide, a compound containing a cyano group, or a combination thereof, but embodiments are not limited thereto. For example, non-limiting examples of the p-dopant include a quinone derivative, such as tetracyanoquinodimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1 or Compound HT-D2, but embodiments are not limited thereto:

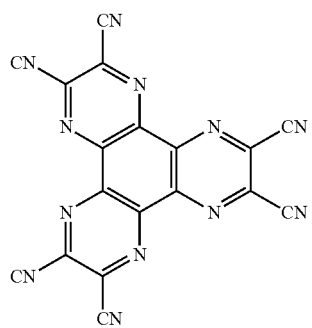

HT-D1

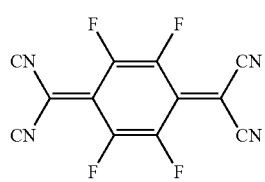

F4-TCNQ

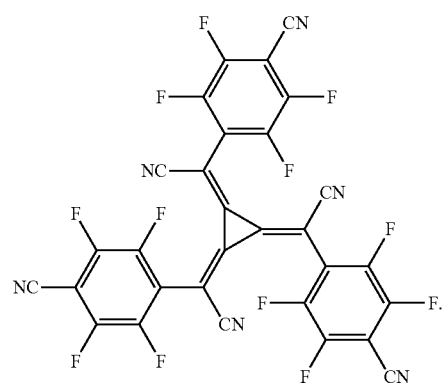

HT-D2

When the hole transport region includes a buffer layer, a material for forming the buffer layer may be a material for forming a hole injection or transport layer and host materials described herein, but embodiments are not limited thereto.

When the hole transport region includes an electron blocking layer, a material for forming the electron blocking layer may be a material for forming a hole injection or transport layer and host materials described herein, but embodiments are not limited thereto. In some embodiments, when the hole transport region includes an electron blocking layer, mCP may be used for forming the electron blocking layer.

The emission layer 150 may be formed on the hole transport region. The emission layer 150 may emit light by fluorescence or phosphorescence mechanism. The emission layer 150 may include a host and a dopant, and the host may include the heterocyclic compound represented by Formula 1. The emission layer 150 may further include a known host material. The emission layer 150 may include a known dopant material.

In some embodiments, the host may include tris(8-hydroxyquinolinato)aluminum ($Alq_3$), 4,4'-bis(carbazol-9-yl) biphenyl (CBP), poly(N-vinylcarbazole) (PVK), 9,10-di (naphthalene-yl)anthracene (ADN), 4,4',4"-tris(N-carbazolyl)triphenylamine (TCTA), 1,3,5-tris(N-phenyl-benzimidazol-2-yl)benzene (TPBi), 3-tert-butyl-9,10-di (naphth-2-yl)anthracene (TBADN), distyrylarylene (DSA), 4,4'-bis(9-carbazolyl)-2,2'-dimethyl-biphenyl (dmCBP), or a combination thereof, but embodiments are not limited thereto.

In some embodiments, the host may further include at least one the first compound and the second compound, but embodiments are not limited thereto.

In some embodiments, the dopant may include perylene and a derivative thereof, rubrene and a derivative thereof, coumarin and a derivative thereof, 4-(dicyanomethylene)-2-(p-dimethylaminostyryl)-6-methyl-4H-pyran (DCM) and a derivative thereof, an iridium complex, e.g., bis[2-(4,6-difluorophenyl)pyridinate]picolinate iridium (III) (FIrpic), bis(1-phenylisoquinoline)(acetylacetonate) iridium (III) (Ir(piq)$_2$(acac)), tris(2-phenylpyridine) iridium (III) (Ir(ppy)$_3$), tris(2-(3-p-xylyl)phenylpyridine) iridium (III)) (dopant), and the like, an osmium complex, and a platinum complex, but embodiments are not limited thereto.

When the emission layer includes the host and the dopant, an amount of the dopant may be in a range of about 0.01 parts to about 15 parts by weight based on about 100 parts by weight of the host, but embodiments are not limited thereto.

The emission layer 150 may be formed to a thickness in a range of about 10 nm to about 60 nm.

When the organic light-emitting device 10 is a full-color organic light-emitting device, the emission layer may be patterned into a red emission layer, a green emission layer, and/or a blue emission layer. In some embodiments, the emission layer may have a structure in which the red emission layer, the green emission layer, and/or the blue emission layer are layered to emit white light. In some embodiments, the structure of the emission layer may vary.

Then, an electron transport region may be formed on the emission layer 150.

The electron transport region may include at least one a hole blocking layer (not shown), the electron transport layer 160, and the electron injection layer 170.

In some embodiments, the electron transport region may have a hole blocking layer/an electron transport layer/an electron injection layer structure or an electron transport layer/an electron injection layer structure, but embodiments are not limited thereto. The electron transport layer may have a single-layered structure or a multi-layered structure including two or more different materials.

For example, in order to prevent diffusion of excitons or holes to the electron transport layer 160, the organic light-emitting device 100 may include a hole blocking layer between the electron transport layer 160 and the emission layer 150. The hole blocking layer may include, for example, at least one an oxadiazole derivative, a triazole derivative, BCP, Bphen, BAlq, and HB1, but embodiments are not limited thereto:

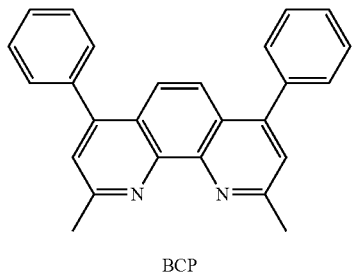

BCP

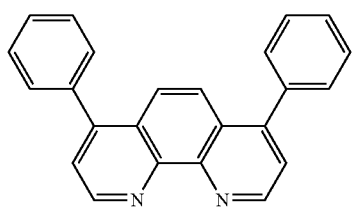

Bphen

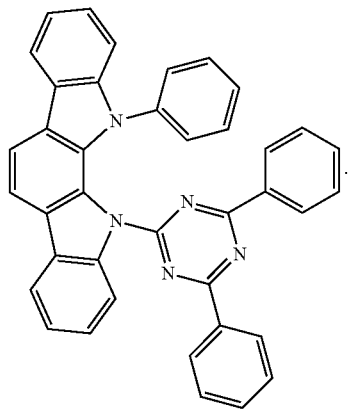

HB1

The thickness of the hole blocking layer may be in a range of about 20 Å to about 1,000 Å, and in some embodiments, about 30 Å to about 300 Å. When the thickness of the hole blocking layer is within any of these ranges, excellent hole blocking characteristics may be obtained without a substantial increase in driving voltage, The electron transport layer 160 may include tris(8-hydroxyquinolinato) aluminium ($Alq_3$); BAlq; a compound including a pyridine ring, e.g., 1,3,5-tri[(3-pyridyl)-phen-3-yl]benzene; a compound including a triazine ring, e.g., 2,4,6-tris(3'-(pyridin-3-yl)biphenyl-3-yl)-1,3,5-triazine; a compound including an imidazole ring, e.g., 2-(4-(N-phenylbenzimidazol-1-yl)-phenyl)-9,10-dinaphthylanthracene; a compound including a triazole ring, e.g., TAZ and NTAZ; 1,3,5-tris(N-phenyl-benzimidazol-2-yl)benzene (TPBi); BCP; Bphen; and the like:

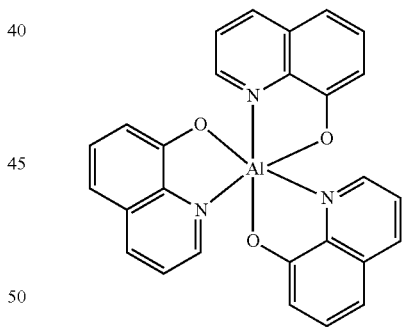

$Alq_3$

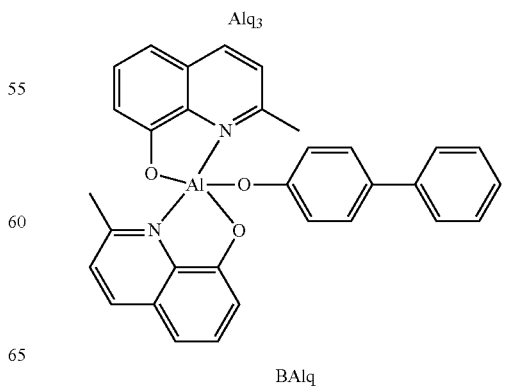

BAlq

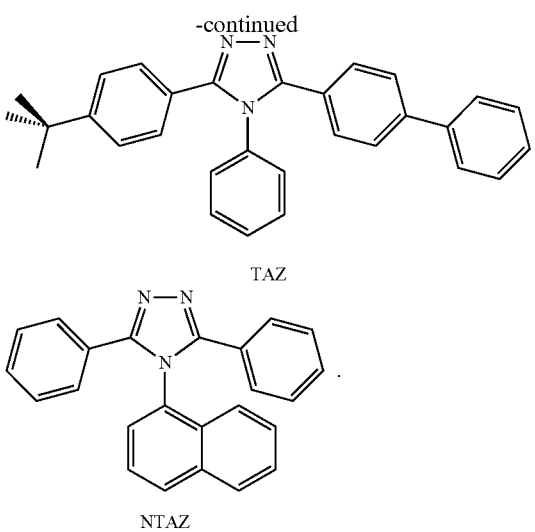

TAZ

NTAZ

The electron transport layer 160 may include commercially available products such as KLET-01, KLET-02, KLET-03, KLET-10, or KLET-M1 (available from Chemipro Kasei).

The electron transport layer 160 may further include a material containing metal, in addition to the materials described above.

The material containing metal may include a Li complex. The Li complex may include, e.g., Compound ET-D1 (LiQ) or Compound ET-D2:

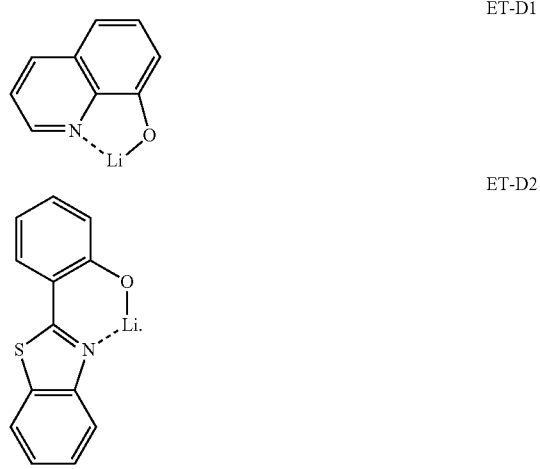

ET-D1

ET-D2

The electron transport layer 160 may be, for example, formed to a thickness in a range of about 15 nm to about 50 nm.

The electron injection layer 170 may be formed on the electron transport layer 160.

For example, the electron injection layer 170 may include a lithium compound, e.g., (8-hydroxyquinolinato)lithium (Liq) and lithium fluoride (LiF), sodium chloride (NaCl), cesium fluoride (CsF), lithium oxide ($Li_2O$), or barium oxide (BaO).

In some embodiments, the electron injection layer 170 may be formed to a thickness in a range of about 0.3 nm to about 9 nm.

The second electrode 180 may be formed on the electron injection layer 170. The second electrode 180 may be a cathode and be formed of a material with a relatively low work function such as a metal, an alloy, an electrically conductive compound, or a mixture thereof. For example, the second electrode 180 may be formed as a reflective electrode including a metal, e.g., lithium (Li), magnesium (Mg), aluminum (Al), or calcium (Ca), or an alloy, e.g., an aluminum-lithium (Al—Li) alloy, a magnesium-indium (Mg—In) alloy, or a magnesium-silver (Mg—Ag) alloy. In some embodiments, the second electrode 180 may be formed as a transparent electrode having a thickness of 20 nm or less and including a thin film of the metal or the alloy, or a transparent conductive film including indium tin oxide ($In_2O_3$—$SnO_2$) or indium zinc oxide ($In_2O_3$—$ZnO$).

Furthermore, a stacking structure of the organic light-emitting device 100 according to an embodiment is not limited to the foregoing description. The organic light-emitting device 100 according to an embodiment may have a different stacking structure known in the art. For example, the organic light-emitting device 100 may not include at least one selected from the hole injection layer 130, the hole transport layer 140, the electron transport layer 160, and the electron injection layer 170 or may further include another layer. In some embodiments, each layer of the organic light-emitting device 100 may be formed as a single layer or as multiple layers.

Methods of forming each layer of the organic light-emitting device 100 according to one or more embodiments are not particularly limited. For example, vacuum-deposition, solution coating, or Langmuir-blodgett (LB) deposition may be used in forming each layer thereof.

The solution coating may include spin coating, casting, micro-gravure coating, gravure coating, bar coating, roll coating, wire bar coating, dip coating, spray coating, screen printing, flexographic printing, offset printing, or ink-jet printing.

The solvent used in the solution coating may include toluene, xylene, methyl benzoate, diethyl ether; chloroform, ethyl acetate, dichloromethane, tetrahydrofuran, acetone, acetonitrile, N,N-dimethyl formamide, dimethyl sulfoxide, anisole, hexamethylphosphoric acid triamide, 1,2-dichloroethane, 1,1,2-trichloroethane, chlorobenzene, o-dichlorobenzene, dioxane, cyclohexane, n-pentane, n-hexane, n-heptane, n-octane, n-nonane, n-decane, methyl ethyl ketone, cyclohexanone, butyl acetate, ethyl acetate, ethyl cellosolve acetate, ethylene glycol, ethylene glycol monobutyl ether, ethylene glycol monoethyl ether, ethylene glycol monomethyl ether, dimethoxy ethane, propylene glycol, diethoxy methane, triethylene glycol monoethyl ether, glycerine, 1,2, hexanediol, methanol, ethanol, propanol, isopropanol, cyclohexanol, N-methyl-2-pyrrolidone, or any combination thereof. However, the solvent is not particularly limited. Any suitable solvent that may dissolve materials for forming each layer may be used.

In consideration of coatability or the like, a concentration of the composition may be about 0.1 percent by weight (wt %) or greater and 10 wt % or less, and more particularly, about 0.5 wt % or greater and 5 wt % or less, but embodiments are not limited thereto.

The vacuum deposition may be performed at a deposition temperature in a range of about 100° C. to about 500° C., at a vacuum pressure in a range of about $10^{-8}$ torr to about $10^{-3}$ torr, and at a deposition rate in a range of about 0.01 Angstroms per second (A/sec) to about 100 Å/sec, though the conditions may vary depending on a compound that is used and a structure and thermal properties of a desired layer.

In some embodiments, the first electrode 120 may be an anode, and the second electrode 180 may be a cathode.

For example, the first electrode 120 may be an anode, the second electrode 180 may be a cathode, and an organic layer may include the emission layer 150 between the first electrode 120 and the second electrode 180 and may further include a hole transport region between the first electrode 120 and the emission layer 150 and an electron transport region between the emission layer 150 and the second electrode 180, wherein the hole transport region may include at least one the hole injection layer 130, the hole transport layer 140, a buffer layer, and an electron blocking layer, and the electron transport region may include at least one a hole blocking layer, the electron transport layer 160, and the electron injection layer 170.

In some embodiments, the first electrode 120 may be a cathode, and the second electrode 180 may be an anode.

Hereinbefore the organic light-emitting device has been described with reference to FIG. 5, but embodiments are not limited thereto.

General Definitions of Substituents

The term "X and Y may each independently" as used herein may refer to that X may be identical to or different from Y.

The term "substituted" as used herein refers to that a hydrogen atom in a substituent such as $R_1$ may be substituted with another substituent.

The term "$C_1$-$C_{60}$ alkyl group" as used herein refers to a linear or branched aliphatic hydrocarbon monovalent group having 1 to 60 carbon atoms. Examples of the $C_1$-$C_{60}$ alkyl group include a methyl group, an ethyl group, an n-propyl group, an iso-propyl group, an n-butyl group, an isobutyl group, a sec-butyl group, a tert-butyl group, an n-pentyl group, an isopentyl group, a tert-pentyl group, a neopentyl group, a 1,2-dimethylpropyl group, an n-hexyl group, an iso-hexyl group, a 1,3-dimethylbutyl group, an 1-isopropylpropyl group, a 1,2-dimethylbutyl group, an n-heptyl group, a 1,4-dimethylpentyl group, a 3-ethylpentyl group, a 2-methyl-1-isopropylpropyl group, a 1-ethyl-3-methylbutyl group, an n-octyl group, a 2-ethylhexyl group, a 3-methyl-1-isopropylbutyl group, a 2-methyl-1-iso-propyl group, a 1-tert-butyl-2-methylpropyl group, an n-nonyl group, a 3,5,5-trimethyldecyl group, an n-decyl group, an iso-decyl group, an n-undecyl group, a 1-methyldecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-eicosyl group, an n-heneicosyl group, an n-docosyl group, an n-tricosyl group, and an n-tetracosyl group.

The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is a $C_1$-$C_{60}$ alkyl group). Examples of the $C_1$-$C_{60}$ alkoxy group include a methoxy group, an ethoxy group, a propoxy group, an iso-propoxy group, an n-butoxy group, an iso-butoxy group, a sec-butoxy group, a tert-butoxy group, an n-pentoxy group, an iso-pentoxy group, a tert-pentoxy group, a neopentoxy group, an n-hexyloxy group, an iso-hexyloxy group, a heptyloxy group, an octyloxy group, a nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a 2-ethylhexyloxy group, and a 3-ethylpentyloxy group.

The term "$C_1$-$C_{60}$ alkylthio group" as used herein refers to a monovalent group represented by —$SA_{102}$ (wherein $A_{102}$ is a $C_1$-$C_{60}$ alkyl group).

The term "$C_3$-$C_{30}$ cycloalkyl group" as used herein refers to a monovalent monocyclic saturated hydrocarbon group including 3 to 30 ring-forming carbon atoms. Examples thereof include a cyclopropyl group, a cyclobutyl group, a cyclopentyl group, a cyclohexyl group, and a cycloheptyl group. The term "$C_3$-$C_{30}$ cycloalkylene group" as used herein refers to a divalent group having the same structure as the $C_3$-$C_{30}$ cycloalkyl group.

The term "$C_6$-$C_{30}$ aryl group" as used herein refers to a monovalent group having a carbocyclic aromatic system having 6 to 30 ring-forming carbon atoms (when the $C_6$-$C_{30}$ aryl group is substituted with a substituent, the carbon atom included in the substituent may not be counted as a ring-forming carbon atom). The term "$C_6$-$C_{30}$ arylene group" as used herein refers to a divalent group having a carbocyclic aromatic system having 6 to 30 carbon atoms. Examples of the $C_6$-$C_{30}$ aryl group include a phenyl group, a naphthyl group, an anthracenyl group, a phenanthrenyl group, a pyrenyl group, and a chrysenyl group. When the $C_6$-$C_{30}$ aryl group and the $C_6$-$C_{30}$ arylene group each independently include two or more rings, the respective rings may be fused.

The term "$C_6$-$C_{30}$ aryloxy group" as used herein refers to a group represented by —$OA_{103}$ (wherein $A_{103}$ is a $C_6$-$C_{30}$ aryl group). Examples of the $C_6$-$C_{30}$ aryloxy group include a 1-naphthyloxy group, a 2-naphthyloxy group, and a 2-azulenyloxy group.

The term "$C_6$-$C_{30}$ arylthio group" as used herein refers to a group represented by —$SA_{104}$ (wherein $A_{104}$ is a $C_6$-$C_{30}$ aryl group).

The term "$C_1$-$C_{30}$ heteroaryl group" as used herein refers to a monovalent group having a heterocyclic aromatic system having at least one heteroatom selected from N, O, Si, P, B, Se, Ge, or S as a ring-forming atom and 1 to 30 ring-forming carbon atoms. The term "$C_1$-$C_{30}$ heteroarylene group" as used herein refers to a divalent group having a heterocyclic aromatic system having at least one heteroatom N, O, Si, P, B, Se, Ge, or S as a ring-forming atom and 1 to 30 ring-forming carbon atoms. Examples of the $C_1$-$C_{ao}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{30}$ heteroaryl group and the $C_1$-$C_{30}$ heteroarylene group each independently include two or more rings, the respective rings may be fused.

The term "$C_1$-$C_{30}$ heteroaryloxy group" as used herein refers to a group represented by —$OA_{105}$ (wherein $A_{105}$ is a $C_1$-$C_{30}$ heteroaryl group). Examples of the $C_1$-$C_{30}$ heteroaryloxy group include a 2-furanyloxy group, a 2-thienyloxy group, a 2-indolyloxy group, a 3-indolyloxy group, a 2-benzofuryloxy group, and a 2-benzothienyloxy group.

The term "$C_1$-$C_{30}$ heteroarylthio group" as used herein refers to a group represented by —$SA_{106}$ (wherein $A_{106}$ is a $C_1$-$C_{30}$ heteroaryl group).

The term "$C_7$-$C_{30}$ arylalkyl group" as used herein refers to a monovalent group in which an alkylene group is substituted with an aryl group. The total number of carbon atoms forming the alkylene group and the aryl group may be in a range of 7 to 30. Examples of the $C_7$-$C_{30}$ aryl alkyl group include a benzyl group, a phenylethyl group, a phenylpropyl group, and a naphthylmethyl group.

The term "$C_7$-$C_{30}$ aryl alkyloxy group" as used herein refers to a group represented by —$OA_{105}$ (wherein $A_{105}$ is a $C_7$-$C_{30}$ aryl alkyl group).

The term "$C_7$-$C_{30}$ aryl alkylthio group" as used herein refers to a group represented by —$SA_{106}$ (wherein $A_{106}$ is a $C_7$-$C_{30}$ aryl alkyl group).

The term "$C_8$-$C_{30}$ aryl alkenyl group" as used herein refers to a monovalent group in which an alkenylene group is substituted with an aryl group. The total number of carbon atoms forming the alkenylene group and the aryl group may be in a range of 8 to 30.

The term "$C_8$-$C_{30}$ aryl alkynyl group" as used herein refers to a monovalent group in which an alkynylene group is substituted with an aryl group. The total number of carbon atoms forming the alkynylene group and the aryl group may be in a range of 8 to 30.

The term "monovalent non-aromatic condensed polycyclic group" as used herein refers to a monovalent group that has two or more condensed rings and only carbon atoms (e.g., the number of carbon atoms may be in a range of 8 to 60) as ring-forming atoms, wherein the molecular structure as a whole is non-aromatic. Examples of the monovalent non-aromatic condensed polycyclic group include a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group that has two or more condensed rings, and at least one heteroatom N, O, P, Si, B, Se, Ge, or S and carbon atoms (e.g., the number of carbon atoms may be in a range of 1 to 60) as ring-forming atoms, wherein the molecular structure as a whole is non-aromatic. Examples of the monovalent non-aromatic condensed heteropolycyclic group include a carbazolyl group. The term "divalent non-aromatic condensed heteropolycyclic group" as used herein refers to a divalent group having substantially the same structure as the monovalent non-aromatic condensed heteropolycyclic group.

The term "$C_5$-$C_{30}$ carbocyclic group" as used herein refers to a saturated or unsaturated cyclic group including 5 to 30 carbon atoms only as ring-forming atoms. The $C_5$-$C_{30}$ carbocyclic group may be a monocyclic group or a polycyclic group. Depending on formula structure, the $C_5$-$C_{30}$ carbocyclic group may be monovalent, divalent, trivalent, quadrivalent, pentavalent, or hexavalent.

The term "$C_1$-$C_{30}$ heterocyclic group" as used herein refers to saturated or unsaturated cyclic group including 1 to 30 carbon atoms and at least one heteroatom N, O, P, Si, B, Se, Ge, or S as ring-forming atoms. The $C_1$-$C_{30}$ heterocyclic group may be a monocyclic group or a polycyclic group. Depending on formula structure, the $C_1$-$C_{30}$ heterocyclic group may be monovalent, divalent, trivalent, quadrivalent, pentavalent, or hexavalent.

In the present specification, at least one substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group and the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, or any combination thereof;

a $C_1$-$C_{60}$ alkyl group a $C_2$-$C_{60}$ alkenyl group, a ($C_2$-$C_{60}$ alkynyl group, a $C_1$-$C_{60}$ alkoxy group, or any combination thereof, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$ —$Si(Q_{13})(Q_{14})(Q_{15})$, —$B(Q_{16})(Q_{17})$, —$P(=O)(Q_{18})(Q_{19})$, or any combination thereof, a $C_3$-$C_{10}$ cycloalkyl group, a $C_1$-$C_{10}$ heterocycloalkyl group, a $C_3$-$C_{10}$ cycloalkenyl group, a $C_1$-$C_1$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or any combination thereof:

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or any combination thereof, each substituted with at least one deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, —$P(=O)(Q_{26})(Q_{29})$, or any combination thereof; or —$N(Q_{31})(Q_{32})$, —$Si(Q_{33})(Q_{34})(Q_{35})$, —$B(Q_{36})(Q_{37})$, —$P(=O)(Q_{38})(Q_{39})$, or any combination thereof, wherein $Q_{11}$ to $Q_{19}$, $Q_{21}$ to $Q_{29}$, and $Q_{31}$ to $Q_{39}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one a $C_1$-$C_{60}$ alkyl group or a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group.

The term "A to B" as used herein refers to a range from A to B including A and B.

Hereinafter, with reference to Examples and Comparative Examples, the heterocyclic compound represented by Formula 1 and an organic light-emitting device including the heterocyclic compound will be further described. However, these Examples are illustrative purposes only, and thus the heterocyclic compound and the organic light-emitting device according to an embodiment is not limited thereto.

The wording "B was used instead of A" used in describing Synthesis Examples means that an identical molar equivalent of B was used in place of A.

Also, unless otherwise described, "%" is based on a weight.

EXAMPLES

Synthesis Example 1: Synthesis of Compound 1

(1) Synthesis of Intermediate 1a

Intermediate 1a was synthesized based on the following Reaction Scheme:

Under nitrogen atmosphere, 220 mmol (42 g) of 4-bromochlorobenzene, 231 mmol (45.7 g) of biphenyl-3-boronic acid (1.05 eq.), 880 mL of toluene, and 110 mL of ethanol (EtOH) were added to a three-neck flask, followed by stirring for preparation of a solution. Subsequently, 165 mL (1.5 eq.) of 2 M potassium carbonate aqueous solution ($K_2CO_3$ 2 M aq.) was added to this solution, and then 6.6 mmol (7.63 g) of $Pd(PPh_3)_4$ (tetrakis(triphenylphosphine) palladium (0)) (3 mol %) was added and stirring was performed at 70° C. for 8 hours. Next, the reaction solution was diluted using 500 mL of toluene and filtered using a Celite filter, followed by washing with pure water twice. The organic layer was dried using anhydrous magnesium sulfate, filtered through a silica gel pad, and concentrated. The resulting crude was dispersed in and washed with EtOH (10 mL/1 g), filtered, vacuum-dried (at 50° C., for 12 hours), thereby obtaining a white solid product (Intermediate 1a). The obtained amount of Intermediate 1a was 57.7 g, and a yield thereof was 99%.

Subsequently, Intermediate 1b was synthesized based on the following Reaction Scheme:

(2) Synthesis of Intermediate 1b

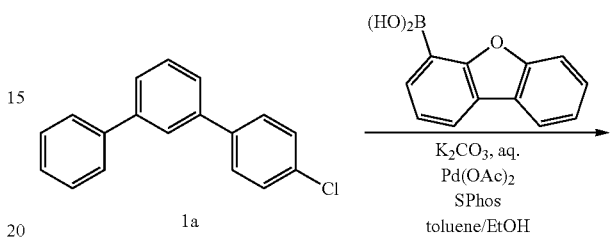

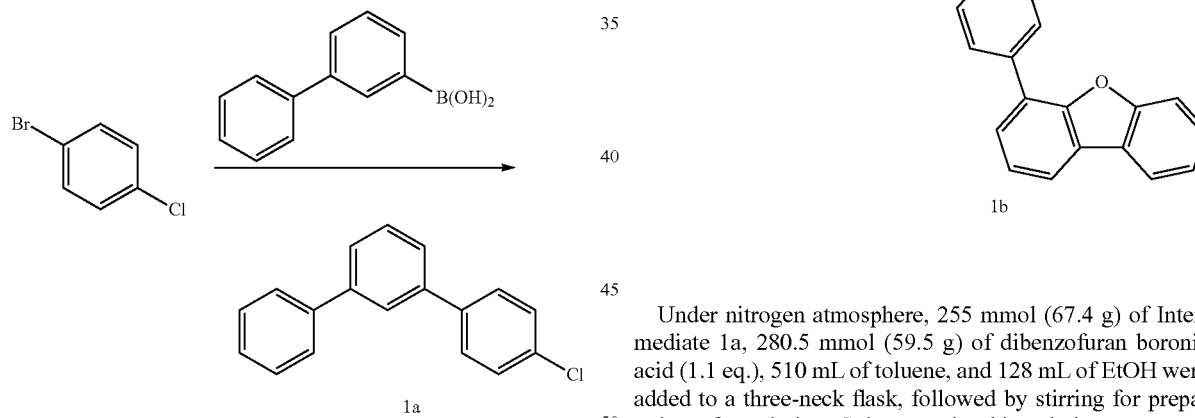

Under nitrogen atmosphere, 255 mmol (67.4 g) of Intermediate 1a, 280.5 mmol (59.5 g) of dibenzofuran boronic acid (1.1 eq.), 510 mL of toluene, and 128 mL of EtOH were added to a three-neck flask, followed by stirring for preparation of a solution. Subsequently, this solution was combined with 191 mL of 2M $K_2CO_3$ (aq.), 7.65 mmol (1.71 g) of acetate palladium (3 mol %), and 11.5 mmol (4.72 g) of S-phos(2-dicyclohexylphosphino-2',6'-dimethoxybiphenyl) (4.5 mol %), followed by stirring at 80° C. for 6 hours. The resulting solution was cooled to room temperature, and the reaction solution was diluted using 1 L of methanol, followed by ultrasonic irradiation for 30 minutes. Then, a solid precipitated from the diluted solution was recovered by filtration and washed with methanol. After the washing, the precipitated solid was vacuum-dried (at 50° C. for 12 hours), heated and dissolved in 1 L of toluene, filtered using a silica gel pad, and concentrated. The obtained crude was recrystallized twice using a mixed solvent of toluene and ethanol (at a ratio of 6 mL to 10 mL/1 g), thereby obtaining a white solid product (Intermediate 1b). The obtained amount of Intermediate 1b was 72.8 g, and a yield thereof was 72%.

Subsequently, Intermediate 1c was synthesized based on the following Reaction Scheme:

(3) Synthesis of Intermediate 1c

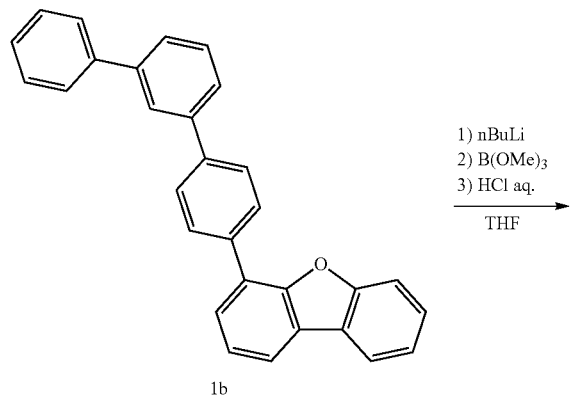

183 mmol (72.2 g) of Intermediate 1b and 1,830 mL of tetrahydrofuran were added to a three-neck flask and stirred to prepare a solution. Subsequently, this solution was cooled to 0° C., and 201.3 mmol (76 mL) of nBuLi hexane solution (n-butyl lithium/hexane solution, 2.65 M, 1.1 eq.) was added thereto. Accordingly, the color of the solution changed from colorless to dark blue. The solution was stirred at 0° C. for 2 hours. Next, 237.9 mmol (26.6 mL) of trimethyl borate (1.3 eq.) was added dropwise to the solution. Accordingly, the color of the solution changed from dark blue to light blue. The solution was stirred at room temperature for 5 hours. The reaction system was then quenched using methanol, and pure water was added thereto. The obtained solution was concentrated to about half volume, and acidified with 600 mL of 1N hydrochloric acid aqueous solution. The organic phase was then extracted with ethyl acetate in a separatory funnel and washed twice with pure water. After washing, this extracted organic phase was dried using anhydrous magnesium sulfate, filtered through a silica gel pad, and concentrated. The obtained crude was vacuum-dried (at 50° C. for 12 hours), and heated and dissolved in 500 mL of toluene. Then, 1 L of hexane was added thereto to precipitate a solid, and then dispersing and washing were performed (under reflux for 4 hours). The resulting mixture was cooled to room temperature, and a precipitated solid was recovered by filtration, thereby obtaining a white solid product (Intermediate 1c). The obtained amount of Intermediate 1c was 80.6 g, and a yield thereof was 75%.

Subsequently, Intermediate 1d was synthesized based on the following Reaction Scheme:

(4) Synthesis of Intermediate 1d

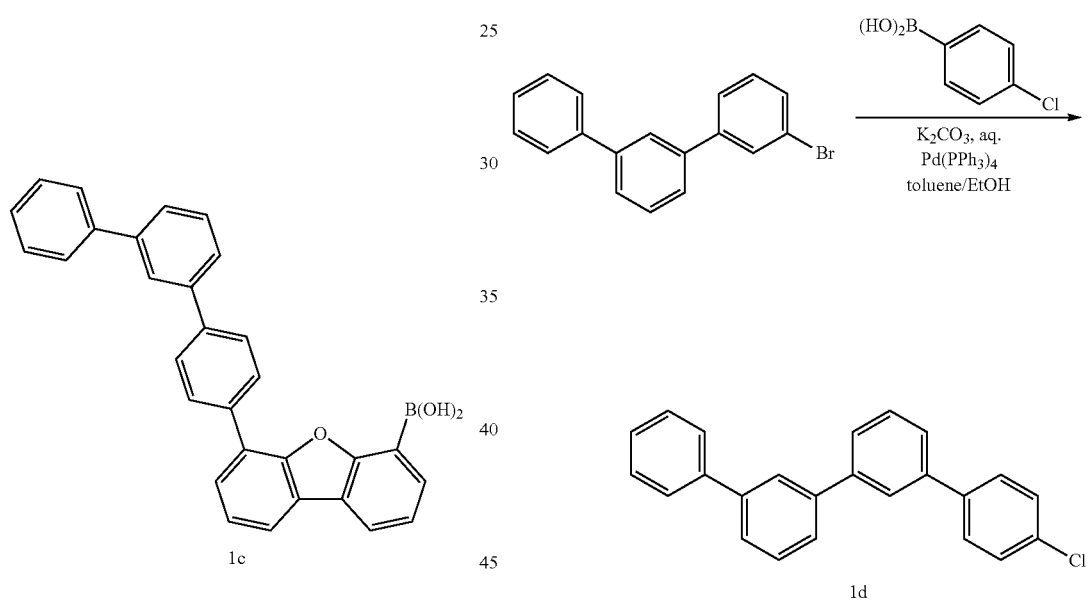

Under nitrogen atmosphere, 1 mol (309.2 g) of 3-bromo-1,1': 3'1"-terphenyl, 1.05 mol (164.2 g) of 4-chlorophenyl boronic acid (1.1 eq.), 2 L of toluene, and 200 mL of EtOH were added to a three-neck flask, followed by stirring for preparation of a solution. Subsequently, 750 mL (1.5 eq.) of 2 M $K_2CO_3$ (aq.) was added to this solution, followed by addition of 30 mmol (34.7 g) of $Pd(PPh_3)_4$ and stirring at 70° C. for 12 hours. Next, the reaction solution was cooled to room temperature and filtered using a Celite filter, followed by washing with pure water twice. After washing, the organic layer was dried using anhydrous magnesium sulfate, filtered through a silica gel pad, and concentrated. The obtained crude was recrystallized three times using a mixed solvent of toluene and hexane (at a ratio of 2 mL to 10 mL/1 g), thereby obtaining a white solid product (Intermediate 1d). The obtained amount of Intermediate 1d was 153.7 g, and a yield thereof was 45%.

Thereafter, Compound 1 was synthesized based on the following Reaction Scheme:

(5) Synthesis of Compound 1

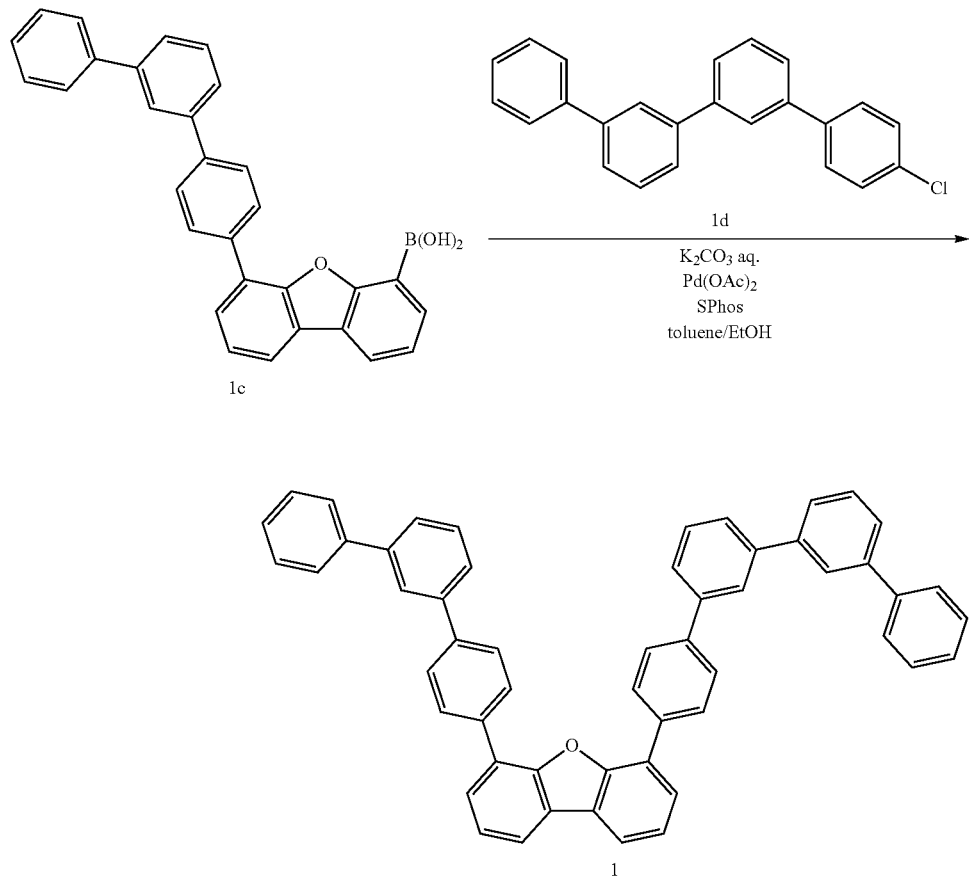

Under nitrogen atmosphere, 15 mmol (6.6 g) of Intermediate 1c, 16.5 mmol (5.6 g) of Intermediate 1d (1.05 eq.), 150 mL of toluene, and 15 mL of EtOH were added to a three-neck flask, followed by stirring for preparation of a solution. Subsequently, this solution was added with 11.3 mL (1.5 eq.) of 2 M $K_2CO_3$ (aq.), 0.45 mmol (101 mg) of palladium (II) acetate (3 mol %), and 0.68 mmol (279 mg) of S-phos (4.5 mol %), followed by stirring at 80° C. for 6 hours. The reaction solution was cooled to room temperature, diluted using 200 mL of methanol, followed by ultrasonic irradiation for 30 minutes, and the precipitated solid was recovered by filtration, and the solid was washed with methanol. After the washing, the precipitated solid was vacuum-dried (at 50° C. for 12 hours), heated and dissolved in 300 mL of toluene, filtered using a silica gel pad, and concentrated. The obtained crude was dispersed and washed three times using a mixed solvent of toluene and ethanol (at a ratio of 6 mL to 10 mL/1 g), thereby obtaining a white solid product (Compound 1). The obtained amount of Compound 1 was 8.9 g, and a yield thereof was 85%.

Synthesis Example 2: Synthesis of Compound 2

(1) Synthesis of Intermediate 2a

Intermediate 2a was synthesized based on the following Reaction Scheme:

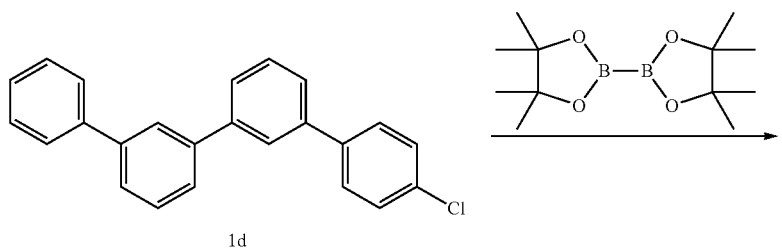

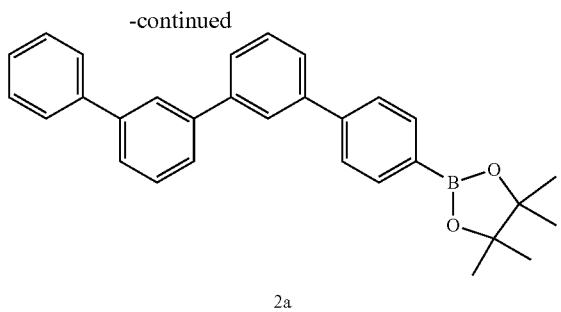

2a

Under nitrogen atmosphere, 129 mmol (44.0 g) of Intermediate 1d, 142 mmol (36.1 g) of bis(pinacolato)diboron (1.05 eq.), 258 mmol (25.3 g) of potassium acetate (2 eq.), and 258 mL of 1,4-dioxane were added to a three-neck flask, followed by stirring to prepare a dispersion. Subsequently, 2.58 mmol (579 mg) of palladium (II) acetate (2 mol %) and 5.16 mmol (2.46 g) of X-phos (2-dicyclohexylphosphino-2',4',6'-triisopropylbiphenyl) (4 mol %) were added to this dispersion, followed by stirring at 80° C. for 10 hours. Next, the reaction solution was cooled to room temperature, diluted using 300 mL of toluene, and filtered using a Celite filter, followed by washing with pure water three times. After washing, the organic layer was dried using anhydrous magnesium sulfate, filtered through a silica gel pad, and concentrated. The obtained crude was recrystallized using hexane (at a ratio of 10 mL/1 g) and vacuum-dried (at 50° C. for 12 hours) thereby obtaining a white solid product (Intermediate 2a). The obtained amount of Intermediate 2a was 43.9 g, and a yield thereof was 79%.

Thereafter, Compound 2 was synthesized based on the following Reaction Scheme:

(2) Synthesis of Compound 2

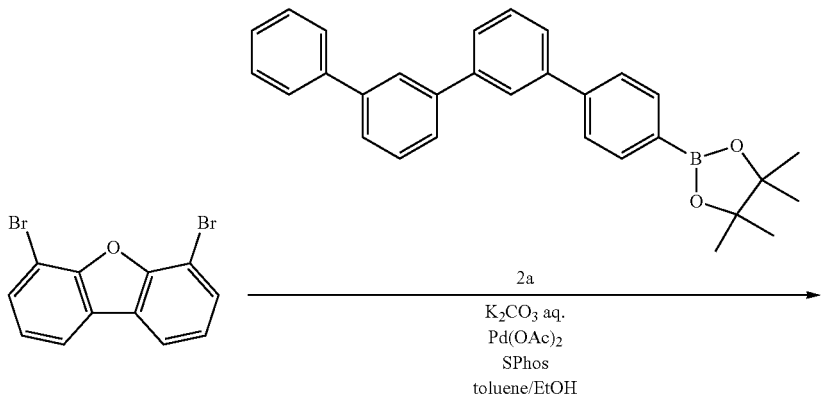

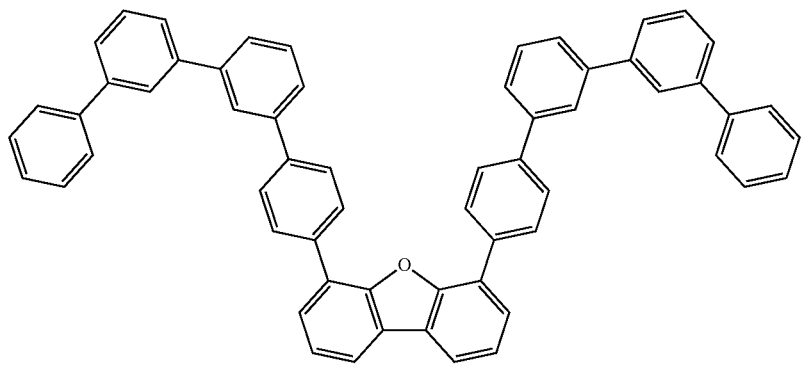

2

Under nitrogen atmosphere, 15 mmol (4.9 g) of 4,6-dibromodibenzofuran, 33.0 mmol (14.3 g) of Intermediate 2a (2.2 eq.), 150 mL of toluene, and 15 mL of EtOH were added to a three-neck flask, followed by stirring for preparation of a solution. Subsequently, 11.3 mL (1.5 eq.) of 2 M $K_2CO_3$ (aq.) was added to this solution, followed by addition of 4.5 mmol (5.20 g) of Pd(PPh$_3$)$_4$ and stirring at 70° C. for 8 hours. The reaction solution was cooled to room temperature, diluted using 200 mL of methanol, followed by ultrasonic irradiation for 30 minutes, filtration of the precipitated solid, and washing the precipitated solid with methanol. After the washing, the precipitated solid was vacuum-dried (at 50° C. for 12 hours), heated and dissolved in 500 mL of toluene, filtered using a silica gel pad, and concentrated. The obtained crude was recrystallized twice using a mixed solvent of toluene and ethanol (at a ratio of 10 mL to 5 mL/1 g), thereby obtaining a white solid product (Compound 2). The obtained amount of Compound 2 was 7.6 g, and a yield thereof was 65%.

Synthesis Example 3: Synthesis of Compound 11

Compound 11 was synthesized based on the following Reaction Scheme:

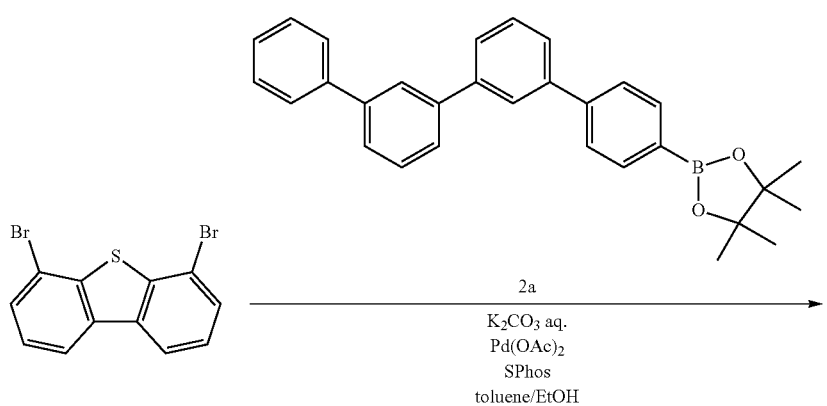

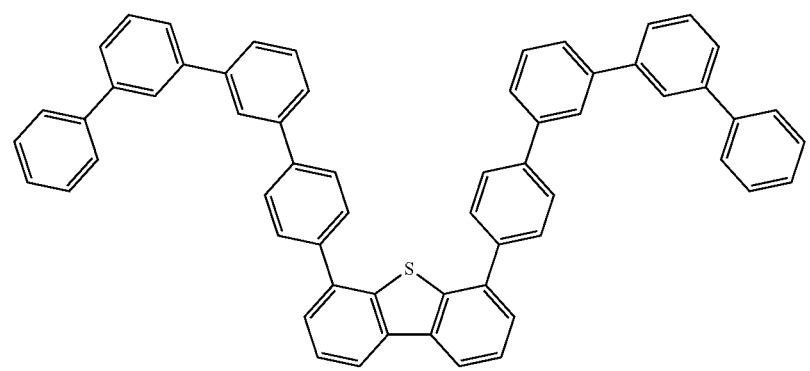

11

Compound 11 was synthesize in substantially the same manner as in Synthesis of Compound 2, except that 4,6-dibromodibenzothiophene was used instead of 4,6-dibromodibenzofuran. The obtained amount of Compound 11 was 6.2 g, and a yield thereof was 52%.

Compounds of the present invention other than Compounds 1, 2, and 11 may also be synthesized in the same or similar manner or further with reference to a method known in the art.

Evaluation of Compounds

Evaluation of Solubility

The obtained Compounds 1, 2, 11 and Comparative Examples Compounds C1 to C3 were each prepared as sample solids.

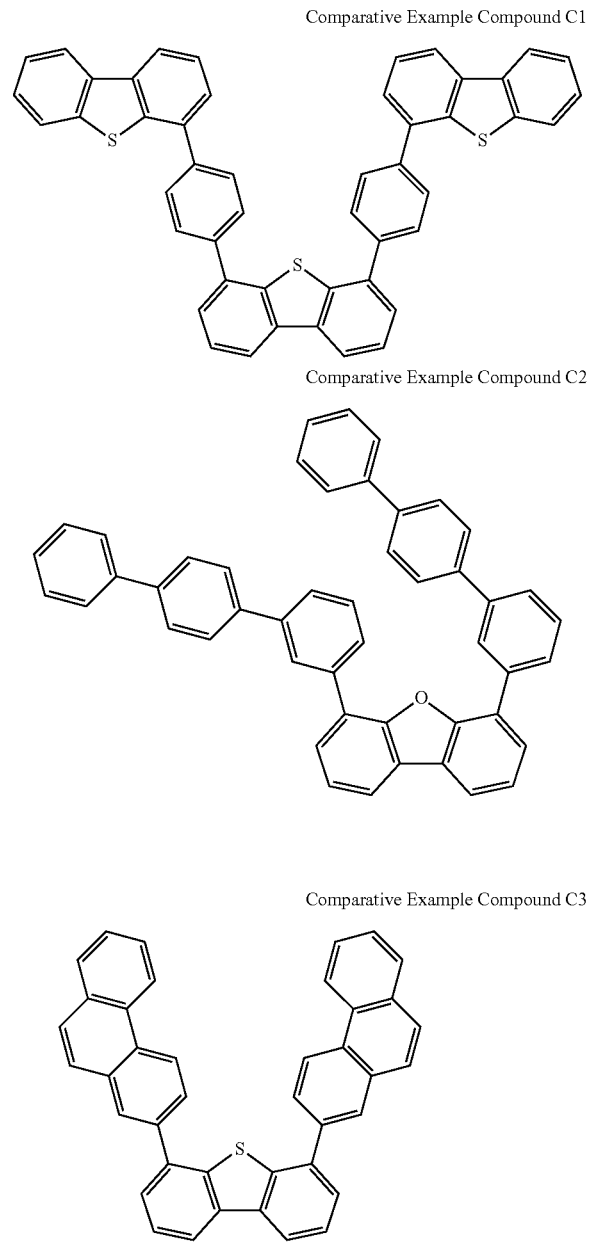

50 mg of the sample solid was added to a colorless sample bottle, and 500 mg of methyl benzoate was added as a solvent thereto, followed by ultrasonic irradiation for 20 minutes at room temperature, thereby observing with the naked eye whether the sample solid remained or not. When the sample solid remained, the solvent was added thereto, followed by repetition of ultrasonic irradiation for complete dissolution. By measuring the amount of the solvent at this point, the solubility was calculated. The results of evaluation are shown in Table 1.

Evaluation of Pot Life of Solution

The obtained Compounds 1, 2, 11 and Comparative Examples Compounds C1 to C3 were each prepared as sample solids.

50 mg of the sample solid was added to a colorless sample bottle, and 1.0 g of methyl benzoate was added as a solvent thereto, followed by heating at 150° C. and complete dissolving the sample solid. Therefore, a 5 wt % methyl benzoate solution was prepared. Next, the solution was cooled to room temperature, and observation was started. Then, the time (hour, h) took for confirming occurrence of solid precipitation. e.g., crystals, with the naked eye was determined as a pot life. That is, as a pot life was longer, crystallization was more difficult. The results of measurement are shown in Table 1.

TABLE 1

| Compound | Solubility in methyl benzoate at room temperature (wt %) | Pot life of 5 wt % methyl benzoate solution (h) |
| --- | --- | --- |
| Compound 1 | 6 | >300 |
| Compound 2 | 1.5 | 20 |
| Compound 11 | 1.5 | 20 |
| Comparative Example Compound C1 | 0.1 | <0.1 |
| Comparative Example Compound C2 | 0.5 | 1 |
| Comparative Example Compound C3 | 0.2 | <0.1 |

Measurement of HOMO value and LUMO value

The obtained Compounds 1, 2, 11 and Comparative Examples Compounds C1 to C3 were each prepared as sample solids. Next, the HOMO and LUMO values were measured as follows.

1. Preparation of Measurement Sample (1) A sample solution was prepared such that a sample solid was 4 parts by weight based on 100 parts by weight of methyl benzoate as a solvent.

(2) The sample solution prepared in Section 1.(1) was coated on each of an ITO substrate and a quartz substrate by a spin-coating method to form a coating film having a dry film thickness of 50 nm. The resulting coating film was heated under a vacuum pressure of $10^{-1}$ Pa or lower at 120° C. for 1 hour. Then, under vacuum pressure of 10-Pa or lower, the coating film was cooled to room temperature to form a thin film layer (thin film sample)

2. Measurement of HOMO Value

The HOMO value of each compound was measured using the thin film sample on the ITO substrate prepared in Section 1.(2) by a photoelectron spectrometer AC-3 (available from Riken Keiki).

3. Measurement of LUMO Value

An energy gap value ($E_g$) at an absorption end of ultraviolet-visible absorption spectrum was measured using the thin film sample on the quartz substrate prepared in Section 1.(2) by a spectrophotometer U-3900 (available from Hitachi High-Technologies), and the LUMO value was calculated by Mathematical Equation 3.

$$LUMO = HOMO + E_g \qquad \text{Mathematical Equation 3}$$

The calculation results are shown in Table 2.

Measurement of Glass Transition Temperature ($T_g$)

The obtained Compounds 1, 2, 11 and Comparative Examples Compounds C1 to C3 were each prepared as sample solids. In addition, each of an azine ring derivative Az1, a phosphorescence-emitting platinum group metal complex D1, and carbazole derivatives H1-1, H2-34, and H3-3 were prepared as a sample solid used in preparation of the following organic light-emitting device.

Subsequently, a differential scanning calorimeter DSC6220 (available from Seiko) was used to scan and measure the sample solid of about 5 mg for three times. Here, under measurement conditions, a heating rate was 10° C./min in a range of −50° C. to 300° C., and a cooling rate was −50° C./min in a range of 300° C. to −50° C. The glass transition temperature ($T_g$) was measured from the second and subsequent scanning calorie curves. The results of measurement are shown in Table 2.

TABLE 2

| Compound | HOMO (eV) | LUMO (eV) | $T_g$ (° C.) |
| --- | --- | --- | --- |
| Compound 1 | −6.2 | −2.7 | 80 |
| Compound 2 | −6.2 | −2.8 | 94 |
| Compound 11 | −6.1 | −2.8 | 103 |
| Az1 | −5.9 | −3.0 | 125 |
| D1 | −5.4 | −2.9 | — (no measurement) |
| H2-34 | −5.6 | −2.3 | 115 |
| H1-1 | −5.8 | −2.6 | 108 |
| H3-3 | −6.0 | −3.0 | 95 |

TABLE 2-continued

| Compound | HOMO (eV) | LUMO (eV) | $T_g$ (° C.) |
| --- | --- | --- | --- |
| Comparative Example Compound C1 | −6.1 | −2.8 | 146 |
| Comparative Example Compound C2 | −6.2 | −2.7 | 78 |
| Comparative Example Compound C3 | −6.1 | −2.9 | 117 |

Preparation of organic light-emitting device and Evaluation 1
Preparation of organic light-emitting device Example 1

Example 1

First: on a glass substrate on which an ITO anode (as a first electrode) in a stripe form was deposited to a thickness of 150 nm, PEDOT/PSS (available from Sigma-Aldrich Co.; Ltd.) was coated by spin coating and dried to form a film of a hole injection layer having a thickness of 30 nm.

Next, a hole transport layer coating solution was prepared on the hole injection layer, wherein the hole transport layer coating solution included anisole as a solvent, 3 parts by weight of a hole transporting polymer (HTP1, weight average molecular weight $M_w$=400,000, PDI ($M_w/M_n$)=2.7) having the repeating unit represented by the following Formula based on 100 parts by weight of the solvent, and 0.6 parts by weight of a low molecular weight Compound AD1 based on 100 parts by weight of the solvent. Subsequently, the resulting hole transport layer coating solution was coated on the hole injection layer by a spin-coating method to form a coating film such that a thickness of the dry film was 125 nm. The resulting coating film was heated under vacuum pressure of $10^{-1}$ Pa or lower at 230° C. for 1 hour. Then, under vacuum pressure of $10^{-1}$ Pa or lower, the coating film was cooled to room temperature to form a hole transport layer.

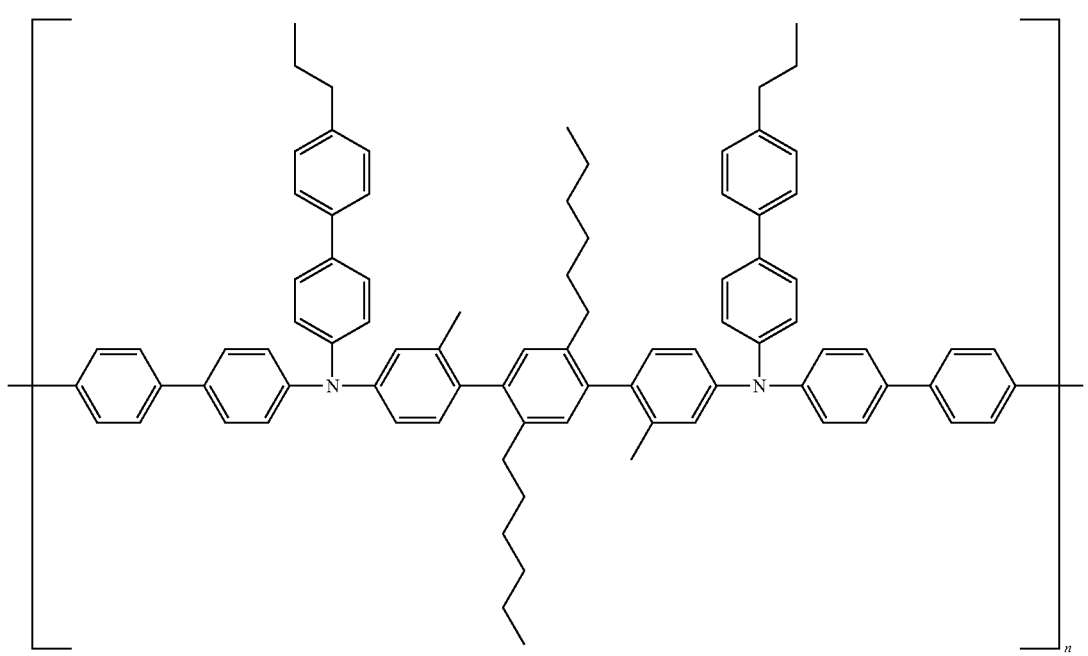

HTP1

-continued

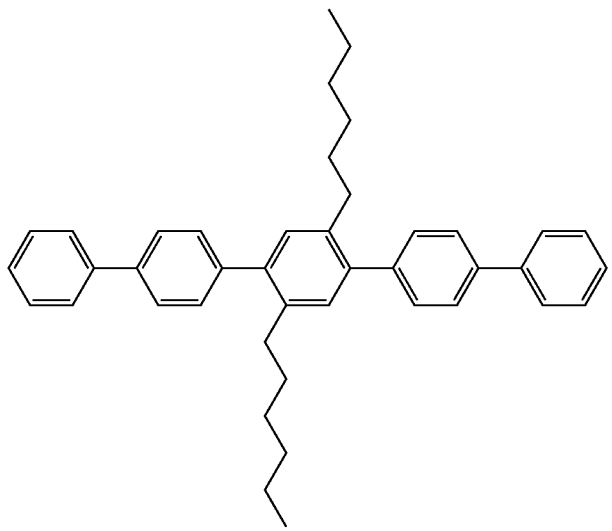

Subsequently, an ink for an emission layer (a methyl benzoate solution that is a composition including Compound 1 and Compound Az1 as host materials and Compound D1 (tris(2-(3-p-xylyl)phenylpyridine) iridium, TEG) as dopant materials), i.e., a liquid composition, was coated on the hole transport layer by a spin-coating method to form a dry film having a thickness of 30 nm, thereby forming an emission layer on the hole transport layer. The ink for an emission layer was prepared to include, as solid materials, 3.2 parts by weight of Compound 1, 0.8 parts by weight of Compound Az1, and 0.4 parts by weight of Compound D1, based on 100 parts by weight of a solvent, i.e., methyl benzoate.

Compound 1

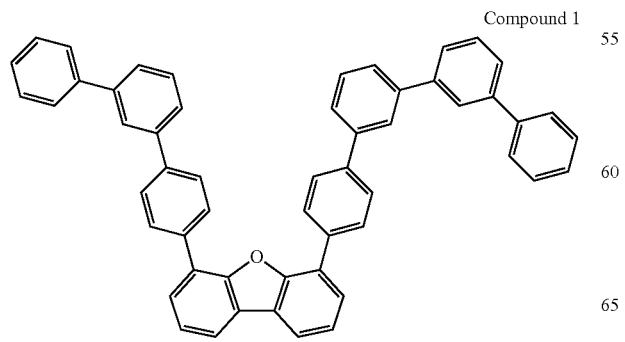

-continued

Az1

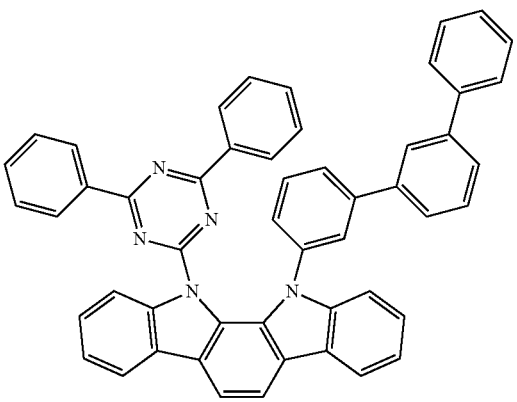

D1

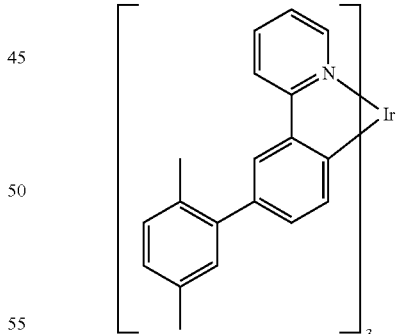

Liq

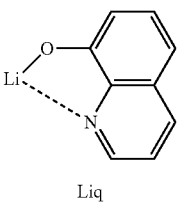

Next, (8-hydroxyquinolinato)lithium (Liq) and KLET-03 (available from Chemipro Kasei) were co-deposited at a weight ratio of 2:8 on the emission layer using a vacuum deposition apparatus to form an electron transport layer having a thickness of 30 nm.

Lithium fluoride (hereinafter, referred to as LiF) was deposited on the electron transport layer using a vacuum deposition apparatus to form an electron injection layer having a thickness of 1 nm.

Further, aluminum was deposited on the electron injection layer using a vacuum deposition apparatus to form a second electrode (cathode) having a thickness of 100 nm.

Then, a sealed organic light-emitting device was fabricated using a glass sealant tube containing a desiccant and an ultraviolet curable resin in a glove box under nitrogen atmosphere at a moisture concentration of 1 part per million (ppm) or less, and at an oxygen concentration of 1 ppm or less.

Examples 2 and 3 and Comparative Examples 1 to 4

Organic light-emitting devices were prepared in substantially the same manner as in Example 1, except that the composition of an ink for an emission layer was changed as shown in Table 3 below.

Evaluation of Organic Light-Emitting Device

According to the following method, the driving voltage, current efficiency, and emission lifespan (durability) were evaluated.

A continuously changing voltage from 0 volts (V) to 20 V was applied to the organic light-emitting device by using a direct-current constant-voltage power source (a source meter available from KEYENCE Co., Ltd,) so that the organic light-emitting device emits light. The luminance was measured by a luminance meter (SR-3 available from Topcom). A voltage at which the luminance is 1,000 cd/m$^2$ is determined as the driving voltage.

Then, a value of current per unit area (current density) of the organic light-emitting device when the luminance of the organic light-emitting device is 1,000 cd/m$^2$ was calculated, and the luminance (cd/m$^2$) was divided by the current density (A/m$^2$) to calculate the current efficiency (cd/A). In addition, the current efficiency indicates efficiency (conversion efficiency) of converting current into emission energy, and a higher current efficiency may result in better performance of an organic light-emitting device.

The lifespan (durability. LT80 (h)) indicates a time (hour) taken for the luminance to decline to 80% of initial luminance, wherein the luminance decreased over the continuous driving hours from the current of 6,000 cd/lm.

The results of evaluation are shown in Table 3. In Table 3, the current efficiency is shown as a relative value when the current efficiency of the organic light-emitting device of Comparative Example 2 is 100. The lifespan (durability) is shown as a relative value when the device lifespan of the organic light-emitting device of Comparative Example 2 is 100. Also, "*1" indicates that measurement was not possible because an organic light-emitting device was not prepared.

TABLE 3

| | Emission layer composition | Driving voltage (V) @1,000 cd/m$^2$ | Current efficiency (relative value) @1,000 cd/m$^2$ | Emission lifespan (relative value) |
|---|---|---|---|---|
| Example 1 | Compound 1:Az1:D1 (80:20:10) | 8.8 | 141 | 670 |
| Example 2 | Compound 2:Az1:D1 (80:20:10) | 8.8 | 138 | 645 |
| Example 3 | Compound 11:Az1:D1 (80:20:10) | 8.7 | 145 | 710 |
| Comparative Example 1 | Compound C1:Az1:D1 (80:20:10) | *1 | *1 | *1 |
| Comparative Example 2 | H2-34:Az1:D1 (80:20:10) | 4.7 | 100 | 100 |
| Comparative Example 3 | Compound C2:Az1:D1 (80:20:10) | *1 | *1 | *1 |
| Comparative Example 4 | Compound C3:Az1:D1 (80:20:10) | *1 | *1 | *1 |

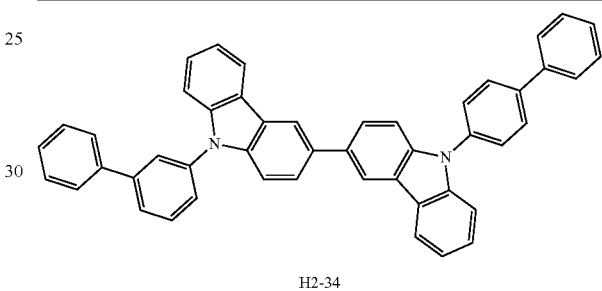

H2-34

As shown in Tables 1 and 3, the solubilities of Comparative Example Compounds C1 to C3, were deficient. Thus, it was found that an organic light-emitting device was not prepared by a coating method (Comparative Examples 1, 3, and 4).

As shown in Table 3, when the compound according to the present disclosure and an azine ring derivative, Compound Az1 were together used as host materials, as compared with a case of using a combination of a carbazole derivative, Compound H2-34 (which is commonly used as a hole transporting host material as in Comparative Example 2) and the azine ring derivative, Compound Az1, it was confirmed that luminescence efficiency and emission lifespan were remarkably superior.

Preparation of Organic Light-Emitting Device and Evaluation 2

Example 4

An organic light-emitting device was prepared in substantially the same manner as in Example 1, except that the ink for an emission layer was prepared to include, as solid materials, 1.33 parts by weight of Compound 1, 1.33 parts by weight of Compound H2-34, 1.33 parts by weight of Compound Az1, and 0.4 parts by weight of Compound D1; based on 100 parts by weight of a solvent, i.e. methyl benzoate. In addition, the evaluation was also performed in the same manner. The results of evaluation are shown in Table 4.

Examples 5 to 10 and Comparative Examples 2 and 5 to 9

Organic light-emitting devices were prepared in substantially the same manner as in Example 1 except that the composition of an ink for an emission layer was changed as shown in Table 4.

TABLE 4

| | Emission layer composition | Driving voltage (V) @1,000 cd/m$^2$ | Current efficiency (relative value) @1,000 cd/m$^2$ | Emission lifespan (relative value) |
|---|---|---|---|---|
| Example 4 | Compound 1:H2-34:Az1:D1 (33:33:33:10) | 5.9 | 149 | 625 |
| Example 5 | Compound 2:H2-34:Az1:D1 (33:33:33:10) | 5.8 | 145 | 590 |
| Example 6 | Compound 11:H2-34:Az1:D1 (33:33:33:10) | 5.9 | 140 | 630 |
| Example 7 | Compound 1:H1-1:Az1:D1 (33:33:33:10) | 8.4 | 155 | 655 |
| Example 8 | Compound 11:H1-1:Az1:D1 (33:33:33:10) | 8.4 | 151 | 630 |
| Example 9 | Compound 1:H3-3:Az1:D1 (33:33:33:10) | 6.8 | 139 | 620 |
| Example 10 | Compound 11:H3-3:Az1:D1 (33:33:33:10) | 6.9 | 142 | 625 |
| Comparative Example 2 | H2-34:Az1:D1 (80:20:10) | 4.7 | 100 | 100 |
| Comparative Example 5 | H2-34:Az1:D1 (50:50:10) | 5.0 | 108 | 85 |
| Comparative Example 6 | H1-1:Az1:D1 (50:50:10) | 8.0 | 112 | 75 |
| Comparative Example 7 | H3-3:Az1:D1 (50:50:10) | 5.4 | 131 | 125 |
| Comparative Example 8 | Compound C2:H2-34:Az1:D1 (33:33:33:10) | *1 Device preparation not possible | *1 Device preparation not possible | *1 Device preparation not possible |
| Comparative Example 9 | Compound C3:H2-34:Az1:D1 (33:33:33:10) | *1 Device preparation not possible | *1 Device preparation not possible | *1 Device preparation not possible |

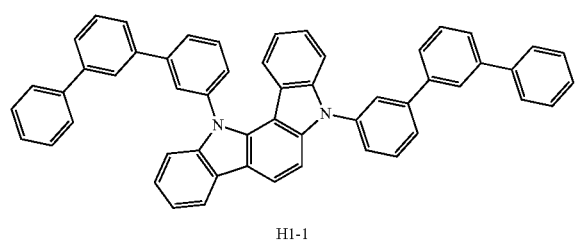 [SMILES: c1ccc(-c2cccc(-c3cccc(-n4c5ccccc5c5c4ccc4c6ccccc6n(-c6cccc(-c7cccc(-c8ccccc8)c7)c6)c45)c3)c2)cc1]

H1-1

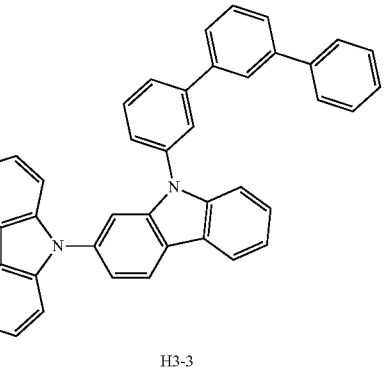

H3-3

As shown in Table 4, in Examples of a composition including carbazole derivatives (H1-1, H2-34, and H3-3), in the case of the organic light-emitting devices of Examples 4 to 10 each using an emission layer including, as a host material, a composition including the compounds according to the present disclosure, the luminescence efficiency and emission lifespan were significantly improved, as compared with the organic light-emitting device of Comparative Examples 2 and 5 to 7 using an emission layer not including the compounds according to the present disclosure.

Also, the solubilities of Comparative Example Compounds C2 and C3, were deficient. Thus, it was found that an organic light-emitting device was not prepared by a coating method (Comparative Examples 8 and 9).

In addition, regarding the comparison of the evaluation results of Tables 3 and 4, the Examples, in which the composition for forming the emission layer included carbazole ring derivatives, were found to have a decreased driving voltage and lower power consumption, as compared with the Examples, in which composition for forming the emission layer did not include carbazole ring derivatives.

While the present disclosure has been described with Synthesis Examples and Examples, the present disclosure is not limited to the specific Examples, and various modifications may be made within the scope of the disclosure described in the claims.

As described above, the heterocyclic compound has a low glass transition temperature and high solubility, thereby increasing the pot life of the solution containing the compound. Thus, the heterocyclic compound may be suitable for use in a solution coating method.

In addition, an organic light-emitting device including the heterocyclic compound may have high luminescence efficiency and long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A heterocyclic compound represented by Formula 1:

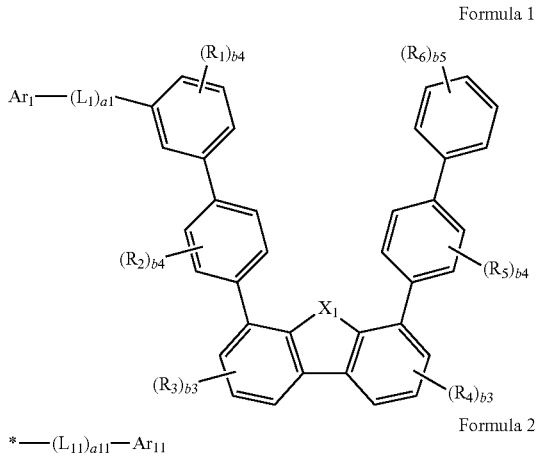

Formula 1

Formula 2

$*\text{---}(L_{11})_{a11}\text{---}Ar_{11}$ wherein the heterocyclic compound satisfies Equation 1:

$|E_{HOMO} - E_{LUMO}| \geq 3.0 \text{ eV}$  Equation 1 wherein, in Equation 1, $E_{HOMO}$ indicates a HOMO energy level value of the heterocyclic compound, and $E_{LUMO}$ indicates a LUMO energy level value of the heterocyclic compound, wherein, in Formulae 1 and 2, $X_1$ is O, S, or Se, $L_1$ and $L_{11}$ are each independently a single bond, a substituted or unsubstituted benzene group, or a substituted or unsubstituted naphthalene group, a1 and a11 are each independently an integer from 1 to 10, $Ar_1$ and $Ar_{11}$ are each independently a substituted or unsubstituted benzene group, or a substituted or unsubstituted naphthalene group, $R_1$ to $R_6$ are each independently a group represented by Formula 2, hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, or a substituted or unsubstituted $C_1$-$C_{60}$ alkoxy group, b3 is an integer from 0 to 3, b4 is an integer from 0 to 4, b5 is an integer from 0 to 5, at least one substituent of the substituted benzene group, the substituted naphthalene group, the substituted $C_1$-$C_{60}$ alkyl group, the substituted $C_2$-$C_{60}$ alkenyl group, the substituted $C_2$-$C_{60}$ alkynyl group, and the substituted $C_1$-$C_{60}$ alkoxy group is:

deuterium, —F, —Cl, —Br, —I, —CD$_3$, —CD$_2$H, —CDH$_2$, —CF$_3$, —CF$_2$H, —CFH$_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, or any combination thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —F, —Cl, —Br, —I, —CD$_3$, —CD$_2$H, —CDH$_2$, —CF$_3$, —CF$_2$H, —CFH$_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, —Si(Q$_{11}$)(Q$_{12}$)(Q$_{13}$), —N(Q$_{11}$)(Q$_{12}$), —C(=O)(Q$_{11}$), or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, or any combination thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, or any combination thereof, each substituted with at least one deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, —Si(Q$_{21}$)(Q$_{22}$)(Q$_{23}$), —N(Q$_{21}$)(Q$_{22}$), —C(=O)(Q$_{21}$), or any combination thereof; or —Si(Q$_{31}$)(Q$_{32}$)(Q$_{33}$), —N(Q$_{31}$)(Q$_{32}$), —C(=O)(Q$_{31}$), or any combination thereof, wherein Q$_{11}$ to Q$_{13}$, Q$_{21}$ to Q$_{23}$, and Q$_{31}$ to Q$_{33}$ are each independently hydrogen, deuterium, a $C_1$-$C_{20}$ alkyl group, a $C_1$-$C_{20}$ alkoxy group, a phenyl group, or a biphenyl group, and

* indicates a binding site to an adjacent atom.

2. The heterocyclic compound of claim 1, wherein $X_1$ is O or S.

3. The heterocyclic compound of claim 1, wherein $L_1$ and $L_{11}$ are each independently a single bond or a group represented by Formulae 3-1 or 3-2, and when a1 and a11 are each 2 or greater, $(L_1)_{a1}$ and $(L_{11})_{a11}$ are each independently a single bond or a group represented by one of Formulae 3-1 to 3-3:

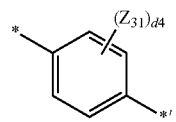

3-1

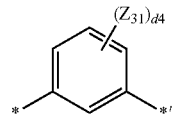

3-2

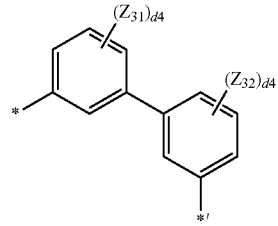

3-3 wherein, $Z_{31}$ and $Z_{32}$ are each independently hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, or —Si($Q_{31}$)($Q_{32}$)($Q_{33}$), d4 is an integer from 0 to 4, $Q_{31}$ to $Q_{33}$ are each independently hydrogen, deuterium, a $C_1$-$C_{20}$ alkyl group, a $C_1$-$C_{20}$ alkoxy group, a phenyl group, or a biphenyl group, and \* and \*' each indicate a binding site to an adjacent atom.

4. The heterocyclic compound of claim 1, wherein a1 and a11 are each independently 1 or 2.

5. A heterocyclic compound represented by Formula 1:

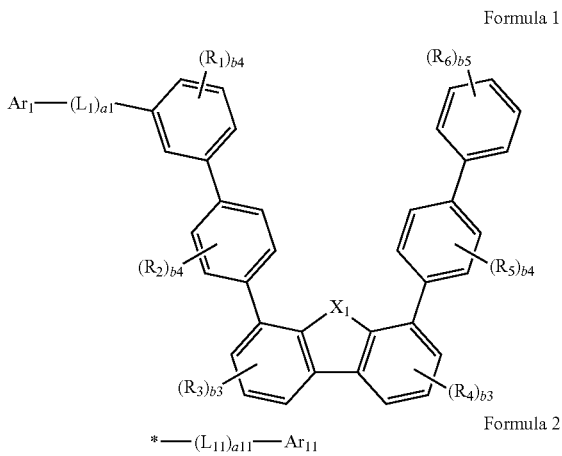

Formula 1

Formula 2 wherein, in Formulae 1 and 2, $X_1$ is O, S, or Se, i) $L_1$ is a single bond, $L_{11}$ is a substituted or unsubstituted benzene group, and a11 is 1 or 2;

ii) $L_1$ and $L_{11}$ are each a substituted or unsubstituted benzene group, and a1 and a11 are each 1;

iii) $L_1$ and $L_{11}$ are each a substituted or unsubstituted benzene group, a1 is 1, and a11 is 2; or iv) $L_1$ and $L_{11}$ are each a substituted or unsubstituted benzene group, and a1 and a11 are each 2, $Ar_1$ and $Ar_{11}$ are each independently a substituted or unsubstituted benzene group, or a substituted or unsubstituted naphthalene group, $R_1$ to $R_6$ are each independently a group represented by Formula 2, hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, or a substituted or unsubstituted $C_1$-$C_{60}$ alkoxy group, b3 is an integer from 0 to 3, b4 is an integer from 0 to 4, b5 is an integer from 0 to 5, at least one substituent of the substituted benzene group, the substituted naphthalene group, the substituted $C_1$-$C_{60}$ alkyl group, the substituted $C_2$-$C_{60}$ alkenyl group, the substituted $C_2$-$C_{60}$ alkynyl group, and the substituted $C_1$-$C_{60}$ alkoxy group is:

deuterium, —F, —Cl, —Br, —I, —CD$_3$, —CD$_2$H, —CDH$_2$, —CF$_3$, —CF$_2$H, —CFH$_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, or any combination thereof;

a $C_1$-$C_{60}$ alkyl group, a $C_2$-$C_{60}$ alkenyl group, a $C_2$-$C_{60}$ alkynyl group, a $C_1$-$C_{60}$ alkoxy group, or any combination thereof, each substituted with at least one deuterium, —F, —Cl, —Br, —I, —CD$_3$, —CD$_2$H, —CDH$_2$, —CF$_3$, —CF$_2$H, —CFH$_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, Si($Q_{11}$)($Q_{12}$)($Q_{13}$), —N($Q_{11}$)($Q_{12}$), —C(=O)($Q_{11}$), or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, or any combination thereof:

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, or any combination thereof, each substituted with at least one deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, —Si($Q_{21}$)($Q_{22}$)($Q_{23}$), —N($Q_{21}$)($Q_{22}$), —C(=O)($Q_{21}$), or any combination thereof; or —Si($Q_{31}$)($Q_{32}$)($Q_{33}$), —N($Q_{31}$)($Q_{32}$), —C(=O)($Q_{31}$), or any combination thereof, wherein $Q_{11}$ to $Q_{13}$, $Q_{21}$ to $Q_{23}$, and $Q_{31}$ to $Q_{33}$ are each independently hydrogen, deuterium, a $C_1$-$C_{20}$ alkyl group, a $C_1$-$C_{20}$ alkoxy group, a phenyl group, or a biphenyl group, and \* indicates a binding site to an adjacent atom.

6. The heterocyclic compound of claim 1, wherein the moiety represented by \*-(L$_1$)$_{a1}$-Ar$_1$ is represented by any one of Formulae 4-1 to 4-5:

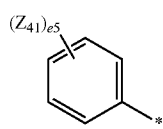

4-1

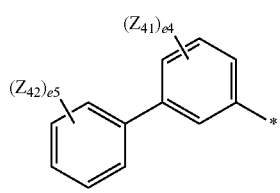

4-2

-continued 4-3

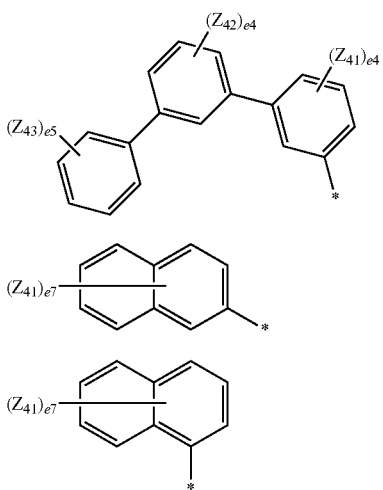

4-4

4-5

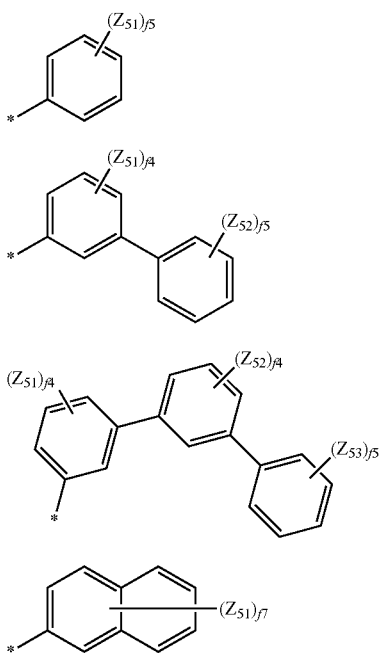

wherein, $Z_{41}$ to $Z_{43}$ are each independently hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, or —Si($Q_{31}$)($Q_{32}$)($Q_{33}$), e4 is an integer from 0 to 4, e5 is an integer from 0 to 5, e7 is an integer from 0 to 7, $Q_{31}$ to $Q_{33}$ are each independently hydrogen, deuterium, a $C_1$-$C_{20}$ alkyl group, a $C_1$-$C_{20}$ alkoxy group, a phenyl group, or a biphenyl group, and

* indicates a binding site to an adjacent atom.

7. The heterocyclic compound of claim 1, wherein the group represented by Formula 2 is represented by any of Formulae 2-1 to 2-6:

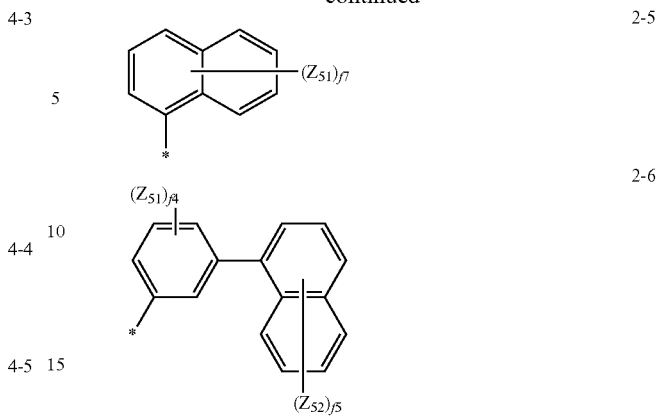

-continued

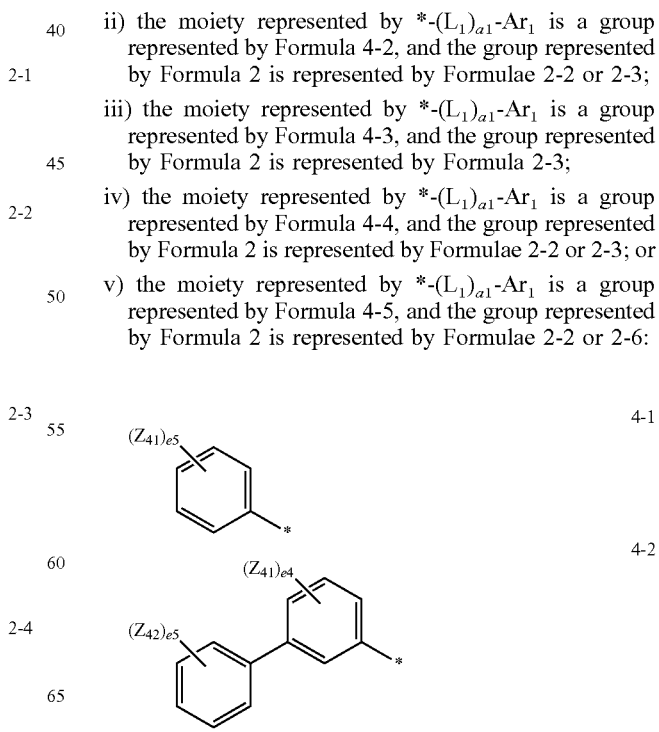

wherein, $Z_{51}$ to $Z_{53}$ are each independently hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, or —Si($Q_{31}$)($Q_{32}$)($Q_{33}$), f4 is an integer from 0 to 4, f5 is an integer from 0 to 5, f7 is an integer from 0 to 7, $Q_{31}$ to $Q_{33}$ are each independently hydrogen, deuterium, a $C_1$-$C_{20}$ alkyl group, a $C_1$-$C_{20}$ alkoxy group, a phenyl group, or a biphenyl group, and

* indicates a binding site to an adjacent atom.

8. The heterocyclic compound of claim 1, wherein i) the moiety represented by *-(L$_1$)$_{a1}$-Ar$_1$ is a group represented by Formula 4-1, and the group represented by Formula 2 is represented by any of Formulae 2-1 to 2-3, 2-5, and 2-6;

ii) the moiety represented by *-(L$_1$)$_{a1}$-Ar$_1$ is a group represented by Formula 4-2, and the group represented by Formula 2 is represented by Formulae 2-2 or 2-3;

iii) the moiety represented by *-(L$_1$)$_{a1}$-Ar$_1$ is a group represented by Formula 4-3, and the group represented by Formula 2 is represented by Formula 2-3;

iv) the moiety represented by *-(L$_1$)$_{a1}$-Ar$_1$ is a group represented by Formula 4-4, and the group represented by Formula 2 is represented by Formulae 2-2 or 2-3; or v) the moiety represented by *-(L$_1$)$_{a1}$-Ar$_1$ is a group represented by Formula 4-5, and the group represented by Formula 2 is represented by Formulae 2-2 or 2-6:

-continued

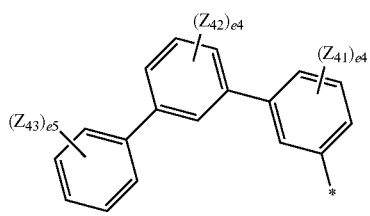

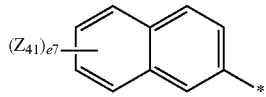

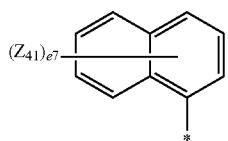

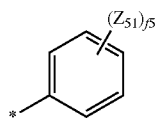

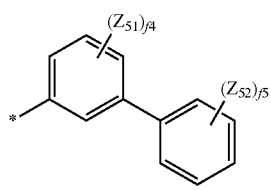

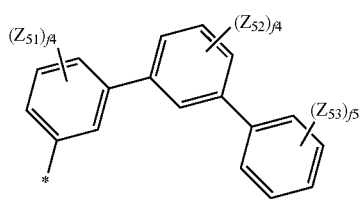

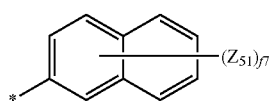

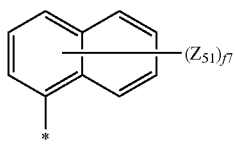

-continued

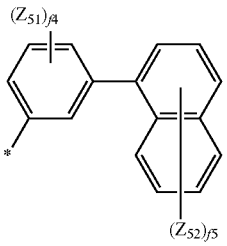

wherein, $Z_{41}$ to $Z_{43}$ and $Z_{51}$ to $Z_{53}$ are each independently hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, or —Si($Q_{31}$)($Q_{32}$)($Q_{33}$), e4 and f4 are each independently an integer from 0 to 4, e5 and f5 are each independently an integer from 0 to 5, e7 and f7 are each independently an integer from 0 to 7, $Q_{31}$ to $Q_{33}$ are each independently hydrogen, deuterium, a $C_1$-$C_{20}$ alkyl group, a $C_1$-$C_{20}$ alkoxy group, a phenyl group, or a biphenyl group, and

* indicates a binding site to an adjacent atom.

9. The heterocyclic compound of claim 1, wherein $R_1$ and $R_6$ are each independently a group represented by Formula 2 or hydrogen.

10. The heterocyclic compound of claim 1, wherein $R_2$ to $R_5$ are each independently hydrogen, deuterium, —F, —Cl, —Br, —I, a cyano group, a $C_1$-$C_{20}$ alkyl group, a $C_2$-$C_{20}$ alkenyl group, a $C_2$-$C_{20}$ alkynyl group, a $C_1$-$C_{20}$ alkoxy group; or a $C_1$-$C_{20}$ alkyl group, a $C_2$-$C_{20}$ alkenyl group, a $C_2$-$C_{20}$ alkynyl group, or a $C_1$-$C_{20}$ alkoxy group, each substituted with at least one deuterium, —F, —Cl, —Br, —I, a cyano group, or a combination thereof.

11. The heterocyclic compound of claim 1, wherein the heterocyclic compound is represented by any of Formulae 1-1 to 1-4:

Formula 1-1

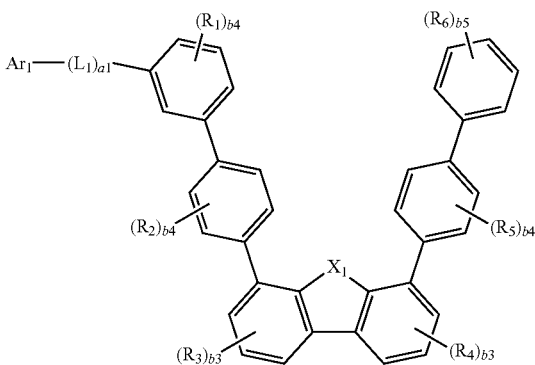

Formula 1-2

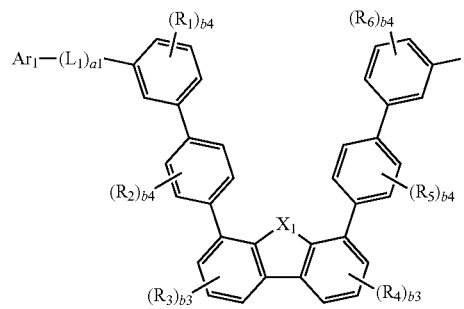

Formula 1-3

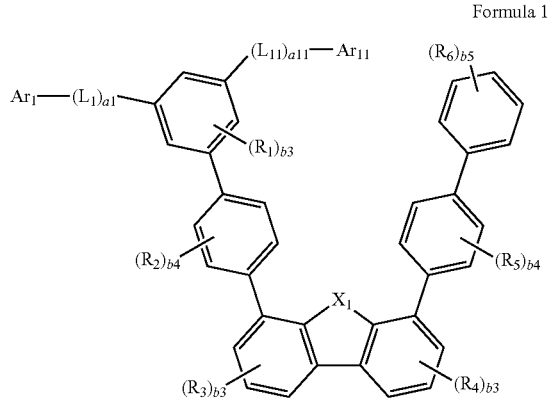

Formula 1-4

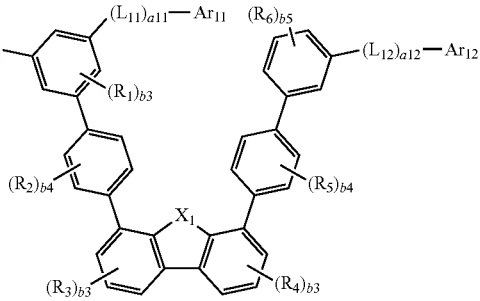

wherein, in Formulae 1-1 to 1-4,
$X_1$, $L_1$, $L_{11}$, a1, a11, $Ar_1$, $Ar_{11}$, b3, b4, and b5 are respectively understood by referring to the descriptions of $X_1$, $L_1$, $L_{11}$, a1, a11, $Ar_1$, $Ar_{11}$, b3, b4, and b5 in claim 1, $L_{12}$, a12, and $Ar_{12}$ are respectively understood by referring to the descriptions of $L_{11}$, a11, and $Ar_{11}$ in claim 1, and $R_1$ to $R_6$ are each independently hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, or a substituted or unsubstituted $C_1$-$C_{60}$ alkoxy group.

12. A heterocyclic compound, wherein the heterocyclic compound is at least one of Compounds 1 to 24:

1

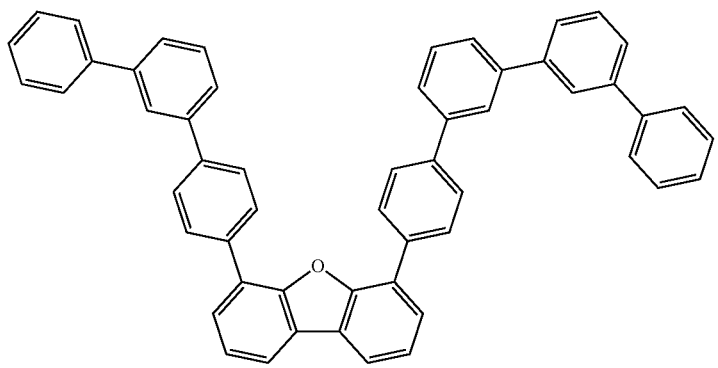

2

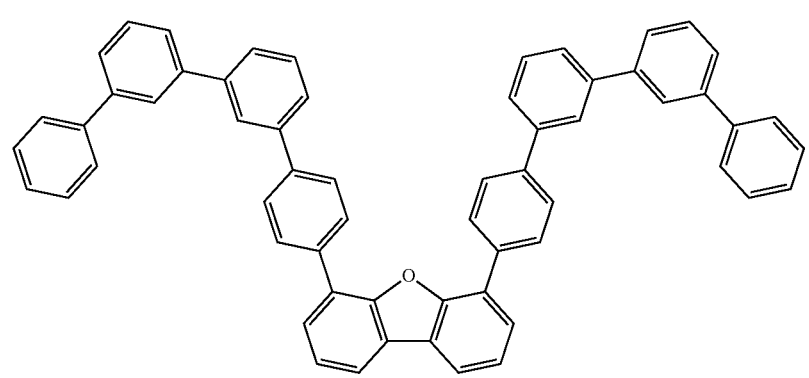

-continued
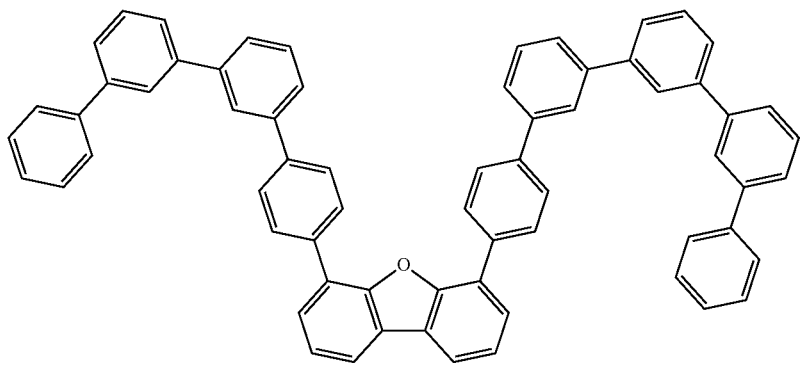
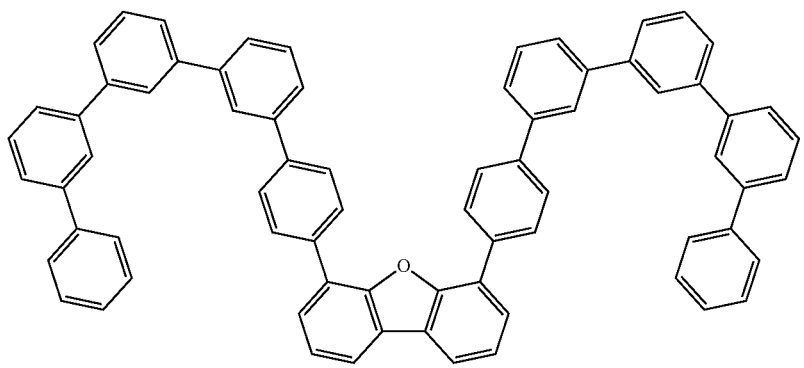
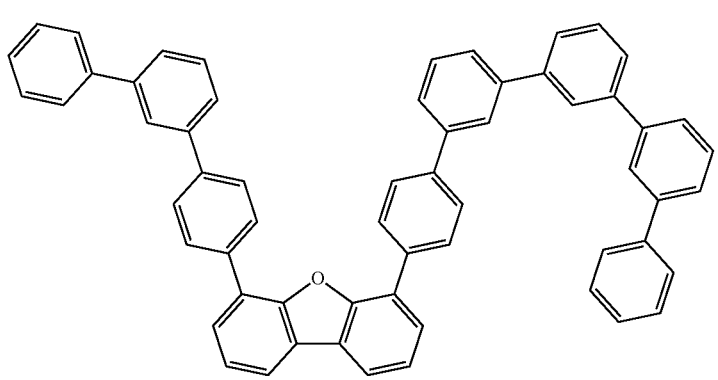
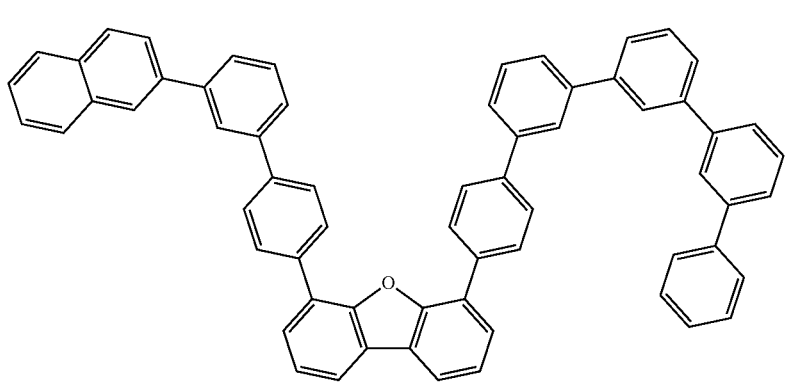

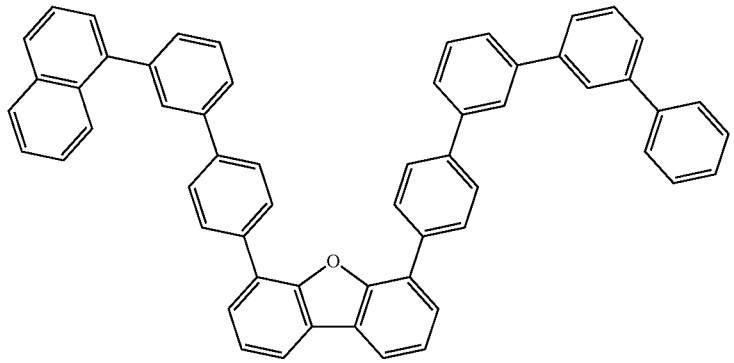
7
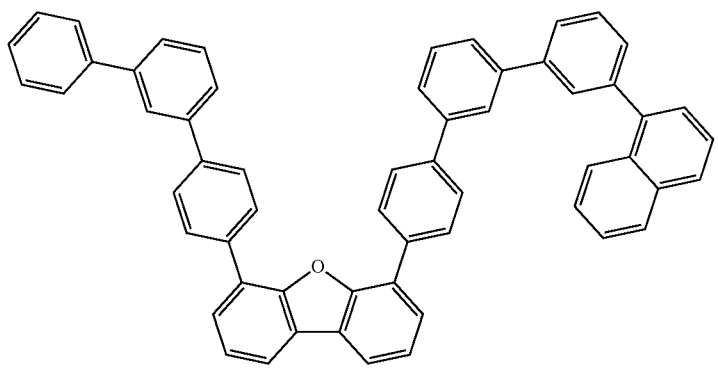
8
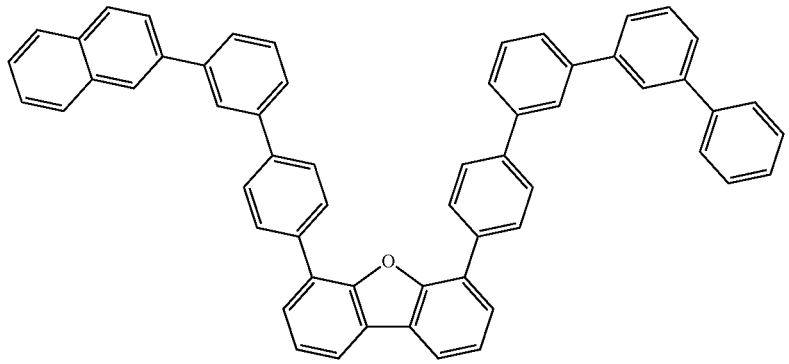
9
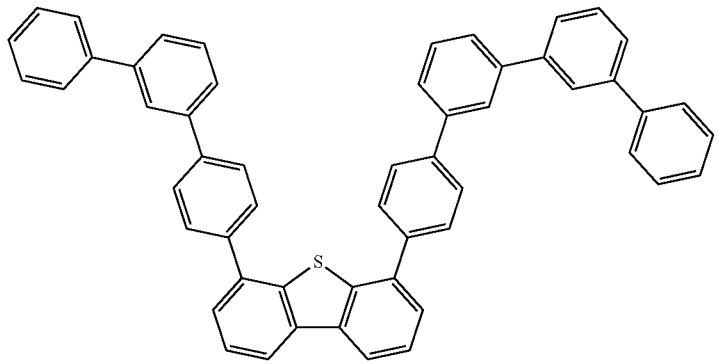
10

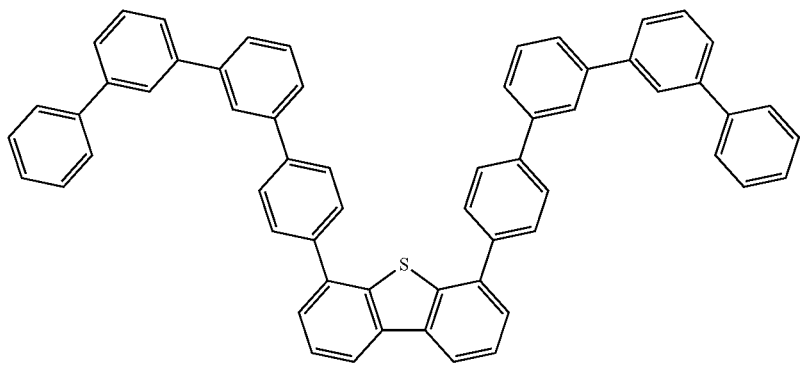
11
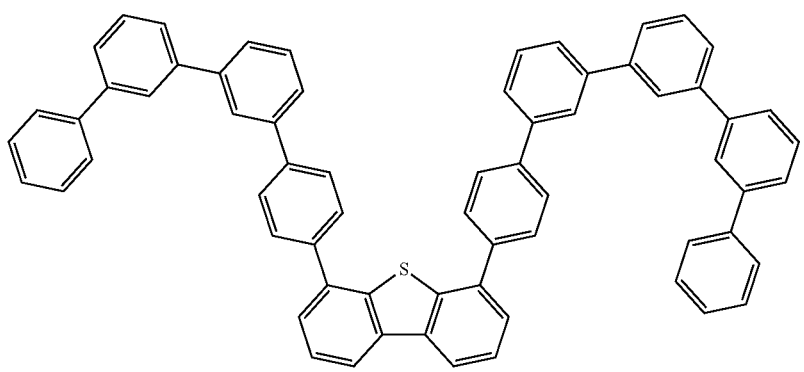
12
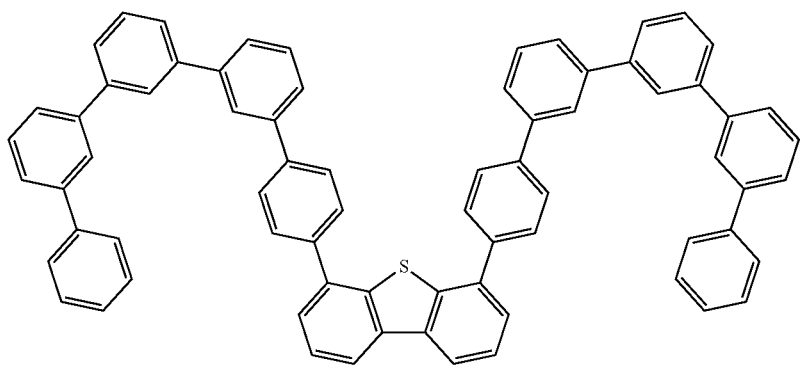
13
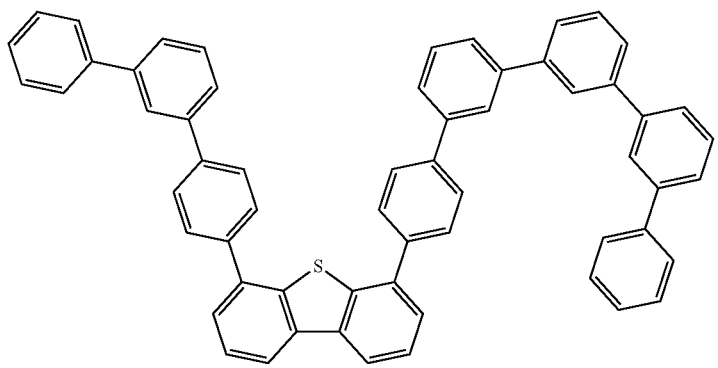
14

15
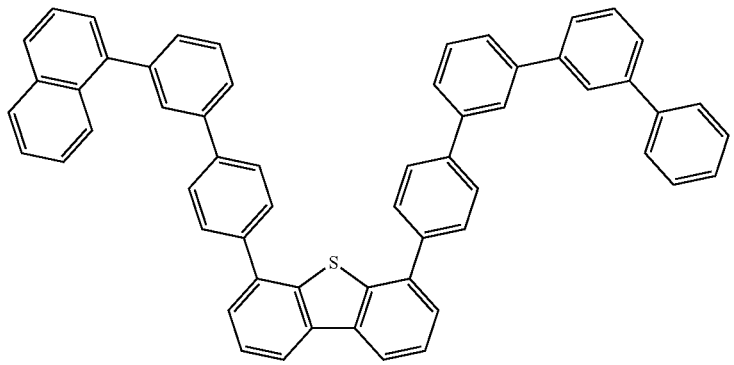
16
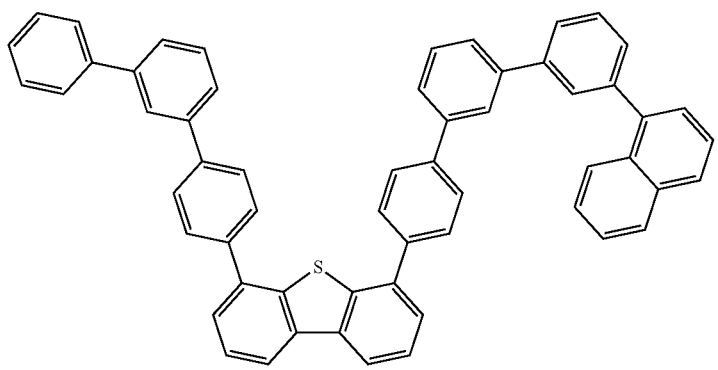
17
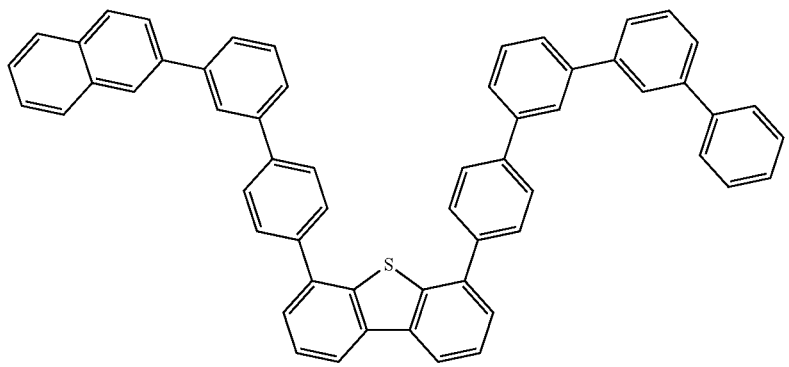
18
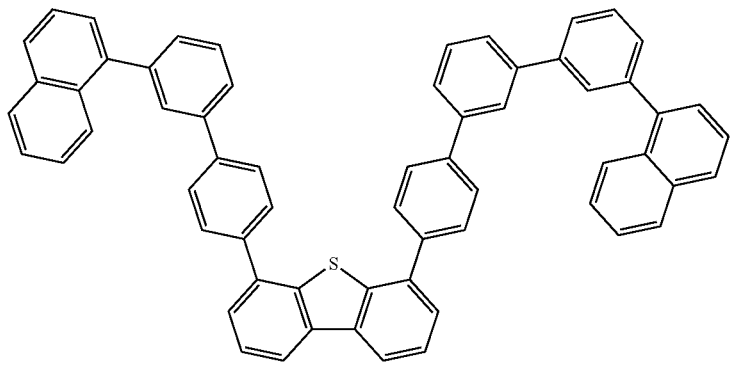

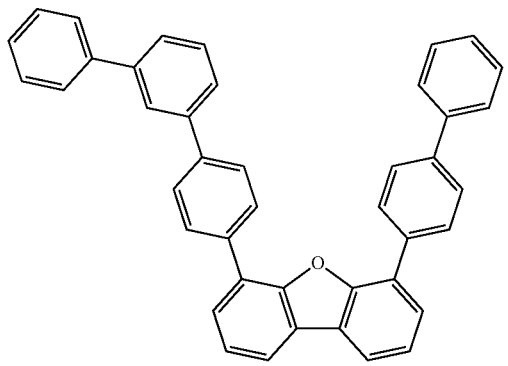
19

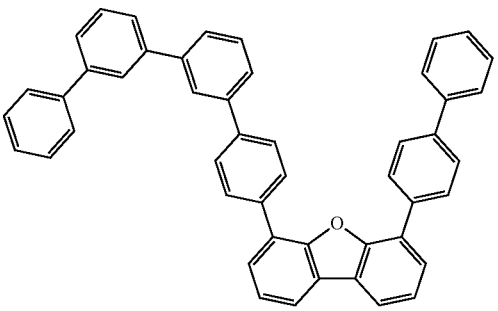
20

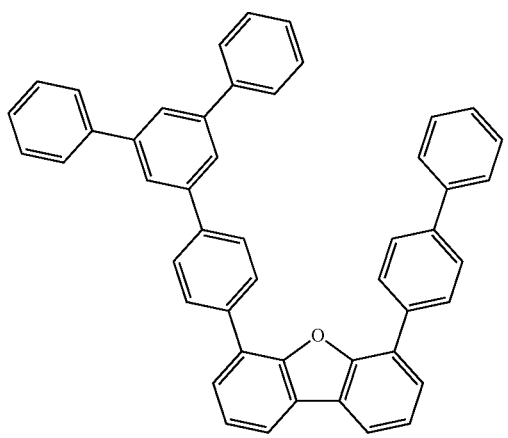
21

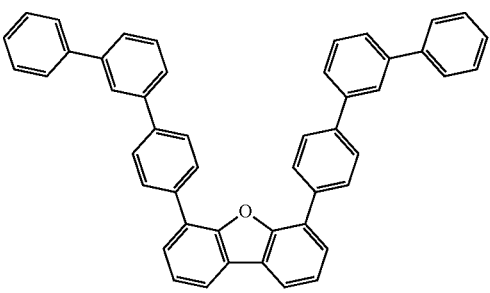
22

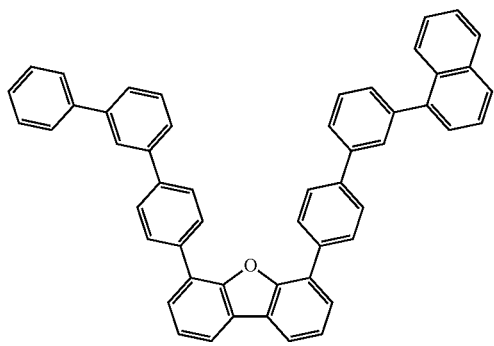
23

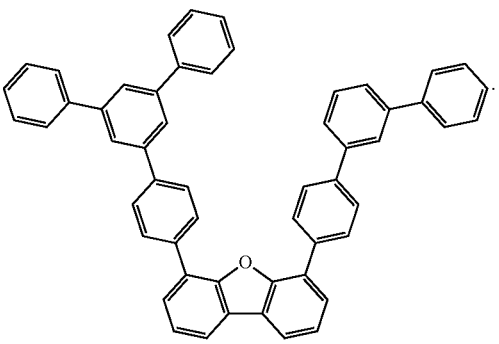
24

13. A composition comprising at least one of the heterocyclic compound represented by Formula 1 of claim 1.

14. The composition of claim 13, wherein the composition further comprises a first compound comprising a carbazole-based moiety.

15. The composition of claim 13, wherein the composition further comprises a second compound comprising an azine-based moiety.

16. The composition of claim 13, wherein the composition further comprises a luminescent material.

17. The composition of claim 13, wherein the composition further comprises a solvent.

18. An organic light-emitting device comprising: a first electrode; a second electrode; and an organic layer between the first electrode and the second electrode and comprising an emission layer and at least one of the heterocyclic compound represented by Formula 1 of claim 1.

19. The organic light-emitting device of claim 18, wherein the organic layer further comprises a luminescent material, and the luminescent material emits light from triplet excitons.

* * * * *